(12) United States Patent
Boudreault et al.

(10) Patent No.: US 8,927,749 B2
(45) Date of Patent: Jan. 6, 2015

(54) ORGANIC ELECTROLUMINESCENT MATERIALS AND DEVICES

(71) Applicants: Pierre-Luc T. Boudreault, Pennington, NJ (US); Chuanjun Xia, Lawrenceville, NJ (US)

(72) Inventors: Pierre-Luc T. Boudreault, Pennington, NJ (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 126 days.

(21) Appl. No.: 13/788,775

(22) Filed: Mar. 7, 2013

(65) Prior Publication Data

US 2014/0252318 A1 Sep. 11, 2014

(51) Int. Cl.
*C07F 7/00* (2006.01)
*H01L 35/24* (2006.01)
*H01L 51/00* (2006.01)

(52) U.S. Cl.
CPC ........ *H01L 51/0094* (2013.01); *H01L 51/0071* (2013.01); *H01L 51/0072* (2013.01)
USPC ................ 556/87; 556/407; 549/4; 549/214; 548/406; 544/69; 313/600; 257/40

(58) Field of Classification Search
USPC ................ 556/87, 407; 549/4, 214; 548/406; 544/69; 313/600; 257/40
See application file for complete search history.

(56) References Cited

U.S. PATENT DOCUMENTS 3,036,005 A * 5/1962 Koch, Jr. ............... 508/203
3,065,251 A * 11/1962 Jones et al. ............ 556/407

(Continued)

FOREIGN PATENT DOCUMENTS

| EP | 0650955 | 5/1995 |
|---|---|---|
| EP | 1725079 | 11/2006 |

(Continued)

OTHER PUBLICATIONS

Akihiro Ito et al., A Spiro-Fused Triarylaminium Radical Cation with a Triplet Ground State, Angew. Chem. Int. Ed. 2003, 42 (8), 921-924.

(Continued)

*Primary Examiner* — Porfirio Nazario Gonzalez
(74) *Attorney, Agent, or Firm* — Duane Morris LLP

(57) ABSTRACT

A compound according to a formula I and devices incorporating the same are described. The compound according to the formula I can have the structure:

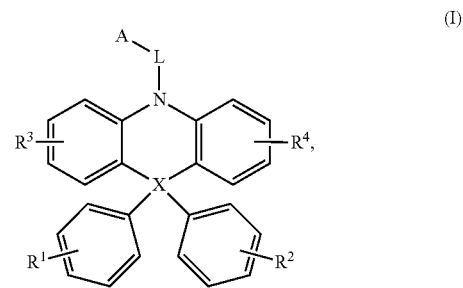

wherein X is Si or Ge; $R^1$ and $R^2$ represent mono, di, tri, tetra, or penta substitutions or no substitution; $R^3$, $R^4$ represent mono, di, tri, or tetra substitutions or no substitution; $R^1$ and $R^2$ are optionally joined to form a ring, which may be further substituted; L is a single bond or comprises an aryl or heteroaryl group having from 5-20 carbon atoms, which is optionally further substituted; and A is an aromatic group. A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof, which are optionally further substituted. The device can include the compound according to Formula I in an organic layer.

24 Claims, 3 Drawing Sheets

(56) References Cited

U.S. PATENT DOCUMENTS

| | | | |
|---|---|---|---|
| 3,079,414 A * | 2/1963 | Gilman et al. | 556/87 |
| 3,103,529 A * | 9/1963 | Tamborski et al. | 556/407 |
| 3,120,565 A * | 2/1964 | Kollonitsch | 564/374 |
| 3,131,203 A * | 4/1964 | Erickson et al. | 556/407 |
| 3,143,560 A * | 8/1964 | Wasserman et al. | 556/407 |
| 3,159,661 A * | 12/1964 | Jones et al. | 556/407 |
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Hueschen | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |

FOREIGN PATENT DOCUMENTS

| | | |
|---|---|---|
| EP | 2034538 | 3/2009 |
| EP | 2161319 | 10/2010 |
| JP | 08302339 | 11/1996 |
| JP | 10168444 | 6/1998 |
| JP | 10218884 | 8/1998 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 2001039234 | 5/2001 |
| WO | 0202714 | 1/2002 |
| WO | 0215645 | 2/2002 |
| WO | 200215645 | 2/2002 |
| WO | 03040257 | 5/2003 |
| WO | 2003040257 | 5/2003 |
| WO | 03060956 | 7/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011073149 | 6/2011 |
| WO | 2011136484 | 11/2011 |

OTHER PUBLICATIONS

Akihiro Ito et al., para-Phenylene-Bridged Spirobi(triarylamine) Dimer with Four Perpendicularly Linked Redox-Active p Systems, Chem. Eur. J. 2010, 16, 10866-10878.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

(56) References Cited

OTHER PUBLICATIONS

Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter, " Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of β-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NΛCΛN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to organic materials used in such devices. More specifically, the present invention relates to host compounds for phosphorescent OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

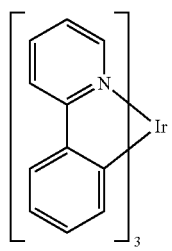

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment of the present disclosure, a compound or a composition comprising the compound is provided. The compound comprises fused aromatic ring structure abridged with nitrogen and silicon or germanium atom. The compound comprises either dibenzo[b,e][1,4]azasiline or dibenzo[b,e][1,4]azagermine. The compound provided in the present disclosure has a general structure of a formula I:

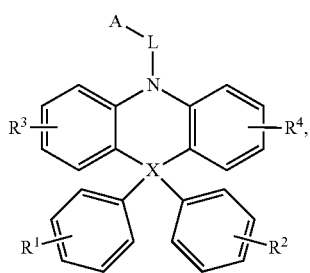

wherein
X is Si or Ge,
$R^1$ and $R^2$ represent mono, di, tri, tetra, or penta substitutions or no substitution,
$R^3$, $R^4$ represent mono, di, tri, or tetra substitutions or no substitution,
$R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof,
$R^1$ and $R^2$ are optionally joined to form a ring, which may be further substituted,
L is a single bond or comprises an aryl or heteroaryl group having from 5-20 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof, and A is an aromatic group.

A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof. A is optionally further substituted with one or more groups selected from hydrogen, deuterium, alkyl, cycloalkyl, arylalkyl, alkoxy, aryloxy, amino, silyl, aryl, heteroaryl, and combinations thereof. The substitution of one or more groups in A is optionally fused to the indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group.

According to another embodiment of the present disclosure, a first device comprising an organic light-emitting device is provided. The first device comprises an anode, a cathode, and an organic layer. The organic layer is disposed between the anode and the cathode, and comprises a compound having the formula I or a composition comprising a compound having the formula I. The compound can be used alone or in combination of other materials in the organic layer for different functions. For example, in some embodiments, the organic layer is an emissive layer and the compound of the formula I is a host material. The compound of the formula I can be also used as a blocking material or an electron transporting material. The first device can be a consumer product, an organic light-emitting device, and/or a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton" is form. An "exciton" is a localized electron-hole pair having an excited energy state. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
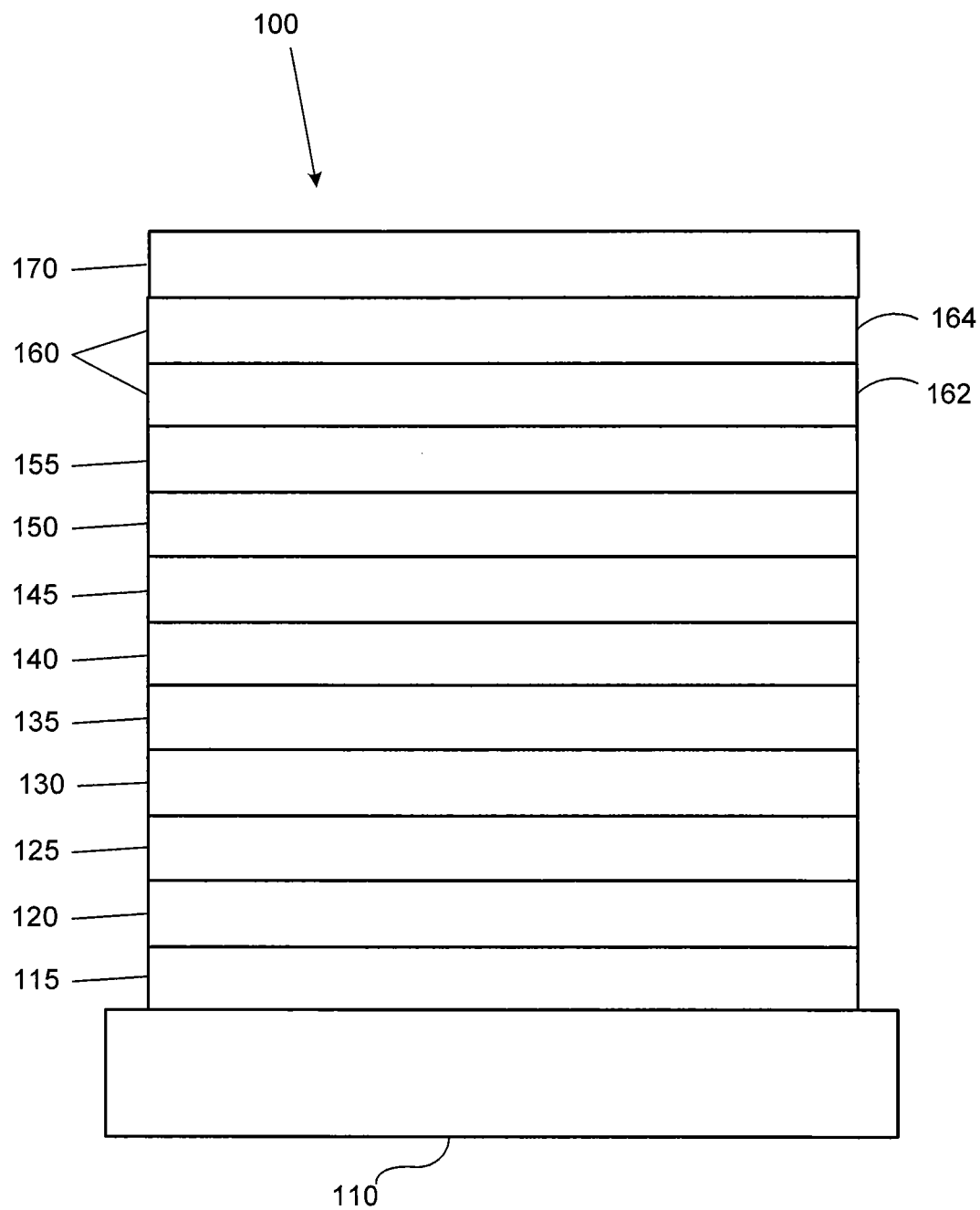
FIG. 1 shows an organic light emitting device.

FIG. 1 shows an organic light-emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 can be a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
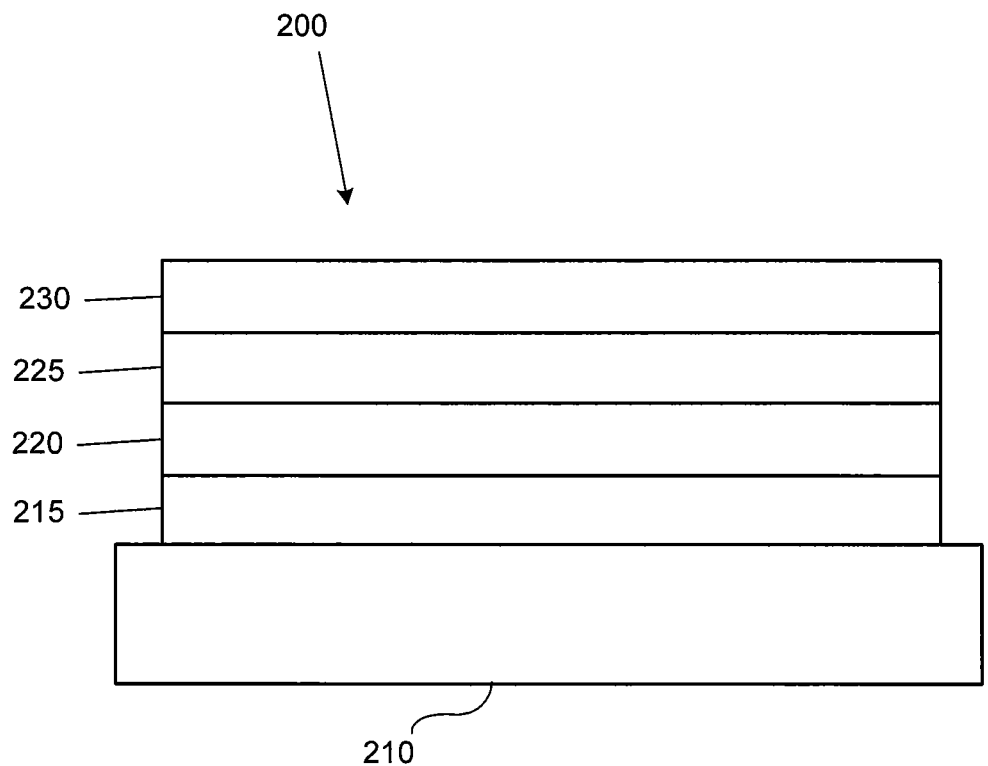
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms for chemical substitution groups such as halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In the chemical formulas in the present disclosure, either a solid line or a dotted line represents a chemical bond or multiple chemical bonds. Unless expressly stated otherwise, the solid lines and the dotted lines do not represent spatial arrangements of chemical bonds in stereochemistry. A solid line or a dotted line across a chemical structure such as a ring or a fused ring represents either one chemical bond or multiple bonds connected with one or multiple possible positions of the chemical structure.

Figure 3:
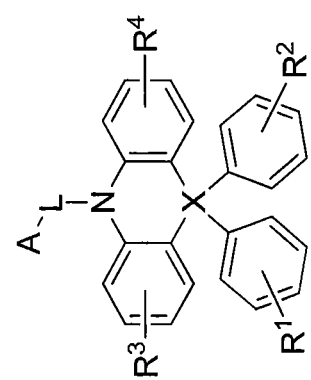
FIG. 3 shows Formula I as disclosed herein.

According to an embodiment of the present disclosure, a compound is provided. The compound is suitable as a host material, a blocking material or an electron transporting material for phosphorescent organic light emitting devices (PHOLEDS) of all colors, and particularly as a host for a blue emitter. The disclosed compound comprises a fused aromatic ring structure abridged with nitrogen, and silicon or germanium atom, and comprises either dibenzo[b,e][1,4]azasiline or dibenzo[b,e][1,4]azagermine. As shown in FIG. 3, the compound has a general structure of the formula I:

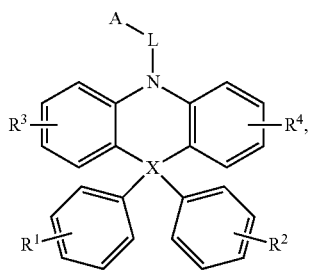

(I)

wherein
X is Si or Ge,
$R^1$ and $R^2$ represent mono, di, tri, tetra, or penta substitutions or no substitution,
$R^3$, $R^4$ represent mono, di, tri, or tetra substitutions or no substitution, $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, $R^1$ and $R^2$ are optionally joined to form a ring, which may be further substituted, L is a single bond or comprises an aryl or heteroaryl group having from 5-20 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof, and A is an aromatic group.

A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof. A is optionally further substituted with one or more groups selected from hydrogen, deuterium, alkyl, cycloalkyl, arylalkyl, alkoxy, aryloxy, amino, silyl, aryl, heteroaryl, and combinations thereof. The substitution of one or more groups in A is optionally fused to the indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group.

Examples of a suitable L include but are not limited to the following moieties:
a single bond,

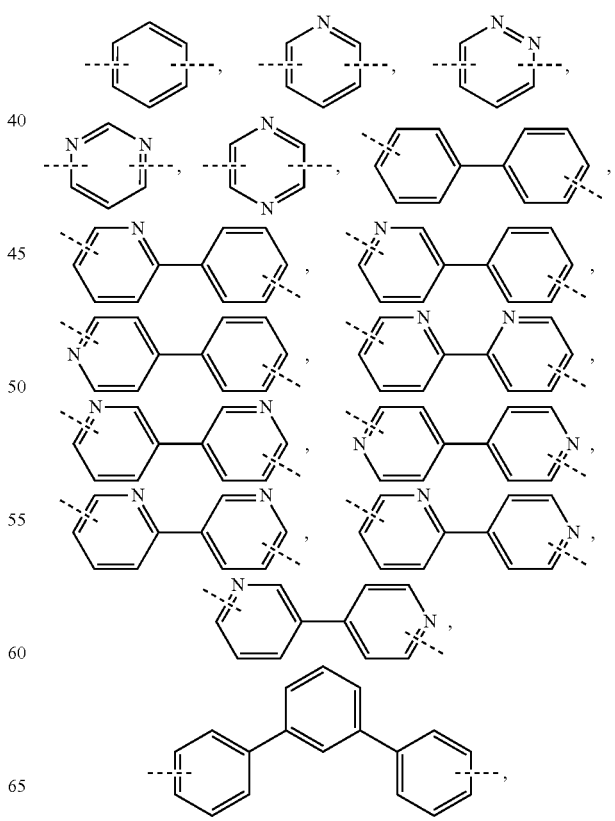

-continued

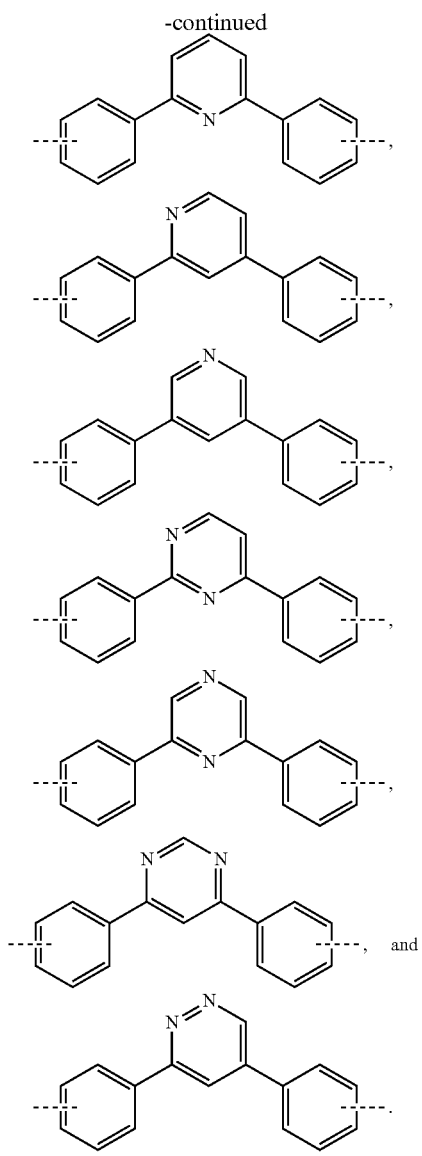

The reference above to a "single bond" means that A is directly connected to the nitrogen atom in the ring structure of either dibenzo[b,e][1,4]azasiline or dibenzo[b,e][1,4]azagermine in the formula I.

In some embodiments, in the compound provided in this disclosure, A has the following general structure:

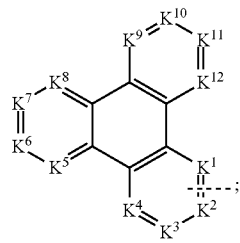

wherein $K^1$ to $K^{12}$ are independently selected from N and C—R', and R' is selected from the group consisting of hydrogen, deuterium, alkyl, cycloalkyl, arylalkyl, alkoxy, aryloxy, amino, silyl, aryl, heteroaryl, and combinations thereof.

In some embodiments, A is selected from the group consisting of:

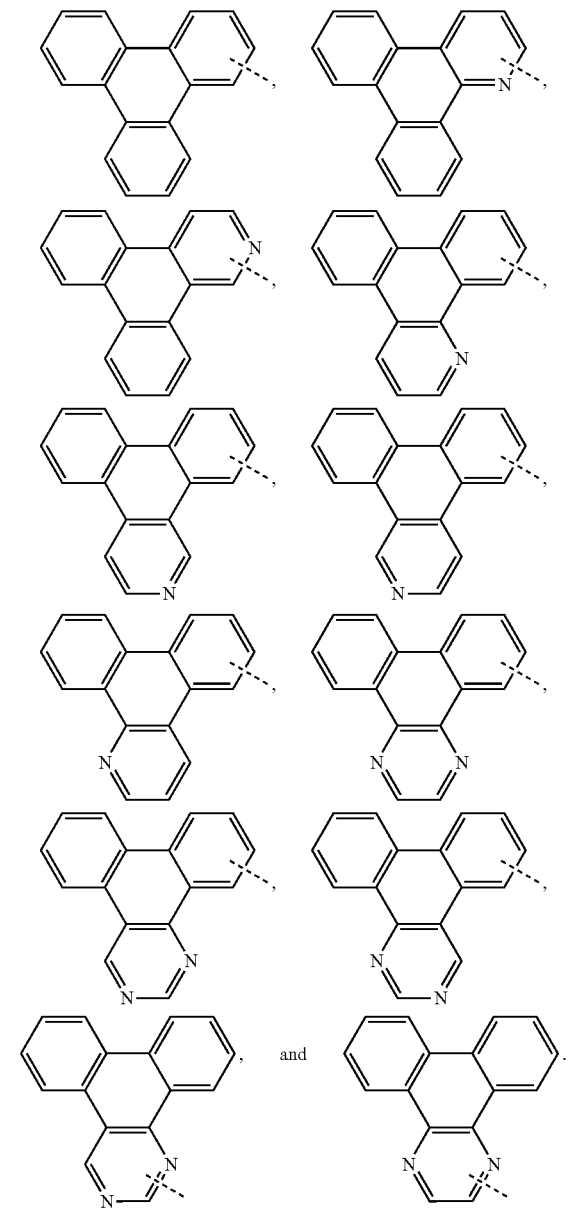

In some embodiments, A is selected from the group consisting of:

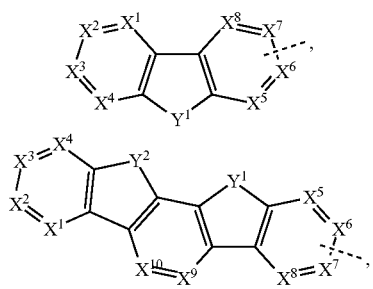

-continued

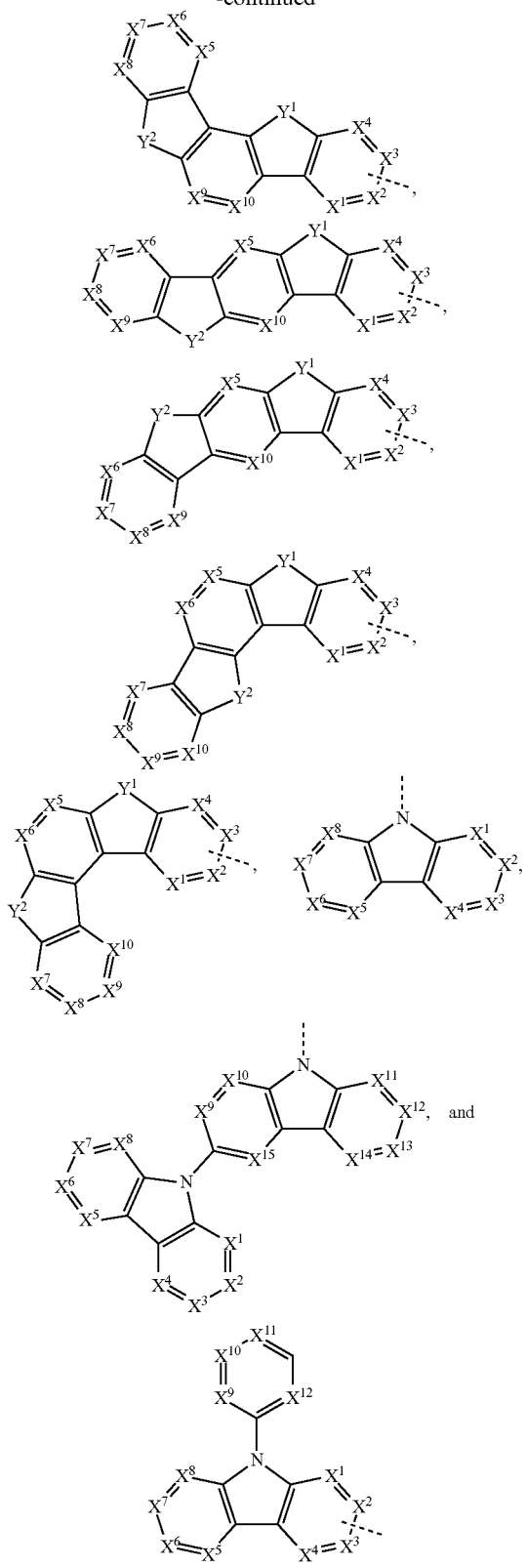

wherein $X^1$-$X^{15}$ are independently selected from the group consisting of N and C—R", where R" is selected from a group consisting of hydrogen, deuterium, alkyl, cycloalkyl, arylalkyl, alkoxy, aryloxy, amino, silyl, aryl, heteroaryl, and combinations thereof. $Y^1$ and $Y^2$ are independently selected from the group consisting of O, S, and Se.

In some embodiments, A is selected from the group consisting of:

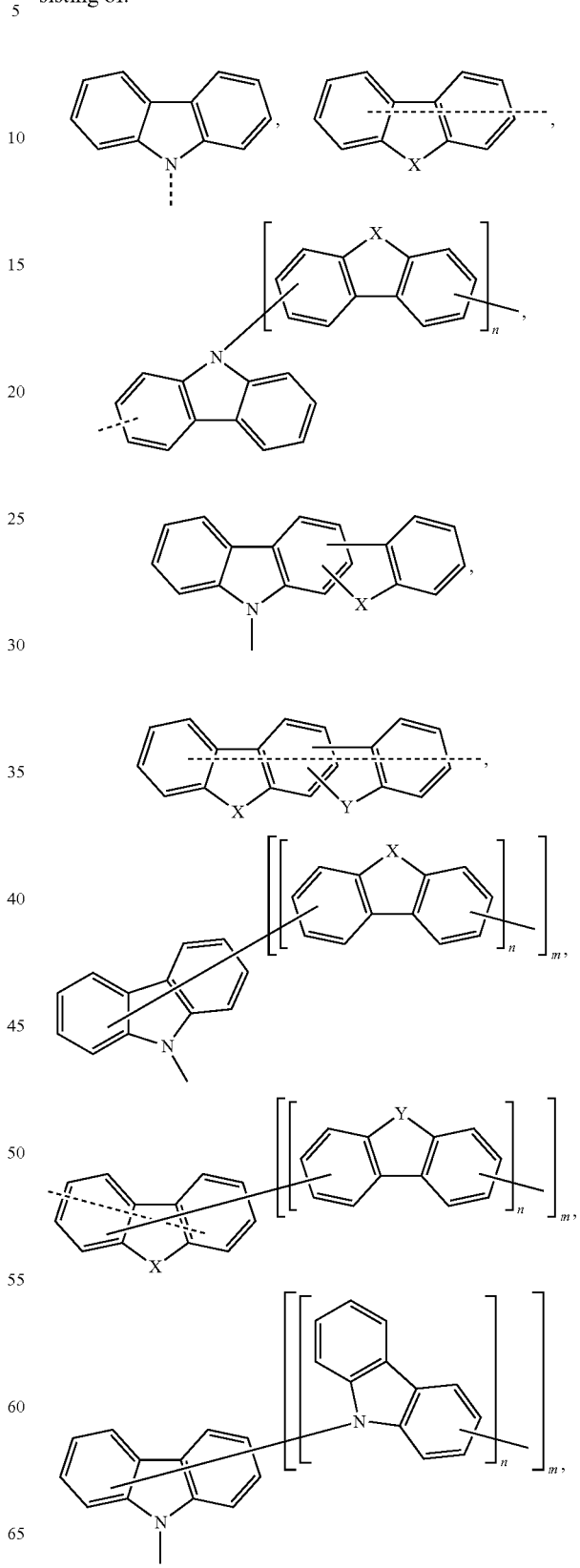

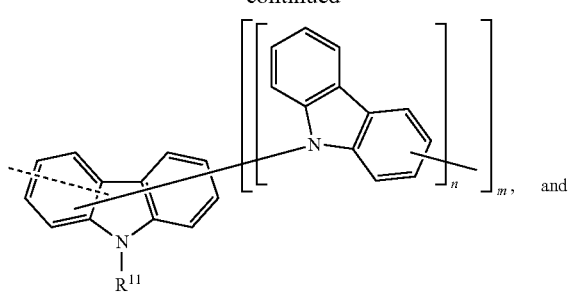
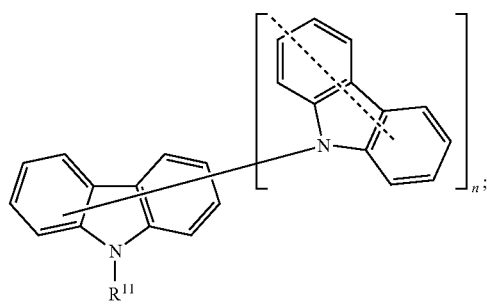
wherein n is an integer from 1 to 20, m is an integer from 1 to 20; X and Y are independently selected from the group consisting of O, S, and $NR^{14}$; and $R^{11}$, $R^{12}$, $R^{13}$ and $R^{14}$ are selected from the group consisting of aryl and heteroaryl.
Additional examples of a suitable A include but are not limited to:
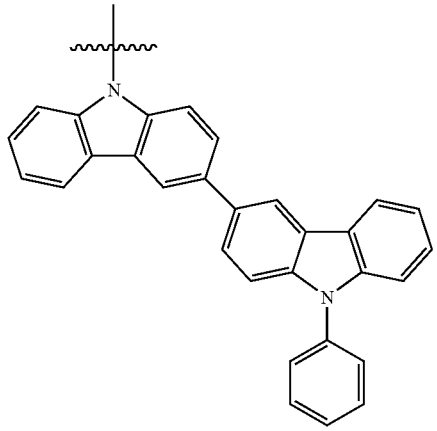
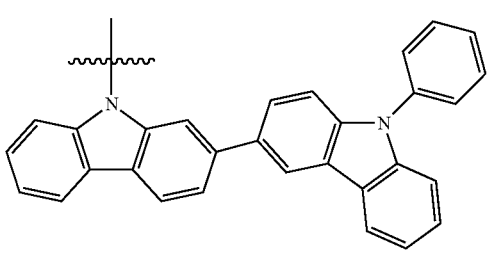
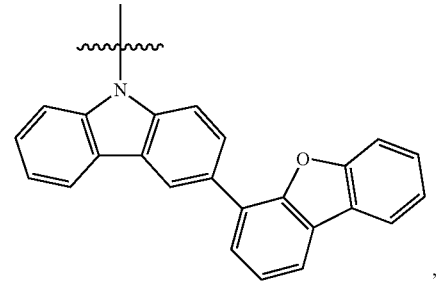
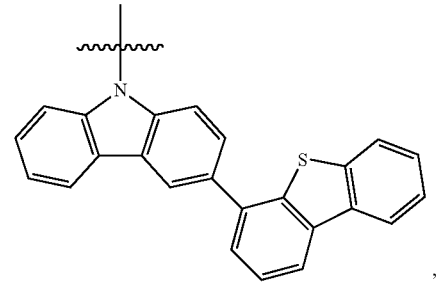
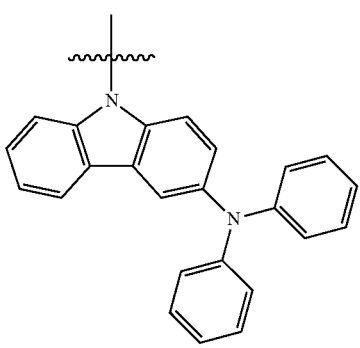

D109
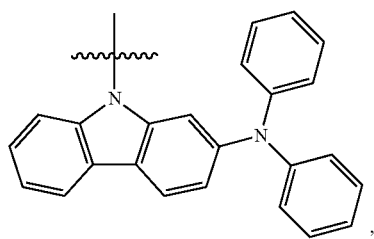
D110
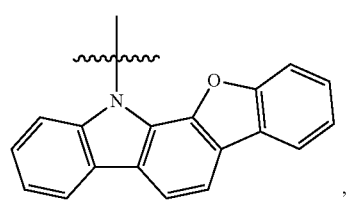
D111
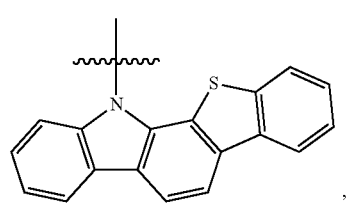
D112
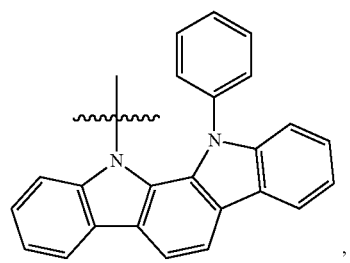
D113
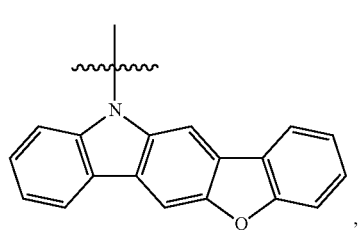
D114
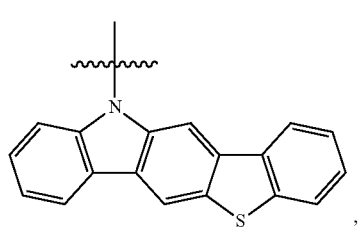
D115
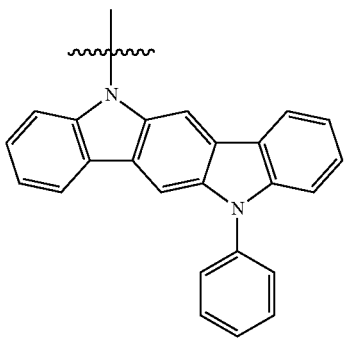
D116
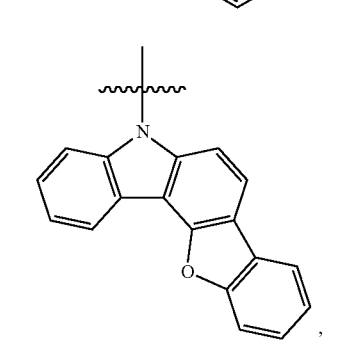
D117
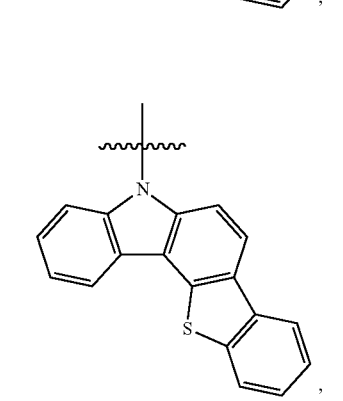
D118
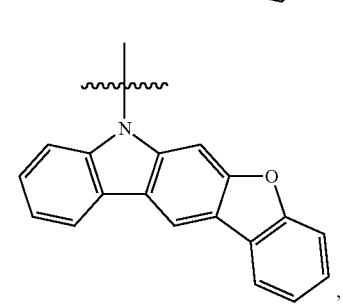
D119
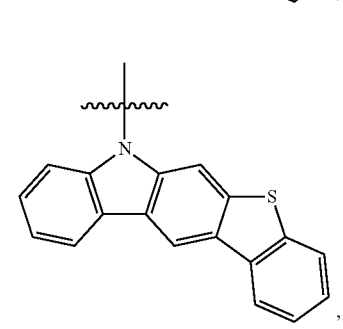

D120
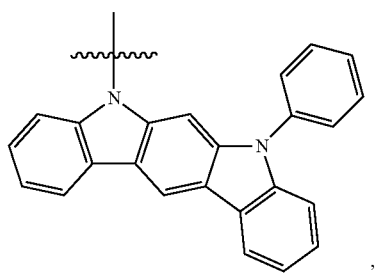
D121
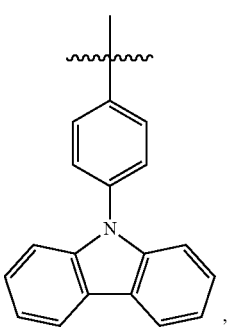
D124
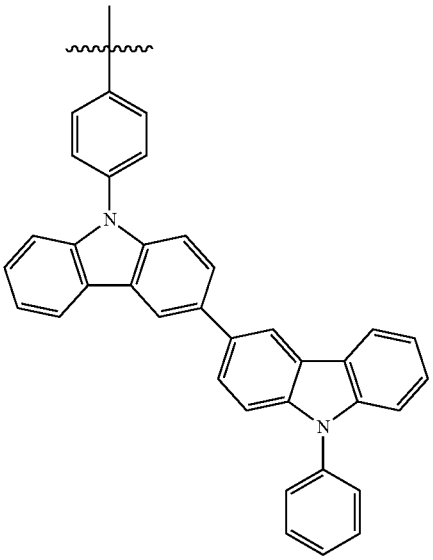
D122
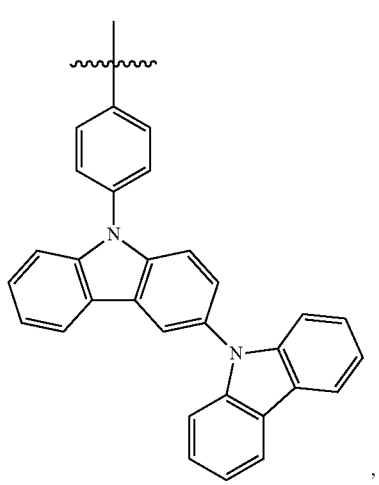
D125
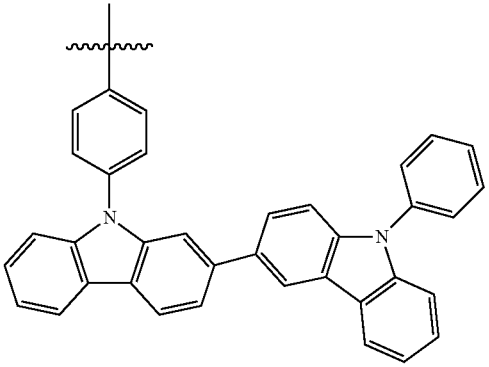
D123
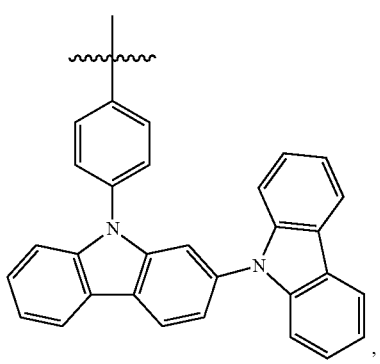
D126
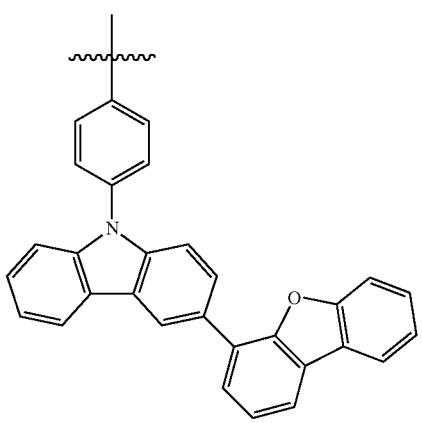

D[127]
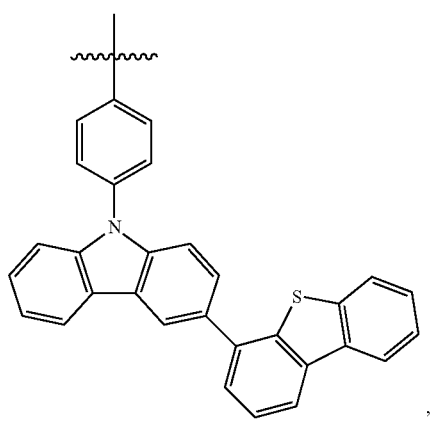
D[128]
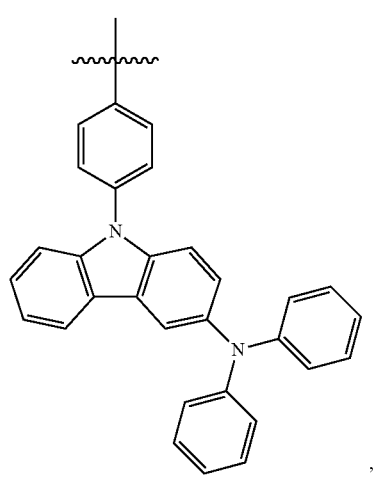
D[129]
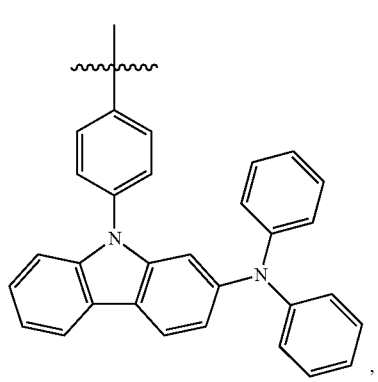
D[130]
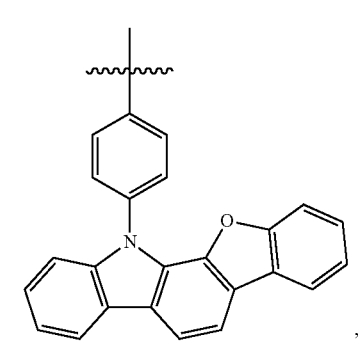
D[131]
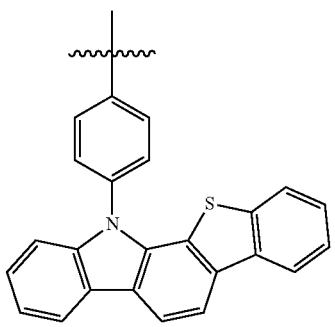
D[132]
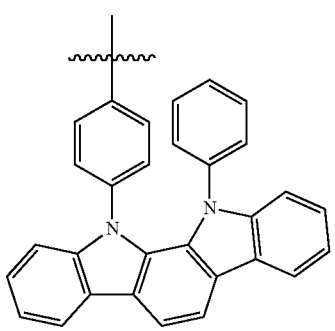
D[133]
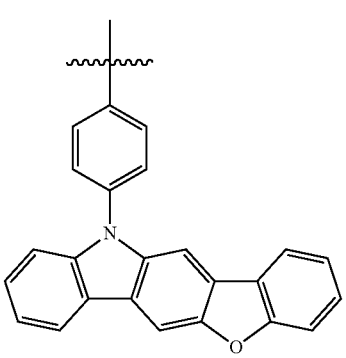
D[134]
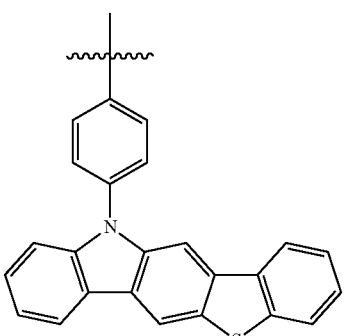

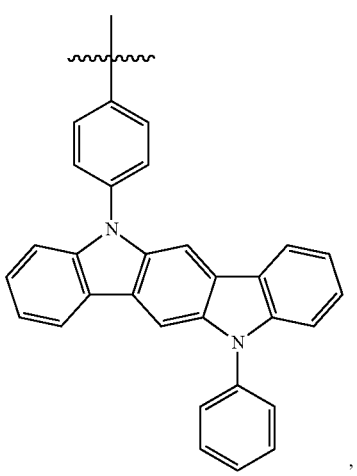
D135,
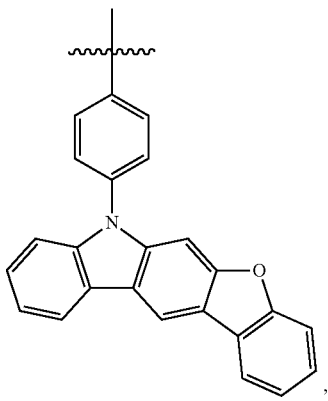
D138,
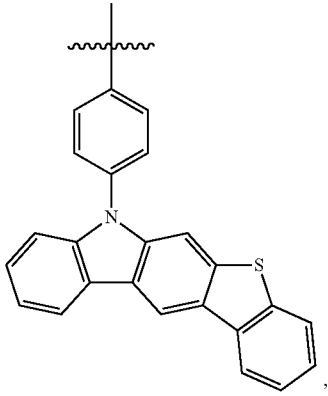
D139,
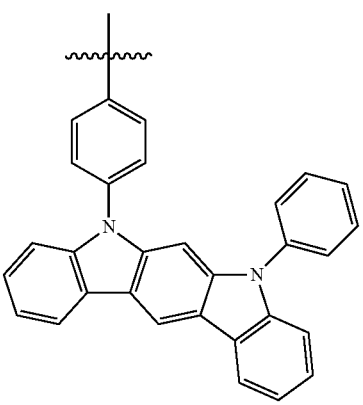
D140,
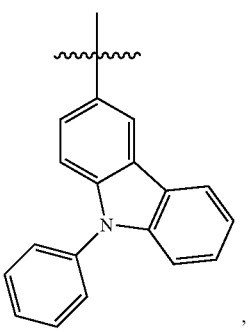
D141,

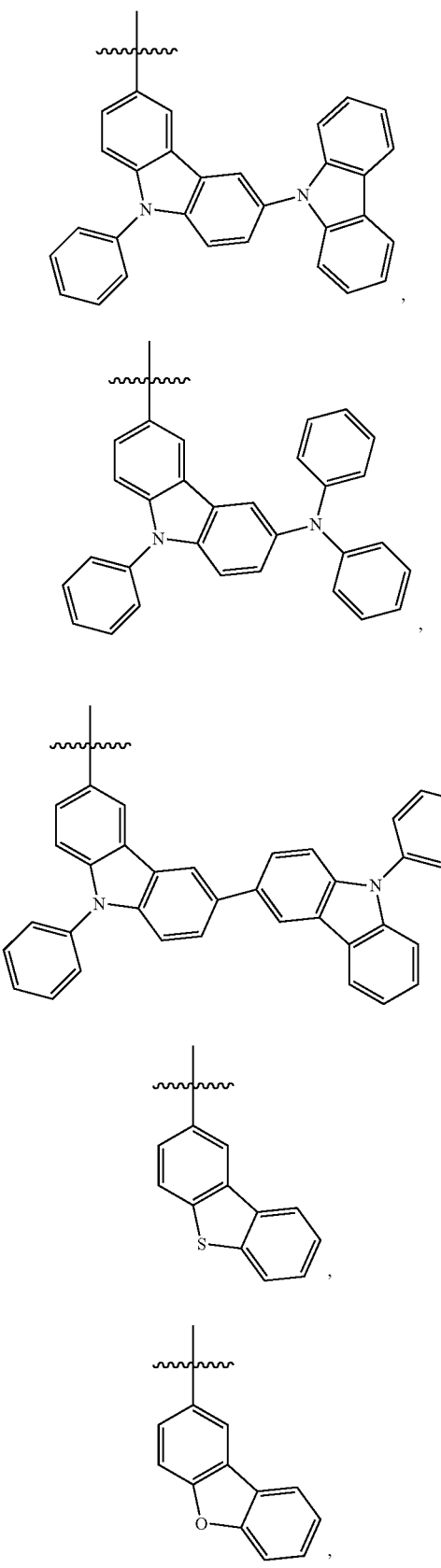
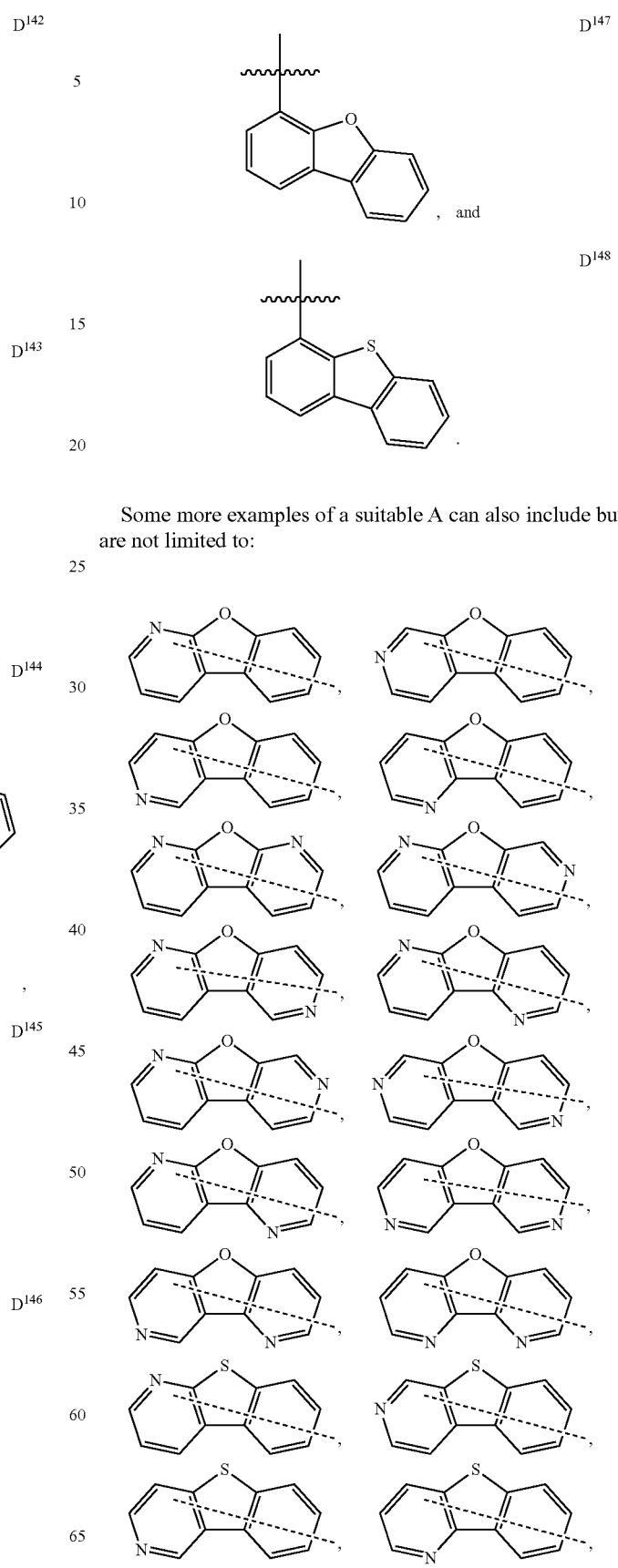
Some more examples of a suitable A can also include but are not limited to:

-continued

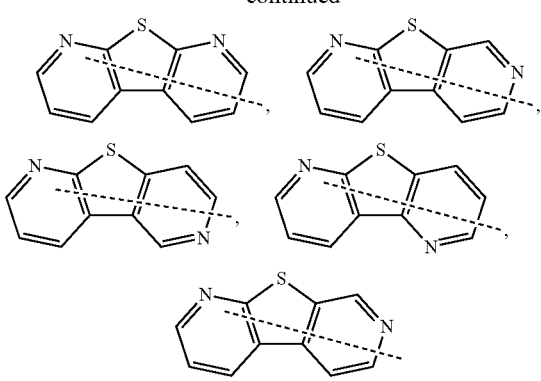

In some embodiments, the compound provided in the present disclosure has a general formula II:

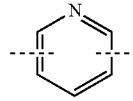

(II)

wherein X is Si or Ge; L comprises a group selected from a group consisting of

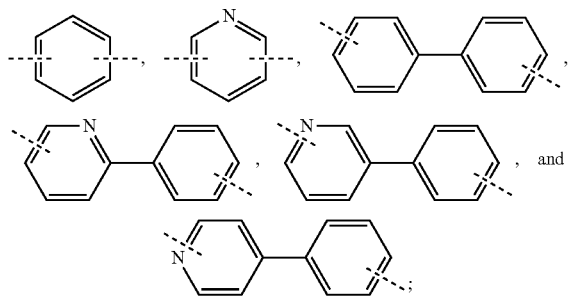

and

A contains a group selected from the group consisting of indole, carbazole, dibenzofuran, dibenzothiophene, triphenylene, azacarbazole, azadibenzofuran, azadibenzothiophene, azadibenzoselenophene and azatriphenylene group. In one embodiment, L comprises a group of benzene

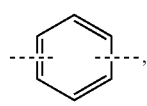

or pyridine

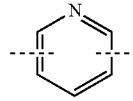

linkers.

Examples of the compound having the formula II include but are not limited to Compound 8 and 10 as shown below:

Compound 8

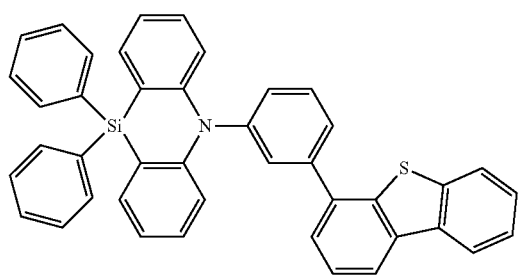

and

Compound 10

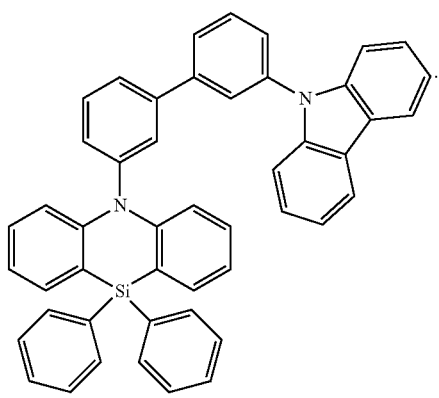

In some embodiments, examples of a suitable exemplary compound having the formula I include but are not limited to the following compounds (Compound 1-Compound 36):

Compound 1

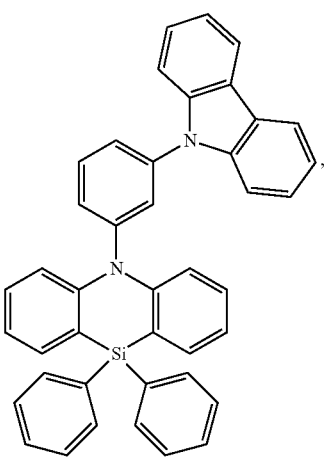

Compound 2
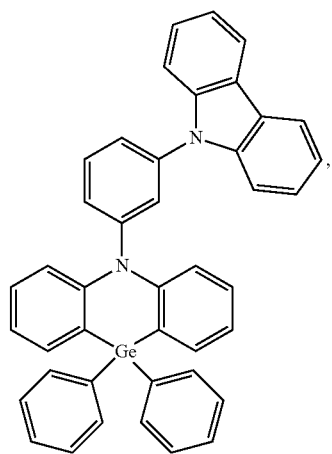
Compound 3
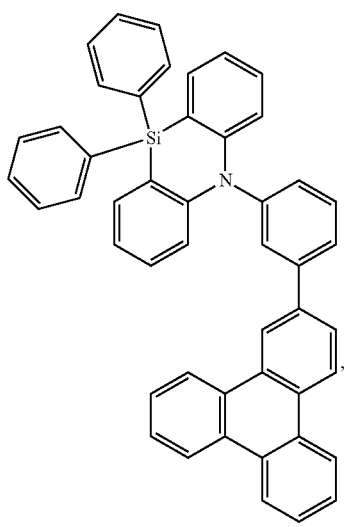
Compound 4
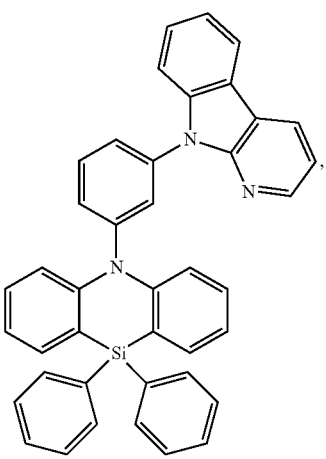
Compound 5
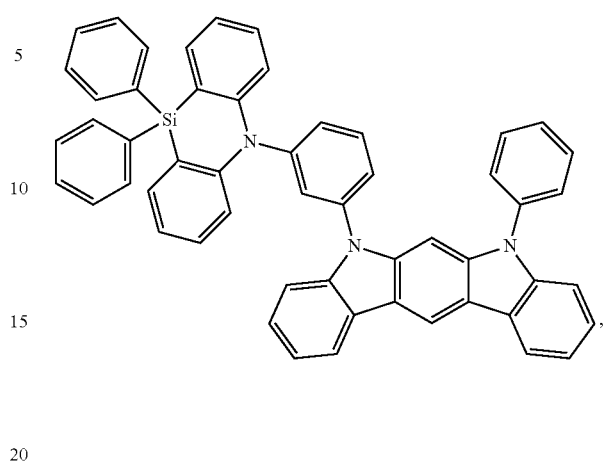
Compound 6
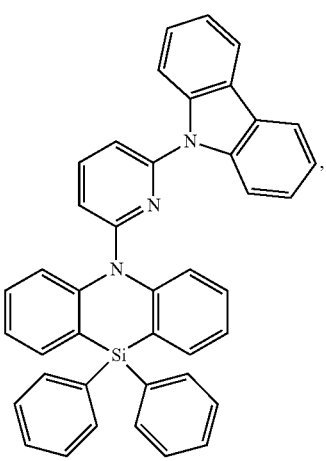
Compound 7

-continued
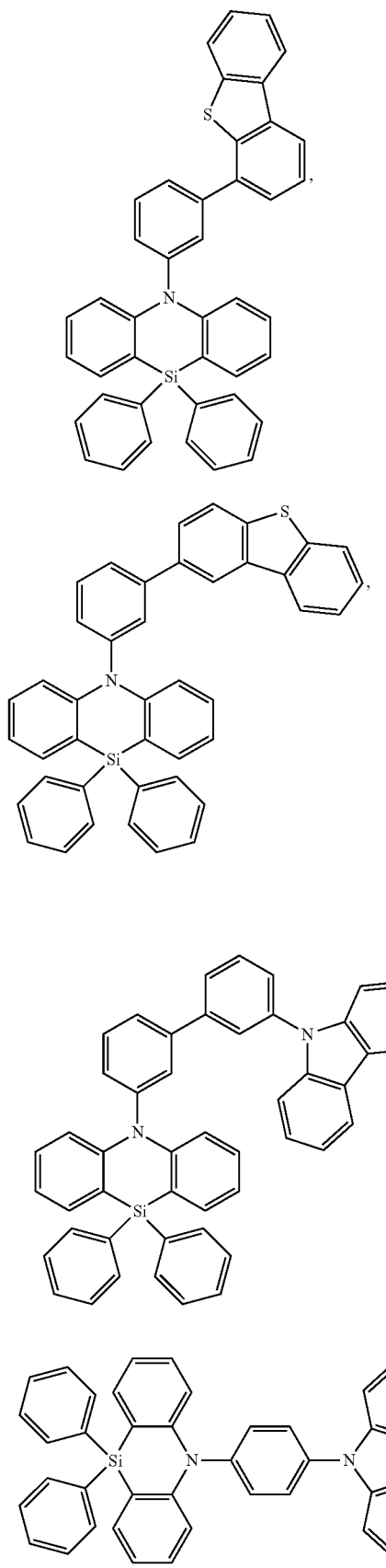
Compound 8
Compound 9
Compound 10
Compound 11
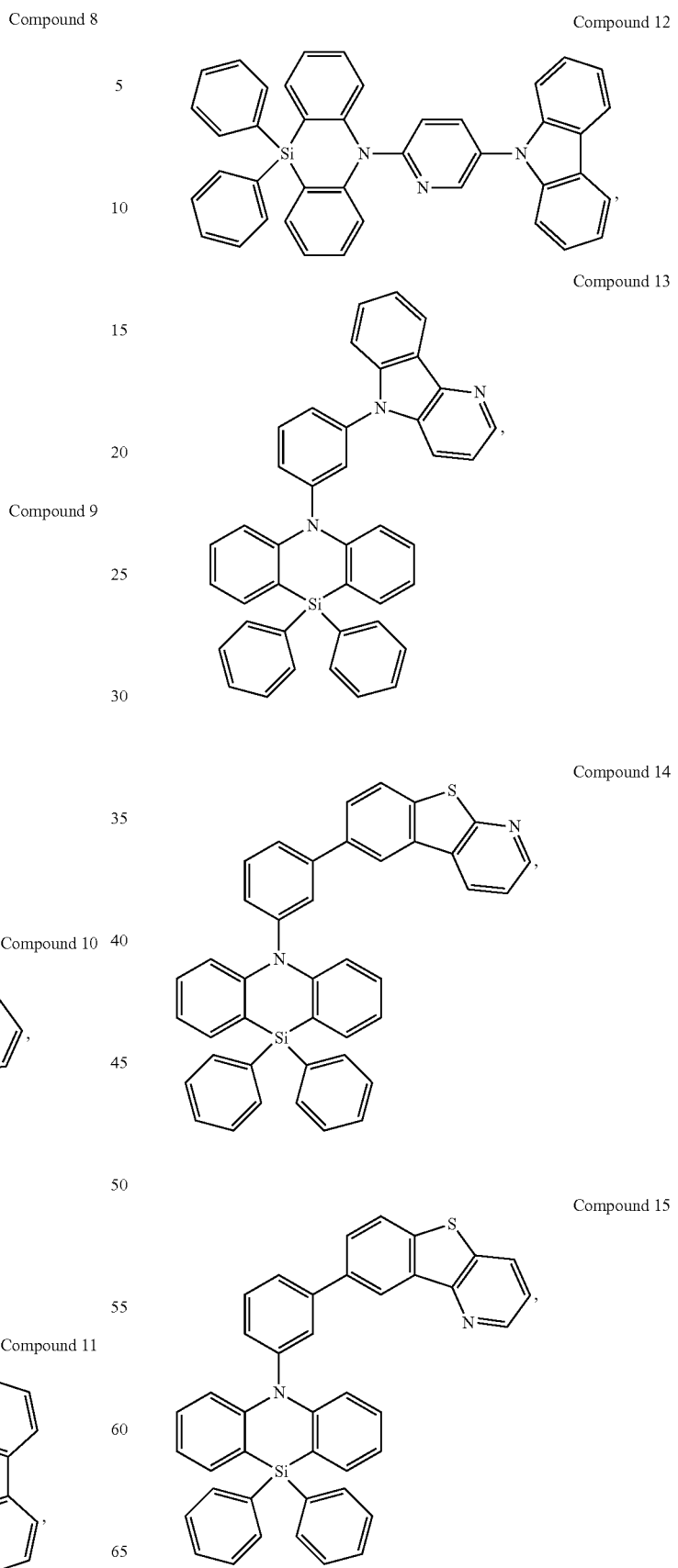
Compound 12
Compound 13
Compound 14
Compound 15

-continued
Compound 16
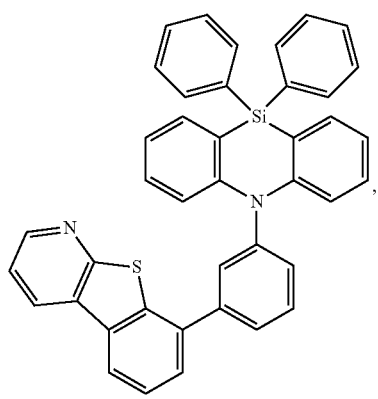
Compound 17
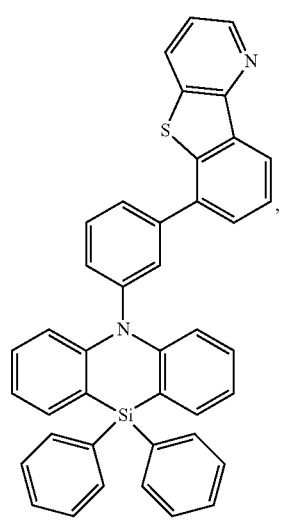
Compound 18
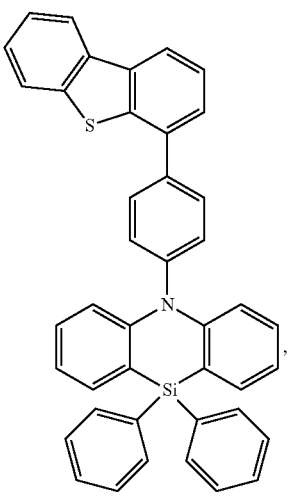
-continued
Compound 19
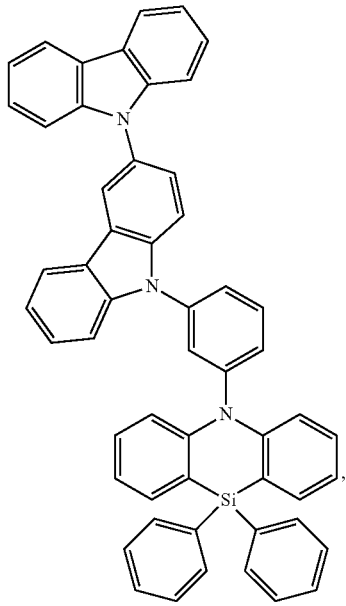
Compound 20
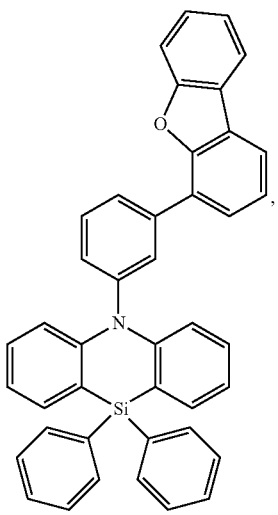
Compound 21
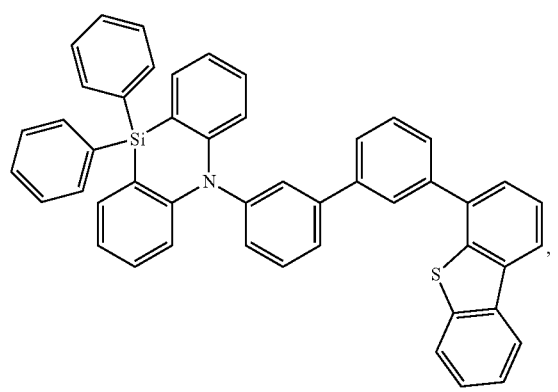

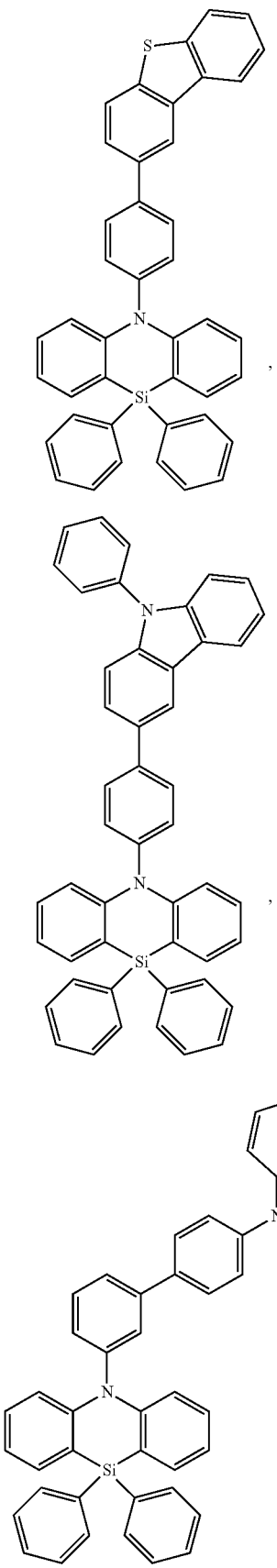
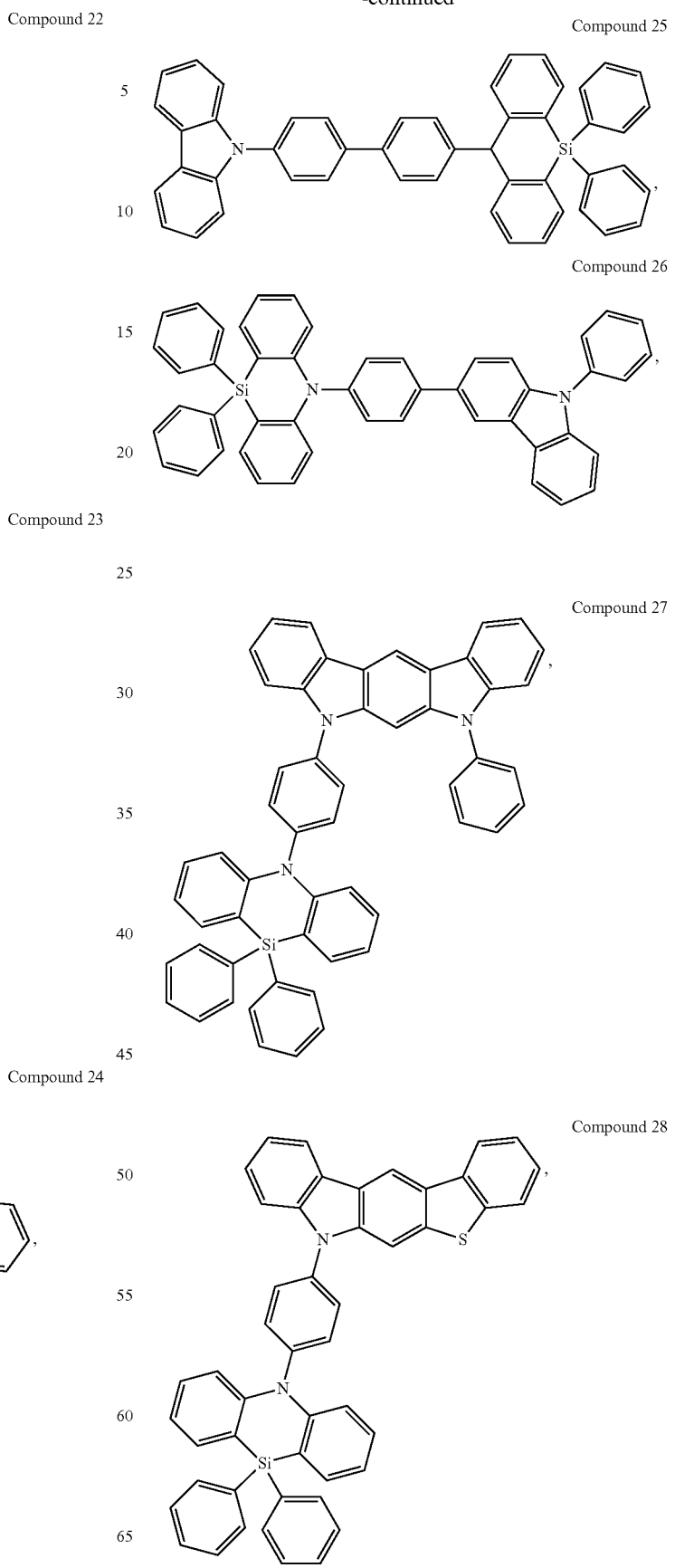

Compound 29
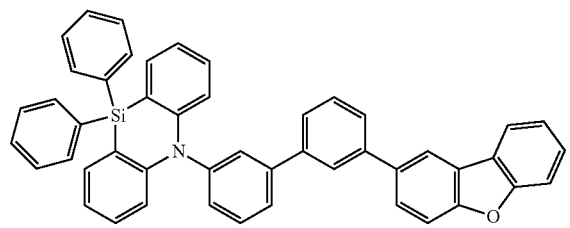
Compound 30
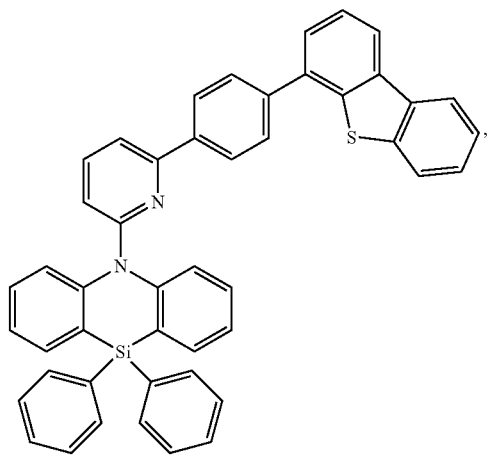
Compound 31
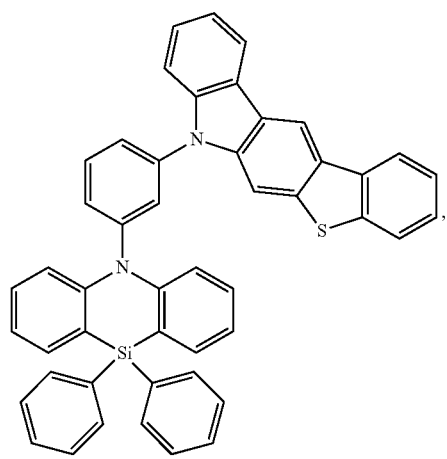
Compound 32
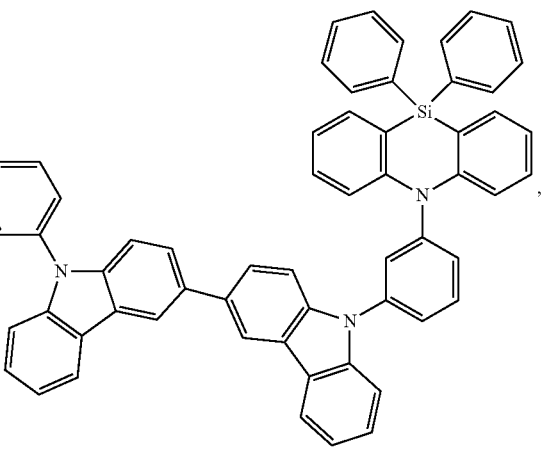
Compound 33
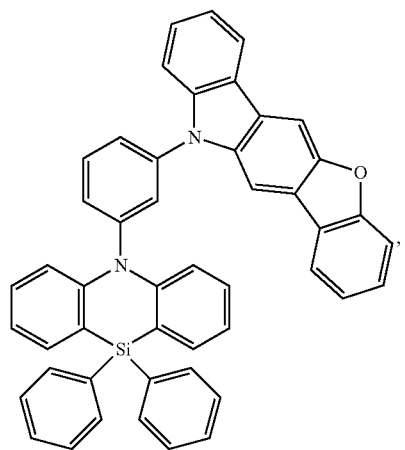
Compound 34
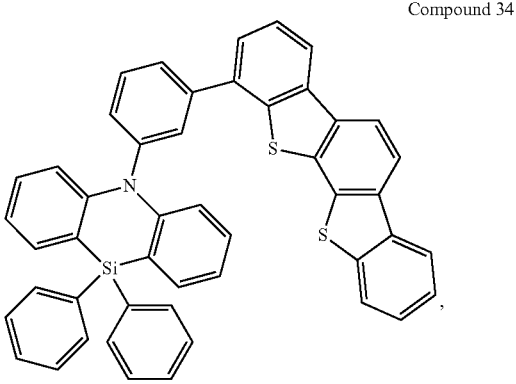

Compound 35

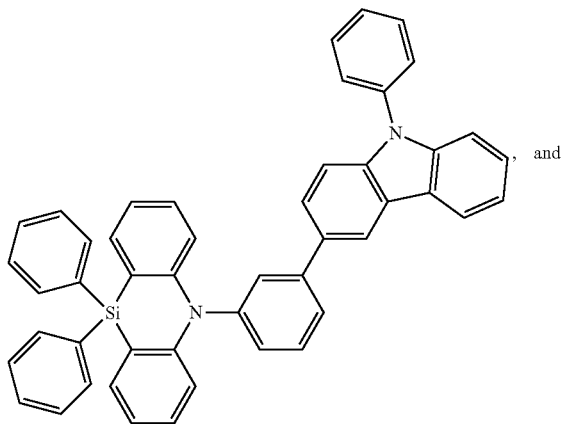

Compound 36

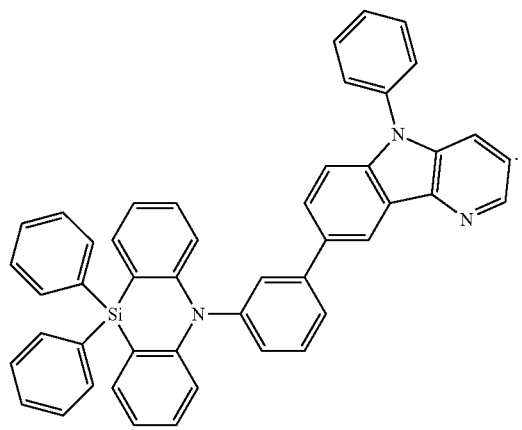

The compound represented by the formula I described above can have either a symmetric or an asymmetric structure containing either dibenzo[b,e][1,4]azasiline or dibenzo[b,e][1,4]azagermine. The compound provides several advantages. For example, the crystallinity of the compound can be easily tuned by modifying a compound having a symmetric structure. The synthesis is also easily performed with diphenylsilane or germane, which can also improve the glass transition temperature ($T_g$) of the compound. In some embodiments, the ring structure dibenzo[b,e][1,4]azasiline or azagermine can maintain a similar triplet energy compared to the carbazole moiety while adding additional conjugated rings. The additional conjugated rings can increase the glass transition temperature of the resulting compound. In some embodiments, the benzene or pyridine linker (in L) between the two functional groups can also increase the $T_g$ of the compound. In some embodiments, a meta substitution of A on the benzene or pyridine linker allows to maintain a very high triplet energy for blue OLED applications with reduced quenching.

Additional advantage of the compound having the formula I results from an asymmetric structure in some embodiments. The asymmetric structure allows to fine-tune the HOMO/LUMO energy level, and modify the hole and electron transporting properties. For example, the hole and electron transporting properties can be modified by changing the functional group (such as $R^1$ and $R^2$) at the other end of the dibenzo[b,e][1,4]azasiline or azagermine. Using different functional groups, the compound having the formula I can be tailored as a host material in green and red devices.

In addition, the compound provided in this disclosure can be also very soluble in organic solvents such as toluene and xylene. Solution process can be used to fabricate high performance PHOLED, for example, for low-cost lighting applications.

A composition comprising a compound having the formula I described above is also provided in the present disclosure. A compound of the formula I can be formulated with any other material suitable for organic light emitting applications. Examples of any other suitable materials include but are not limited to a host compound, a phosphorescent dopant, a blocking material, an electron transporting material, an additive, and any combination thereof. Examples of an exemplary compound of the formula I can have a general structure as described in any of the formulas I-II. Examples of a suitable exemplary compound include but are not limited to Compound 1-Compound 36 described above.

According to another embodiment of the present disclosure, a first device comprising an organic light-emitting device is provided. The first device comprises an anode, a cathode, and an organic layer. The organic layer is disposed between the anode and the cathode, and comprises a compound having the formula I or a composition comprising a compound having the formula I.

The compound can be used alone or in combination with other materials in the organic layer for different functions. For example, in some embodiments, the organic layer is an emissive layer and the compound of the formula I is a host material. The organic layer may further comprise an emissive dopant. The compound of the formula I can be also used as a blocking material or an electron transporting material. The first device can be a consumer product, an organic light-emitting device, and/or a lighting panel.

In some embodiments, the compounds provided in the present disclosure give good results in PHOLEDs for all colors, particularly for blue emitters.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

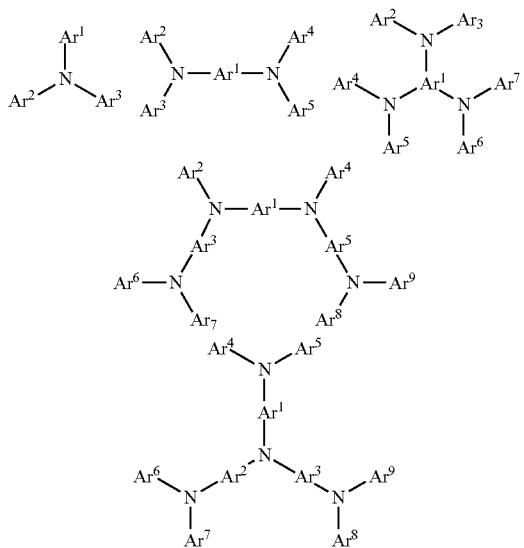

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof In one aspect, $Ar^1$ to $Ar^9$ is independently selected from the group consisting of:

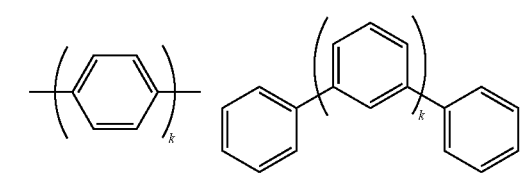

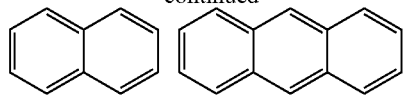

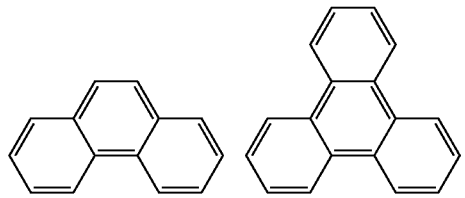

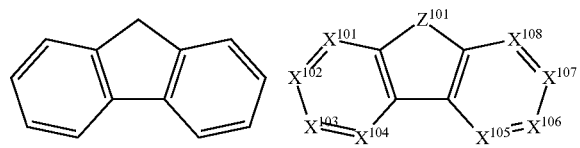

where k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

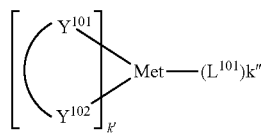

where Met is a metal; ($Y^{101}$—$Y^{102}$) is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, ($Y^{101}$—$Y^{102}$) is a 2-phenylpyridine derivative.

In another aspect, ($Y^{101}$—$Y^{102}$) is a carbene ligand.

In another aspect, Met is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While Table 1 below categorizes host materials as preferred for devices that emit various colors, any host material may be used with any dopant so long as the triplet criterion is satisfied.

Examples of metal complexes used as host are preferred to have the following general formula:

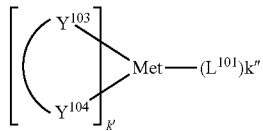

where Met is a metal; ($Y^{103}$—$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

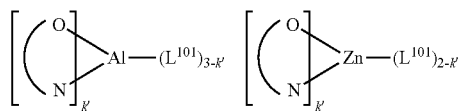

where (O—N) is a bidentate ligand, having metal coordinated to atoms O and N.

In another aspect, Met is selected from Ir and Pt.

In a further aspect, ($Y^{103}$—$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof In one aspect, host compound contains at least one of the following groups in the molecule:

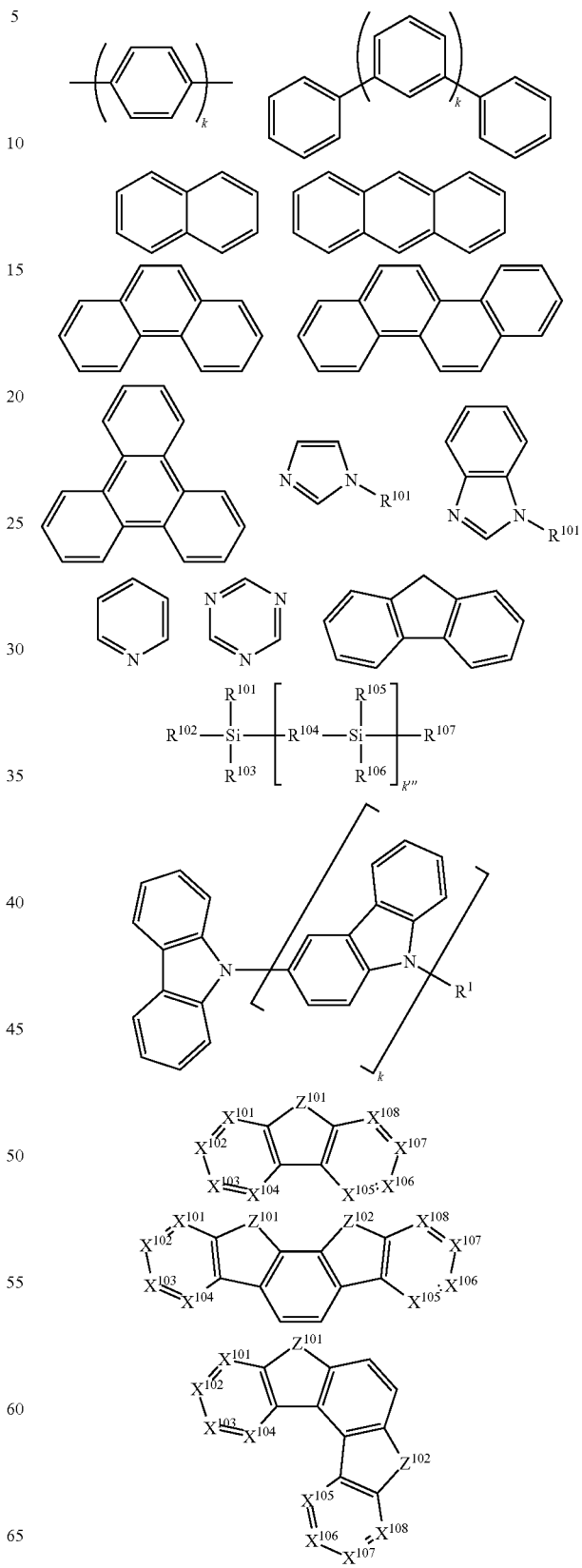

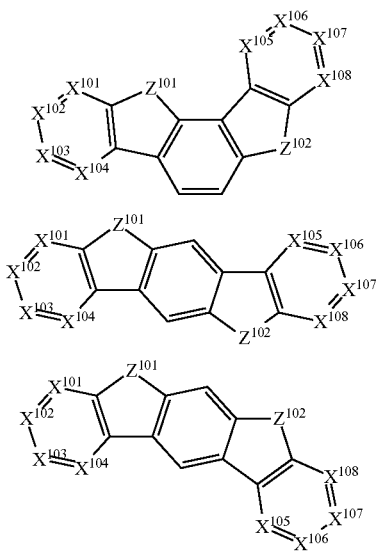

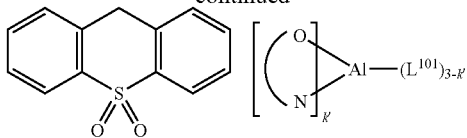

where k is an integer from 1 to 20, $L^{101}$ is another ligand, and k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

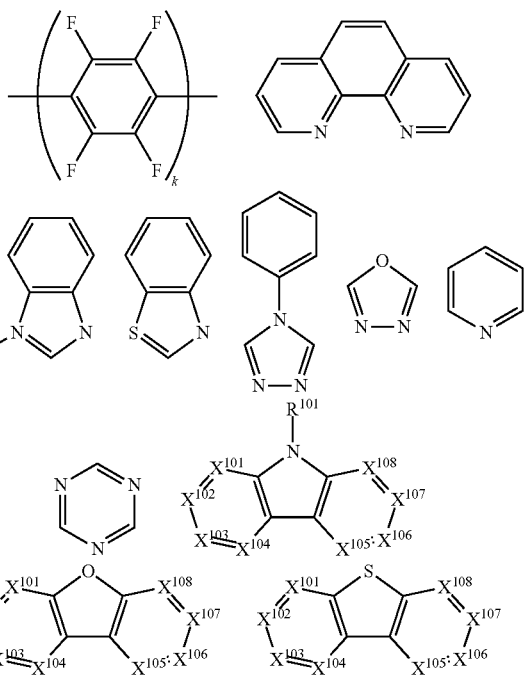

where $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 1 to 20. k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

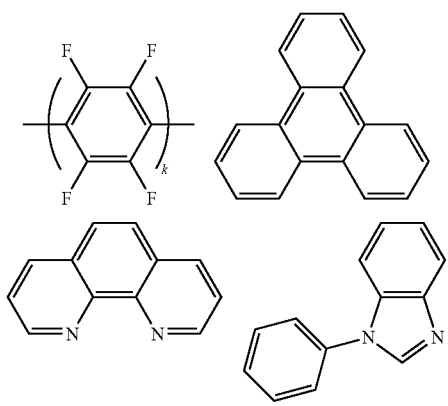

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

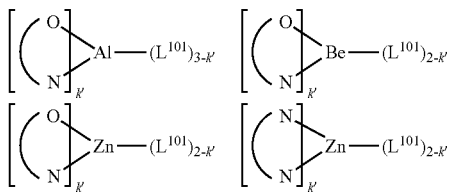

where (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | [Cu phthalocyanine structure] | Appl. Phys. Lett. 69, 2160 (1996) |
| Starburst triarylamines | [starburst triarylamine structure] | J. Lumin. 72-74, 985 (1997) |
| $CF_x$ Fluorohydrocarbon polymer | $-[CH_xF_y]_n-$ | Appl. Phys. Lett. 78, 673 (2001) |

TABLE 1-continued
| MATERIAL | EXAMPLES OF MATERIAL | PUBLICATIONS |
| --- | --- | --- |
| Conducting polymers (e.g., PEDOT:PSS, polyaniline, polypthiophene) | 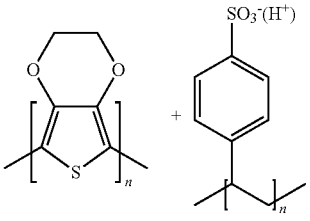 | Synth. Met. 87, 171 (1997) WO2007002683 |
| Phosphonic acid and sliane SAMs | 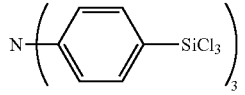 | US20030162053 |
| Triarylamine or polythiophene polymers with conductivity dopants | 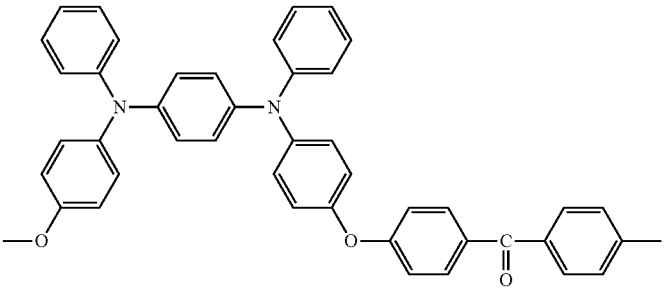 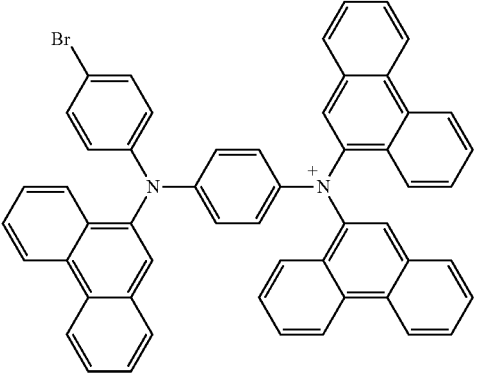 [SMILES: Brc1ccc(N(c2ccc(N(c3cc4ccccc4c4ccccc34)c3cc4ccccc4c4ccccc34)cc2)c2cc3ccccc3c3ccccc23)cc1] 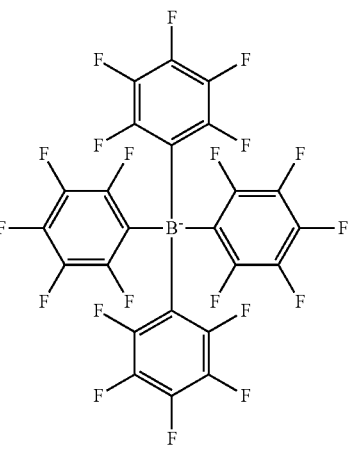 and | EP1725079A1 |

TABLE 1-continued
| MATERIAL | EXAMPLES OF MATERIAL | PUBLICATIONS |
| --- | --- | --- |
| Organic compounds with conductive inorganic compounds, such as molybdenum and tungsten oxides | 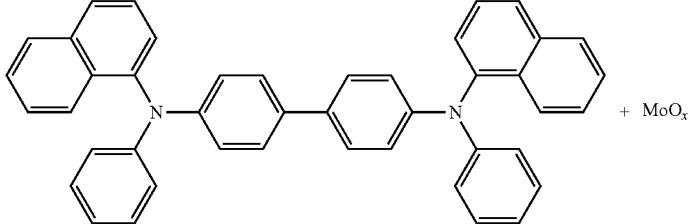 [SMILES: c1ccc(N(c2ccc(-c3ccc(N(c4ccccc4)c4cccc5ccccc45)cc3)cc2)c2cccc3ccccc23)cc1] | US20050123751<br>SID Symposium Digest, 37, 923 (2006)<br>WO2009018009 |
| n-type semiconducting organic complexes | 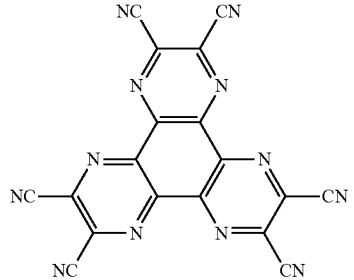 [SMILES: N#Cc1nc2c3nc(C#N)c(C#N)nc3c3nc(C#N)c(C#N)nc3c2nc1C#N] | US20020158242 |
| Metal organometallic complexes | 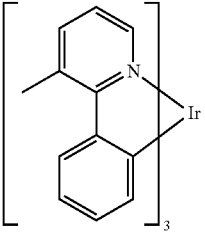 | US20060240279 |
| Cross-linkable compounds | 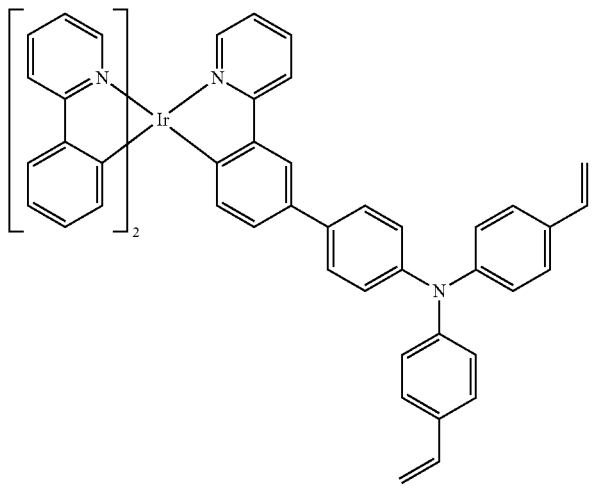 | US20080220265 |

TABLE 1-continued
| MATERIAL | EXAMPLES OF MATERIAL | PUBLICATIONS |
|---|---|---|
| Polythiophene based polymers and copolymers | 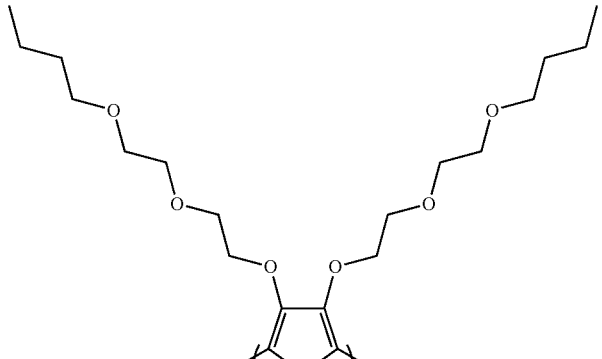 | WO 2011075644<br>EP2350216 |
| Hole transporting materials | | |
| Triarylamines (e.g., TPD, -NPD) | 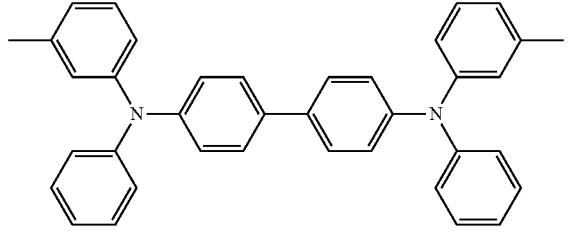 | Appl. Phys. Lett. 51, 913 (1987) |
| | 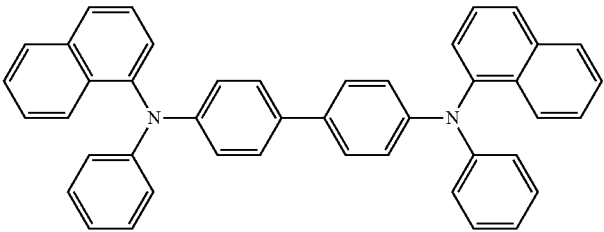 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 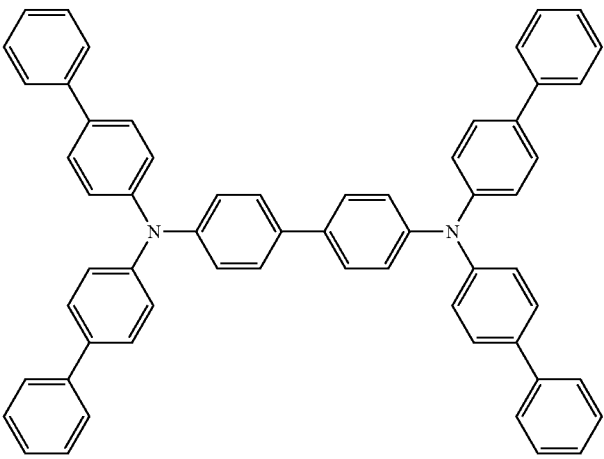 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 1-continued
| MATERIAL | EXAMPLES OF MATERIAL | PUBLICATIONS |
|---|---|---|
| | 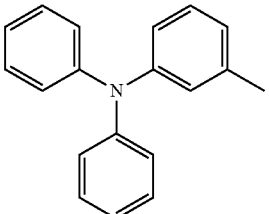 | J. Mater. Chem. 3, 319 (1993) |
| | 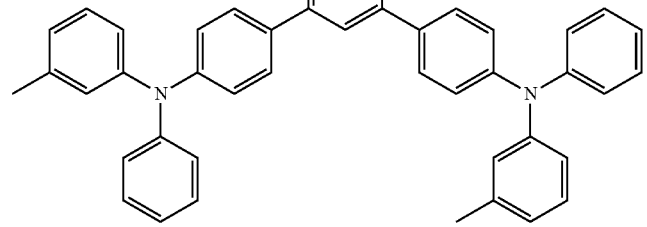 | Appl. Phys. Lett. 90, 183503 (2007) |
| | 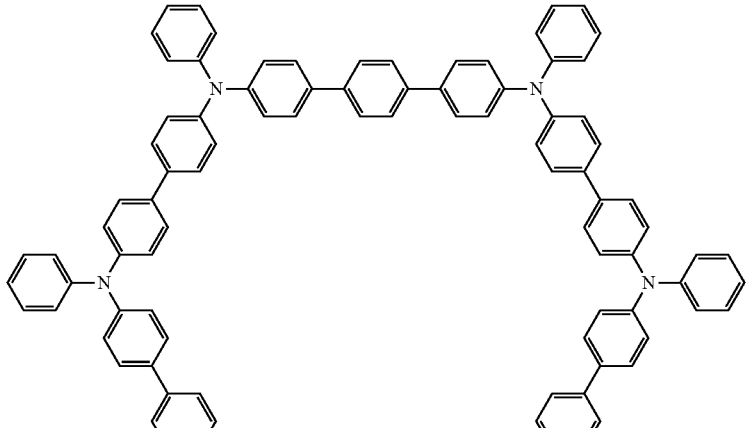 | Appl. Phys. Lett. 90, 183503 (2007) |
| Triaylamine on spirofluorene core | 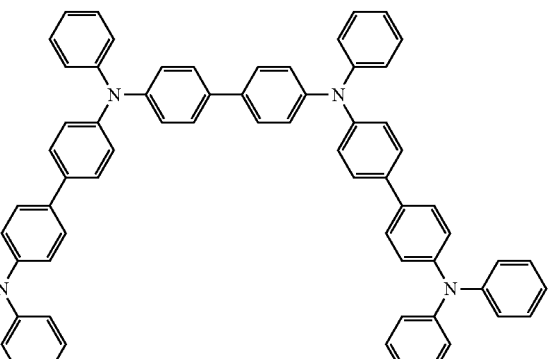 | Synth. Met. 91, 209 (1997) |

TABLE 1-continued

| MATERIAL | EXAMPLES OF MATERIAL | PUBLICATIONS |
|---|---|---|
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |
| Isoindole compounds | | Chem. Mater. 15, 3148 (2003) |

TABLE 1-continued
| MATERIAL | EXAMPLES OF MATERIAL | PUBLICATIONS |
|---|---|---|
| Metal carbene complexes | 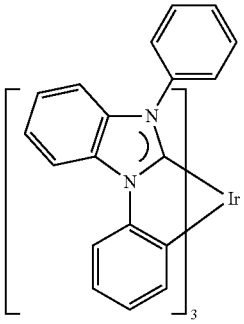 | US20080018221 |
Phosphorescent OLED host materials
Red hosts
| | | |
|---|---|---|
| Arylcarbazoles | 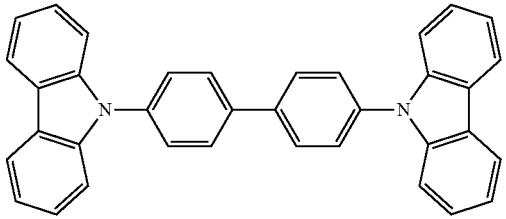 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 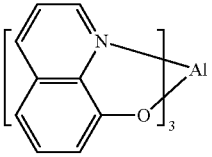 | Nature 395, 151 (1998) |
| | 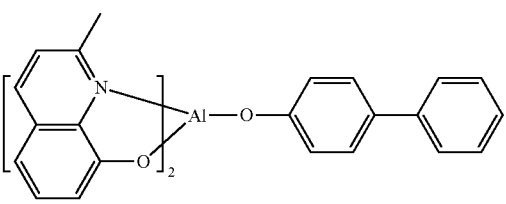 | US20060202194 |
| | 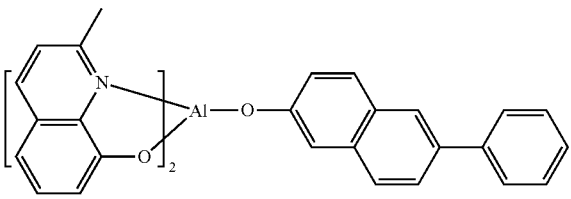 | WO2005014551 |
| | 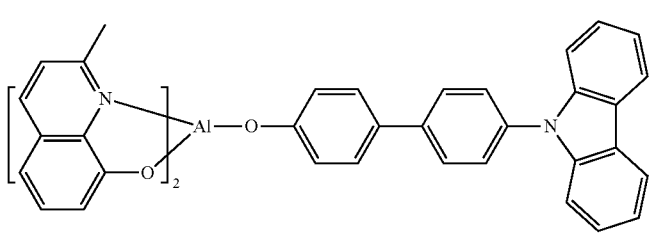 | WO2006072002 |

TABLE 1-continued

| MATERIAL | EXAMPLES OF MATERIAL | PUBLICATIONS |
| --- | --- | --- |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |

TABLE 1-continued
| MATERIAL | EXAMPLES OF MATERIAL | PUBLICATIONS |
|---|---|---|
| | 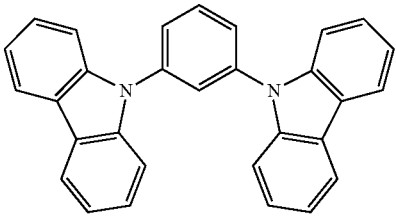 [SMILES: c1cc(-n2c3ccccc3c3ccccc32)cc(-n2c3ccccc3c3ccccc32)c1] | US20030175553 |
| | 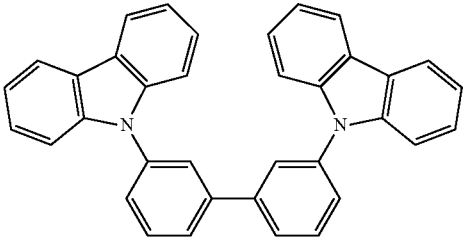 [SMILES: c1cc(-c2cccc(-n3c4ccccc4c4ccccc43)c2)cc(-n2c3ccccc3c3ccccc32)c1] | WO2001039234 |
| Aryltriphenylene compounds | 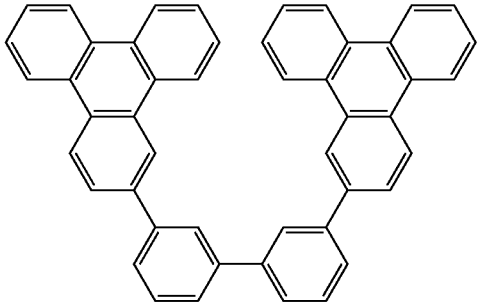 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 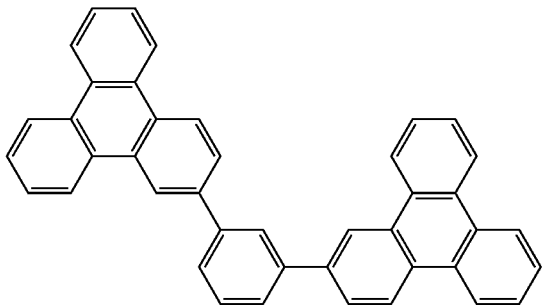 [SMILES: c1cc(-c2ccc3c4ccccc4c4ccccc4c3c2)cc(-c2ccc3c4ccccc4c4ccccc4c3c2)c1] | US20060280965 |
| | 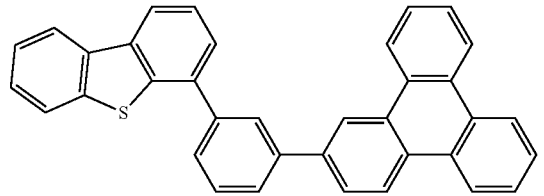 [SMILES: c1cc(-c2ccc3c4ccccc4c4ccccc4c3c2)cc(-c2cccc3c2sc2ccccc23)c1] | WO2009021126 |

TABLE 1-continued
| MATERIAL | EXAMPLES OF MATERIAL | PUBLICATIONS |
|---|---|---|
| Poly-fused heteroaryl compounds | 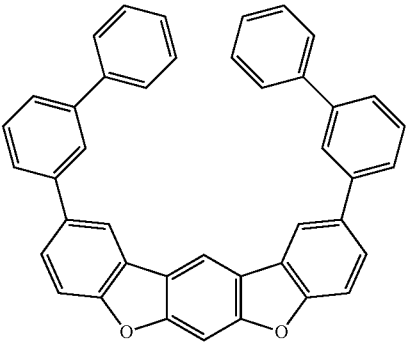 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 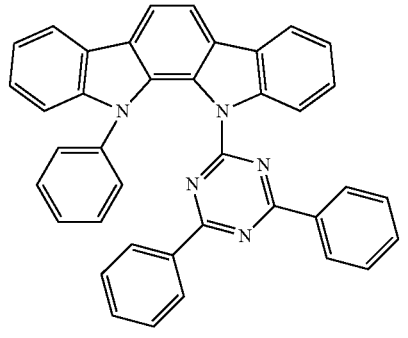 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 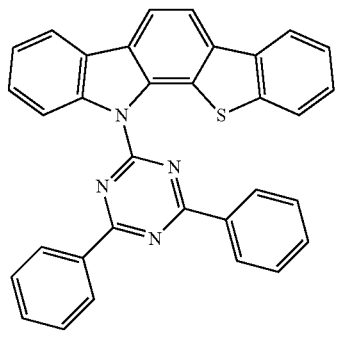 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 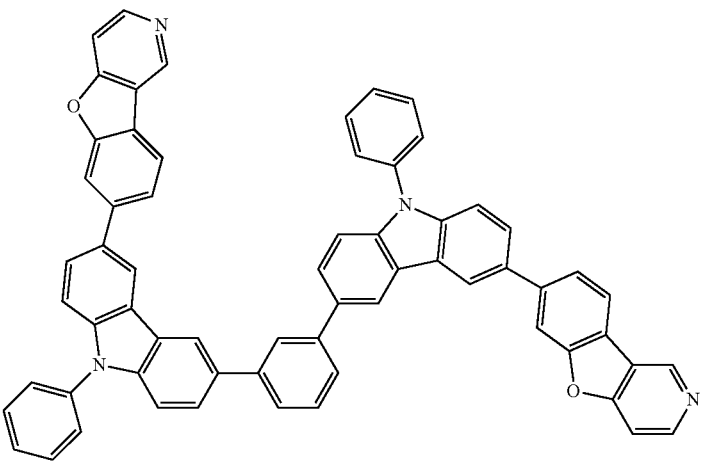 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 1-continued
| MATERIAL | EXAMPLES OF MATERIAL | PUBLICATIONS |
|---|---|---|
| | 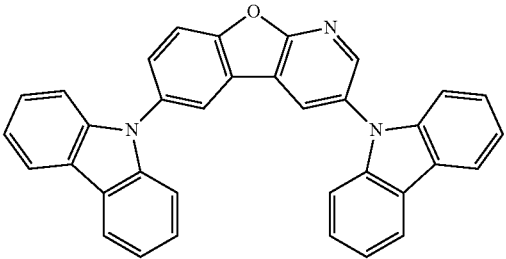 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 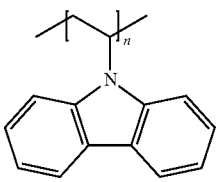 | Appl. Phys. Lett, 77, 2280 (2000) |
| Spirofluorene compounds | 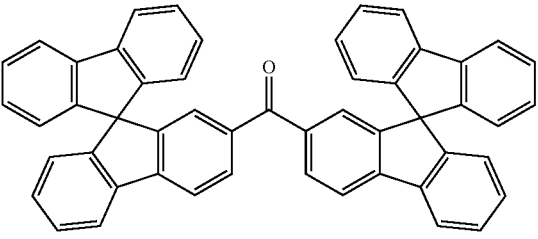 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 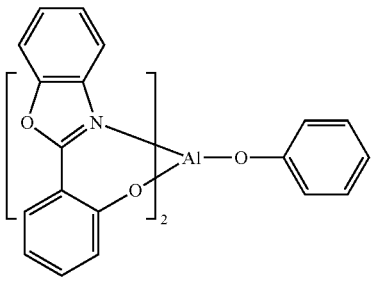 | WO2005089025 |
| | 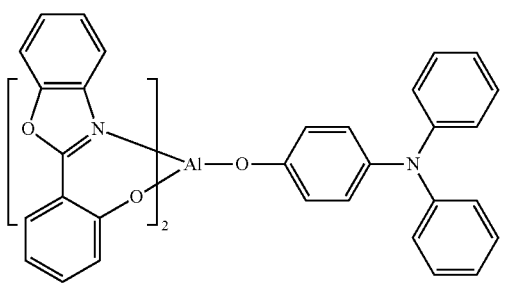 | WO2006132173 |
| | 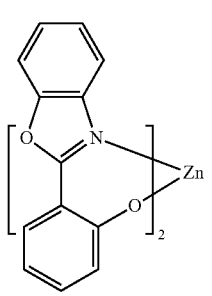 | JP200511610 |

TABLE 1-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |

TABLE 1-continued

| MATERIAL | EXAMPLES OF MATERIAL | PUBLICATIONS |
|---|---|---|
| | | WO2004107822 |
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |

TABLE 1-continued

| MATERIAL | EXAMPLES OF MATERIAL | PUBLICATIONS |
|---|---|---|
| | | US20070190359 |
| Dibenzothiophene/ Dibenzofuran-carbazole compounds | | WO2006114966, US20090167162 |
| | | US20090167162 |
| | | WO2009086028 |
| | | US20090030202, US20090017330 |
| | | US20100084966 |

TABLE 1-continued
| MATERIAL | EXAMPLES OF MATERIAL | PUBLICATIONS |
|---|---|---|
| Silicon aryl compounds | 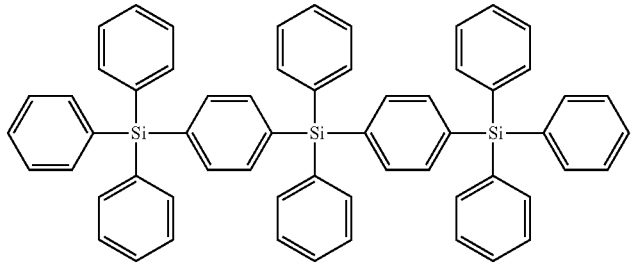 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
|  | 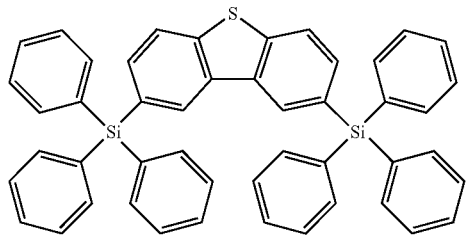 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 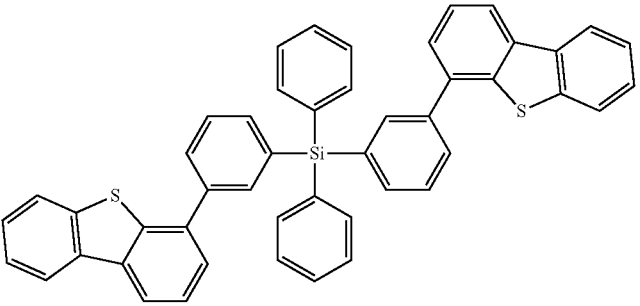 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 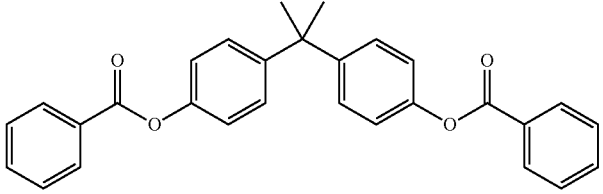 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 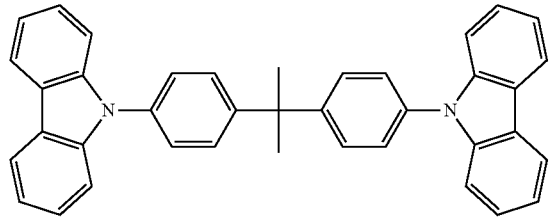 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 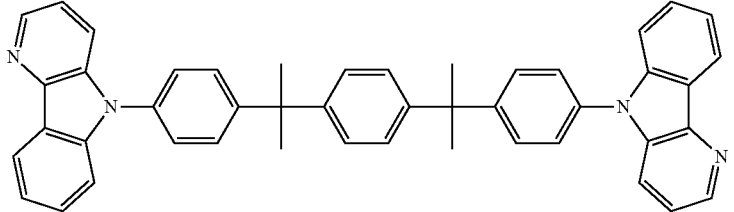 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 1-continued
| MATERIAL | EXAMPLES OF MATERIAL | PUBLICATIONS |
|---|---|---|
| High triplet metal organometallic complex | 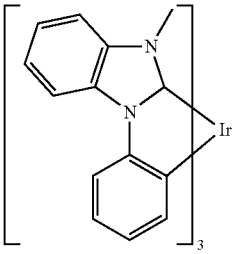 | U.S. Pat. No. 7,154,114 |
Phosphorescent dopants
Red dopants
| Heavy metal porphyrins (e.g., PtOEP) | 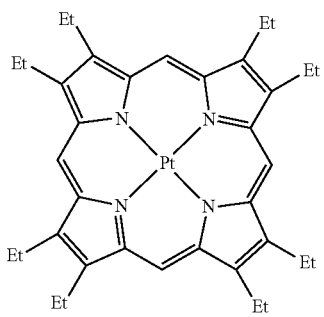 | Nature 395, 151 (1998) |
| Iridium(III) organometallic complexes | 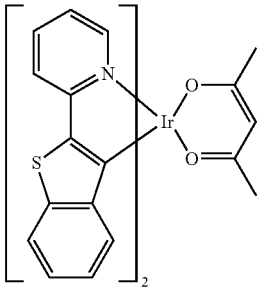 | Appl. Phys. Lett. 78, 1622 (2001) |
| | 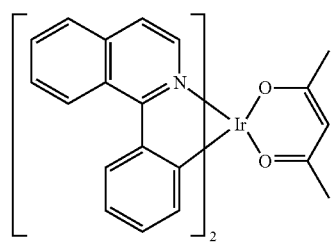 | US2006835469 |
| | 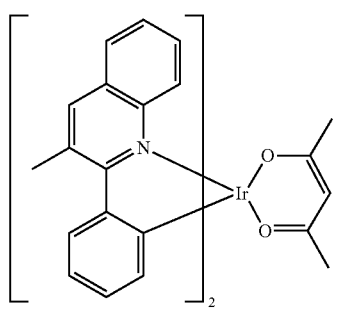 | US2006835469 |

TABLE 1-continued

| MATERIAL | EXAMPLES OF MATERIAL | PUBLICATIONS |
|---|---|---|
| | | US20060202194 |
| | | US20060202194 |
| | | US20070087321 |
| | | US20080261076<br>US20100090591 |
| | | US20070087321 |

TABLE 1-continued

| MATERIAL | EXAMPLES OF MATERIAL | PUBLICATIONS |
|---|---|---|
| | | Adv. Mater. 19, 739 (2007) |
| | | WO2009100991 |
| | | WO2008101842 |
| | | U.S. Pat. No. 7,232,618 |
| Platinum(II) organometallic complexes | | WO2003040257 |

TABLE 1-continued
| MATERIAL | EXAMPLES OF MATERIAL | PUBLICATIONS |
|---|---|---|
| | 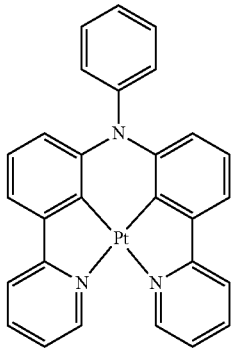 | US20070103060 |
| Osminum(III) complexes | 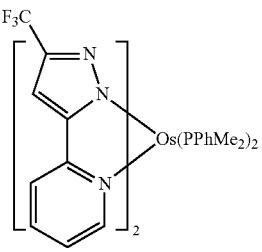 | Chem. Mater. 17, 3532 (2005) |
| Ruthenium(II) complexes | 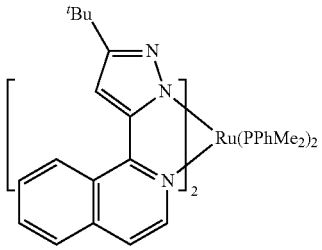 | Adv. Mater. 17, 1059 (2005) |
| Rhenium (I), (II), and (III) complexes | 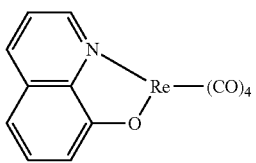 | US20050244673 |
Green dopants
| Iridium(III) organometallic complexes | 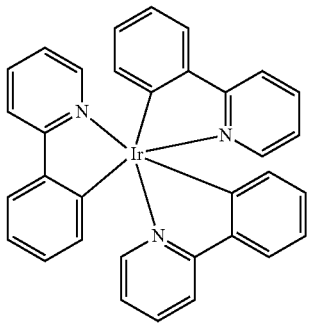 and its derivatives | Inorg. Chem. 40, 1704 (2001) |

TABLE 1-continued
| MATERIAL | EXAMPLES OF MATERIAL | PUBLICATIONS |
|---|---|---|
| | 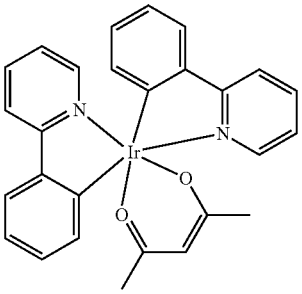 | US20020034656 |
| | 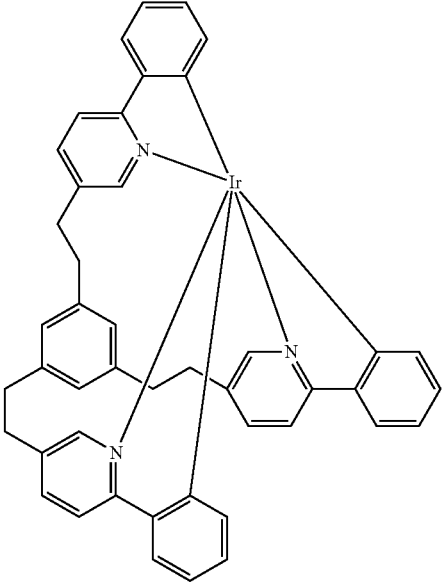 | U.S. Pat. No. 7,332,232 |
| | 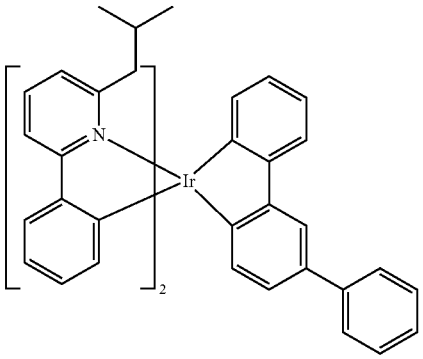 | US20090108737 |
| | 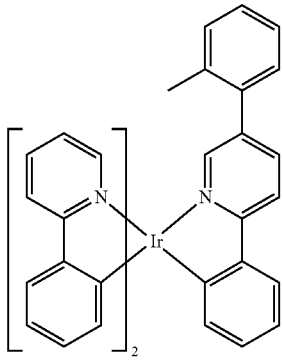 | WO2010028151 |

TABLE 1-continued
| MATERIAL | EXAMPLES OF MATERIAL | PUBLICATIONS |
|---|---|---|
| | 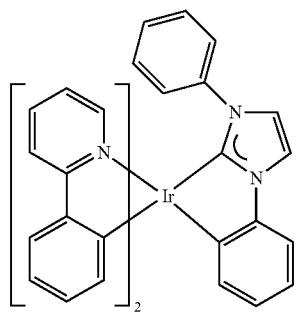 | EP1841834B |
| | 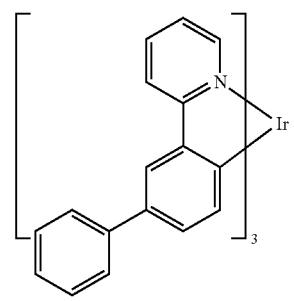 | US20060127696 |
| | 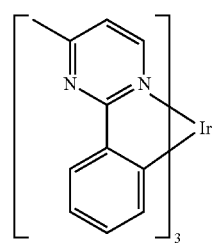 | US20090039776 |
| | 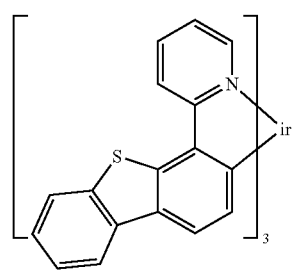 | U.S. Pat. No. 6,921,915 |
| | 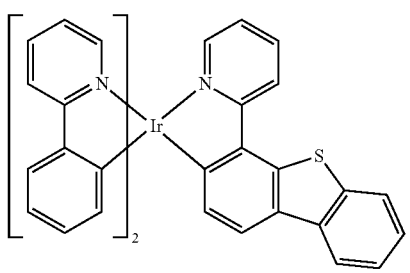 | US20100244004 |

TABLE 1-continued
| MATERIAL | EXAMPLES OF MATERIAL | PUBLICATIONS |
|---|---|---|
| | 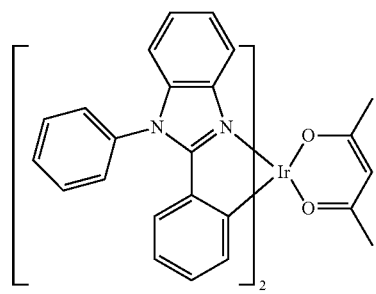 | U.S. Pat. No. 6,687,266 |
| | 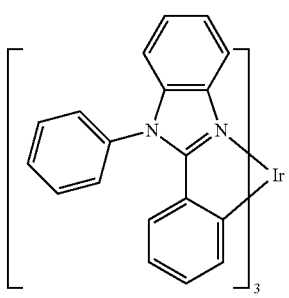 | Chem. Mater. 16, 2480 (2004) |
| | 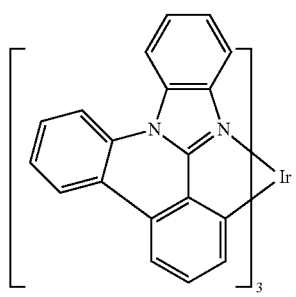 | US20070190359 |
| | 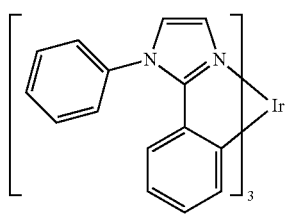 | US20060008670<br>JP2007123392 |
| | 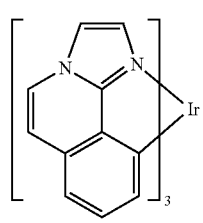 | WO2010086089,<br>WO2011044988 |
| | 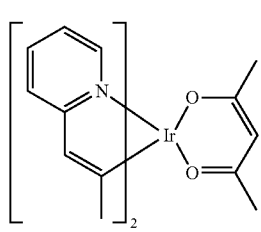 | Adv. Mater. 16, 2003 (2004) |

TABLE 1-continued

| MATERIAL | EXAMPLES OF MATERIAL | PUBLICATIONS |
| --- | --- | --- |
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 1-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 1-continued
| MATERIAL | EXAMPLES OF MATERIAL | PUBLICATIONS |
|---|---|---|
| | 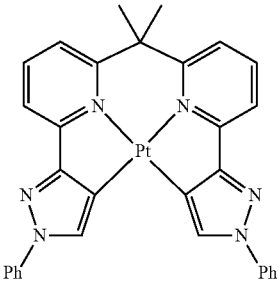 | US20060263635 |
| | 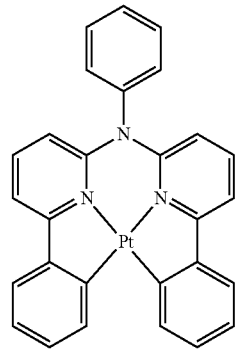 | US20060182992<br>US20070103060 |
| Cu complexes | 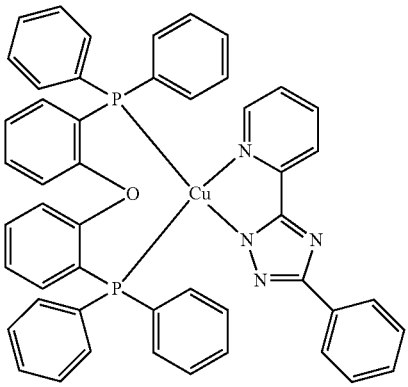 | WO2009000673 |
| | 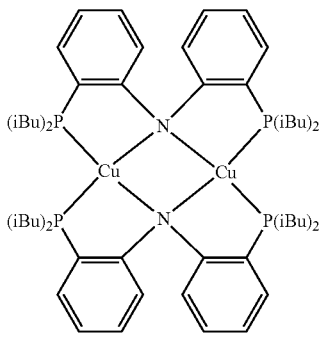 | US20070111026 |

TABLE 1-continued
| MATERIAL | EXAMPLES OF MATERIAL | PUBLICATIONS |
| --- | --- | --- |
| Gold complexes | 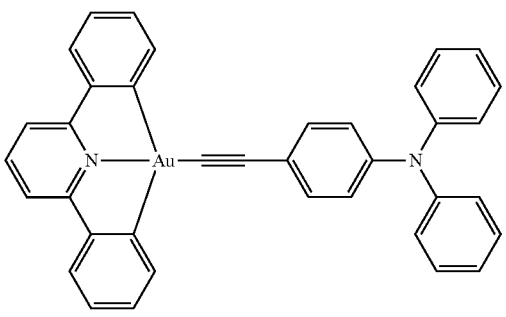 | Chem. Commun. 2906 (2005) |
| Rhenium(III) complexes | 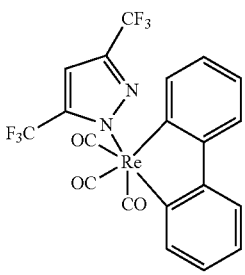 | Inorg. Chem. 42, 1248 (2003) |
| Osmium(II) complexes | 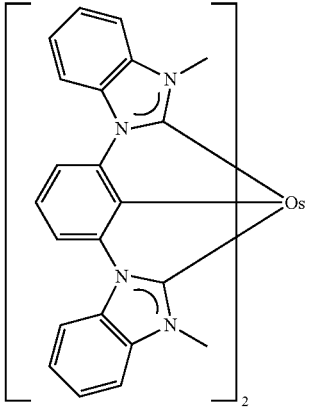 | U.S. Pat. No. 7,279,704 |
| Deuterated organometallic complexes | 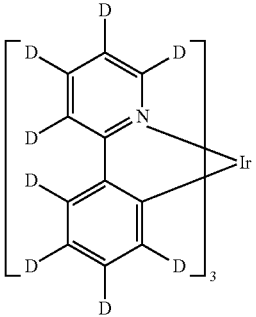 | US20030138657 |

TABLE 1-continued
| MATERIAL | EXAMPLES OF MATERIAL | PUBLICATIONS |
|---|---|---|
| Organometallic complexes with two or more metal centers | 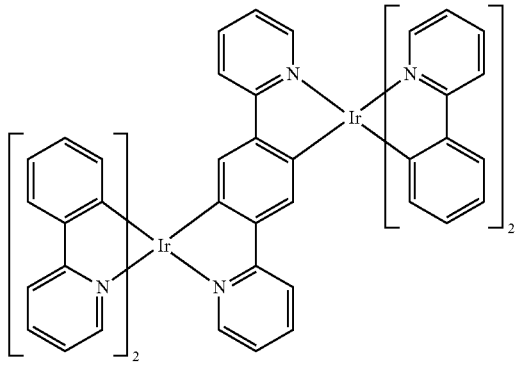 | US20030152802 |
| | 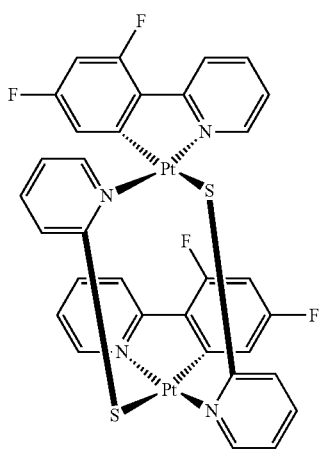 | U.S. Pat. No. 7,090 |
| Blue dopants | | |
| Iridium(III) organometallic complexes | 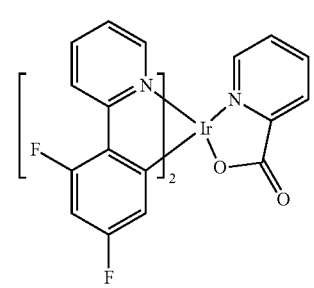 | WO2002002714 |
| | 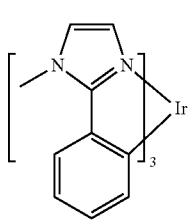 | WO2006009024 |
| | 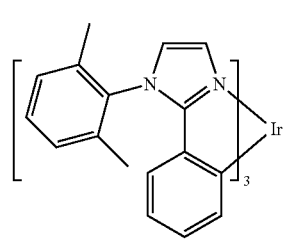 | US20060251923<br>US20110057559<br>US20110204333 |

TABLE 1-continued
| MATERIAL | EXAMPLES OF MATERIAL | PUBLICATIONS |
|---|---|---|
| | 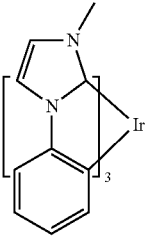 | U.S. Pat. No. 7,393,599, WO2006056418, US20050260441, WO2005019373 |
| | 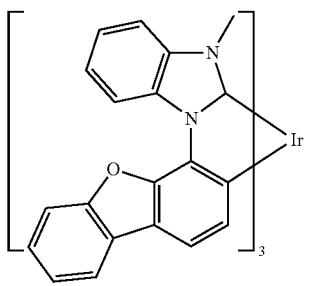 | U.S. Pat. No. 7,534,505 |
| | 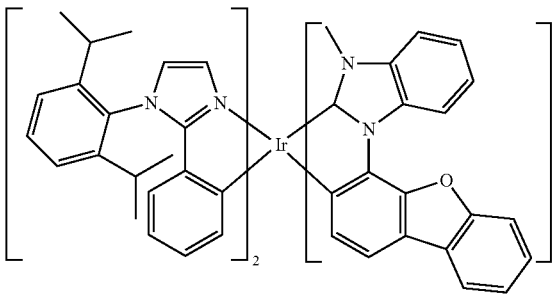 | WO2011051404 |
| | 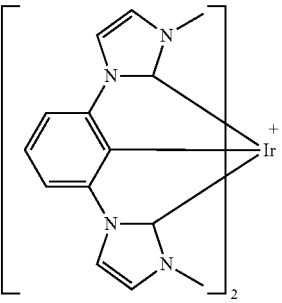 | U.S. Pat. No. 7,445,855 |
| | 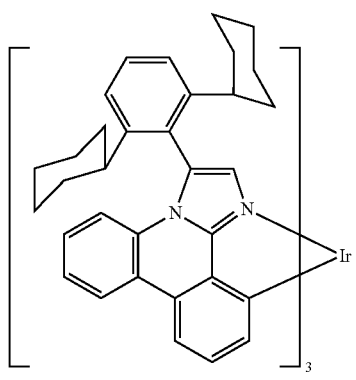 | US20070190359, US20080297033 US20100148663 |

TABLE 1-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |

TABLE 1-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 1-continued

| MATERIAL | EXAMPLES OF MATERIAL | PUBLICATIONS |
|---|---|---|
| | | Organometallics 23, 3745 (2004) |
| Gold complexes | | Appl. Phys. Lett. 74, 1361 (1999) |
| Platinum(II) complexes | | WO2006098120, WO2006103874 |
| Pt tetradenatate complexes with at least one metal-carbene bond | | U.S. Pat. No. 7,655,323 |

Exciton/hole blocking layer materials

| MATERIAL | EXAMPLES OF MATERIAL | PUBLICATIONS |
|---|---|---|
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE 1-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 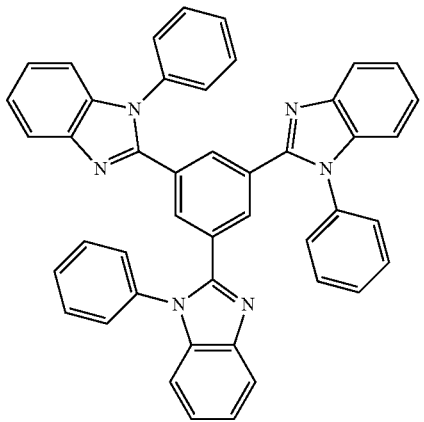 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 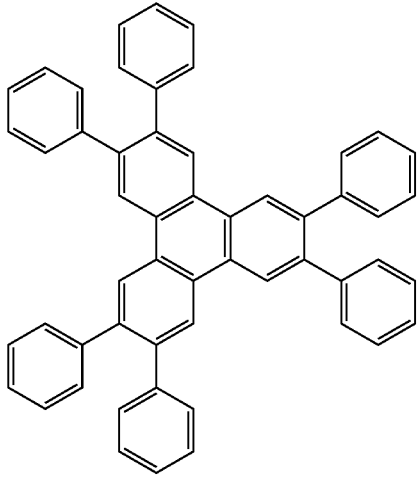 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 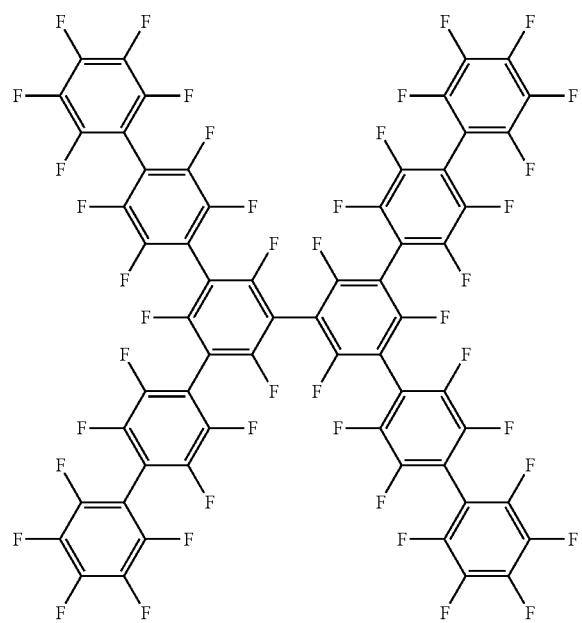 [SMILES: Fc1c(F)c(F)c(-c2c(F)c(F)c(-c3c(F)c(-c4c(F)c(F)c(-c5c(F)c(F)c(F)c(F)c5F)c(F)c4F)c(F)c(-c4c(F)c(-c5c(F)c(F)c(-c6c(F)c(F)c(F)c(F)c6F)c(F)c5F)c(F)c(-c5c(F)c(F)c(-c6c(F)c(F)c(F)c(F)c6F)c(F)c5F)c4F)c3F)c(F)c2F)c(F)c1F] | Appl. Phys. Lett. 79, 156 (2001) |

TABLE 1-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE 1-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 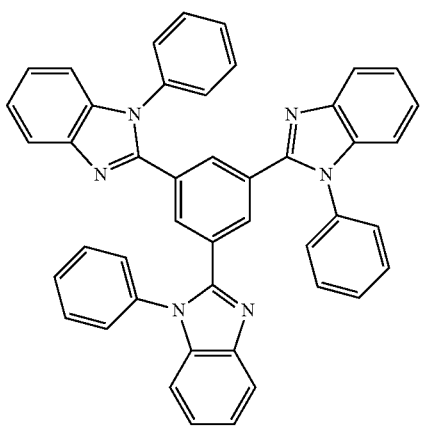 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 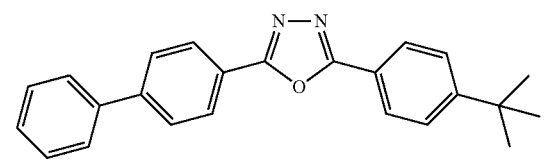 [SMILES: CC(C)(C)c1ccc(-c2nnc(-c3ccc(-c4ccccc4)cc3)o2)cc1] | Appl. Phys. Lett. 55, 1489 (1989) |
| | 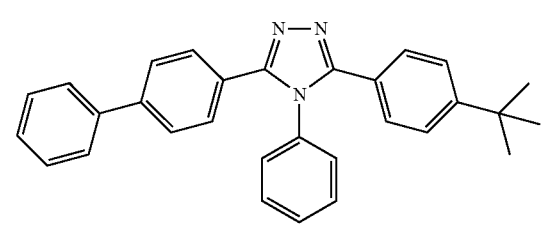 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 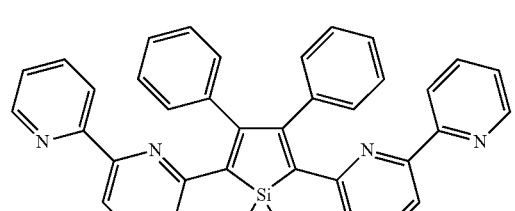 | Org. Electron. 4, 113 (2003) |
| Arylborane compounds | 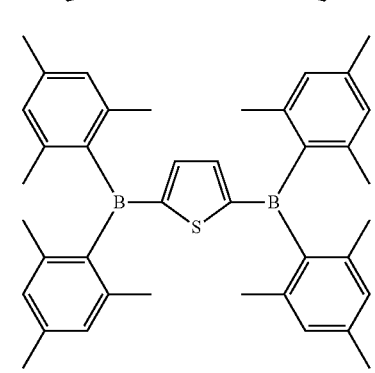 | J. Am. Chem. Soc. 120, 9714 (1998) |
| Fluorinated aromatic compounds | 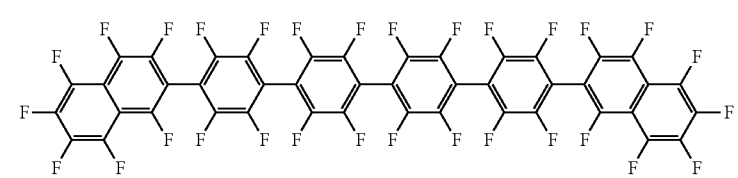 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 1-continued

| MATERIAL | EXAMPLES OF MATERIAL | PUBLICATIONS |
|---|---|---|
| Fullerene (e.g., C60) | 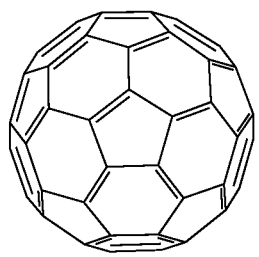 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 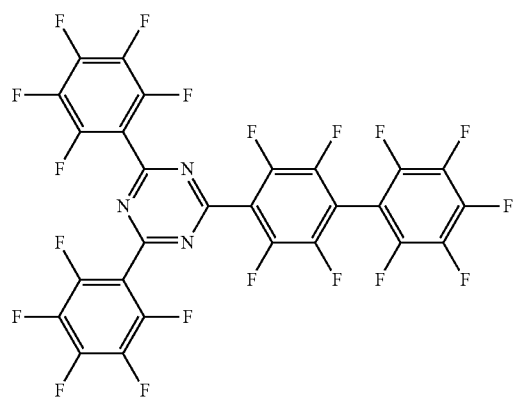 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 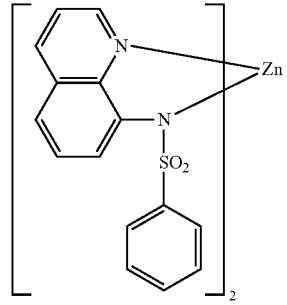 | U.S. Pat. No. 6,528,187 |

Emissive Dopant:

In some embodiments, the organic layer in the first device is an emissive layer and the compound of formula I is a host material. The organic layer may further comprise an emissive dopant. The emissive dopant is a transition metal complex having at least one ligand. Examples of the least one ligand include but are not limited to:

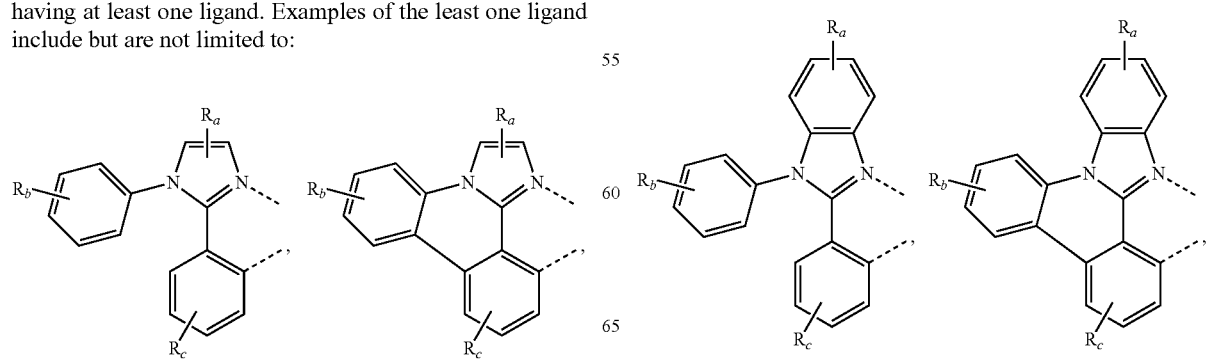

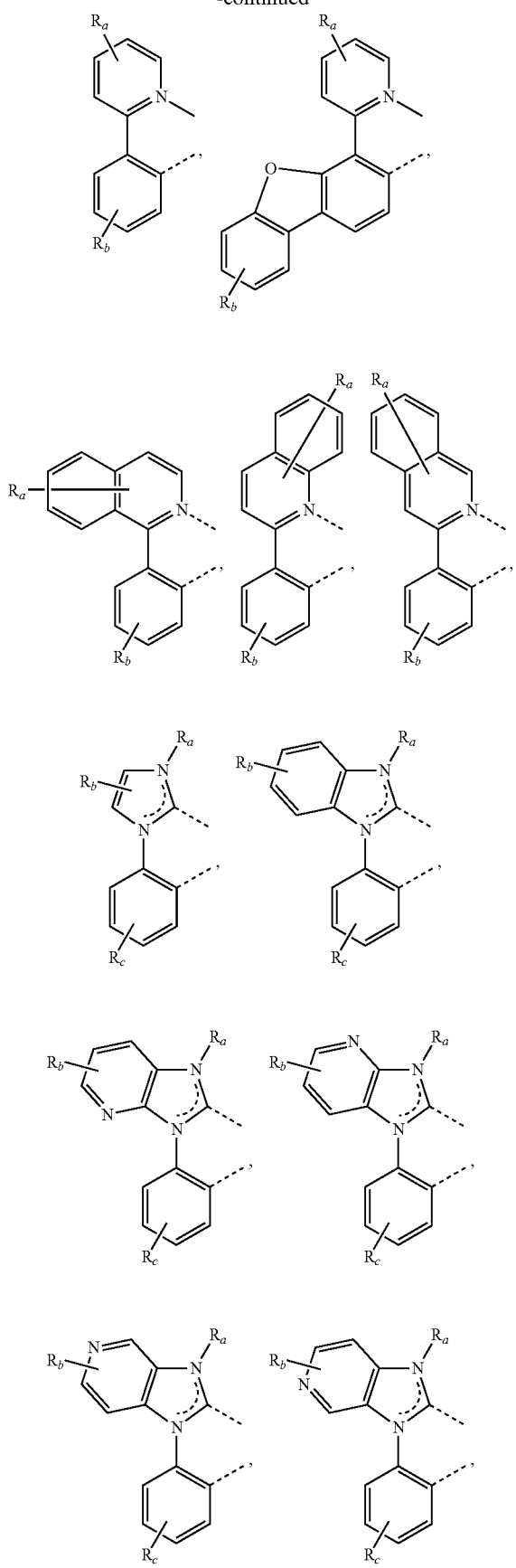

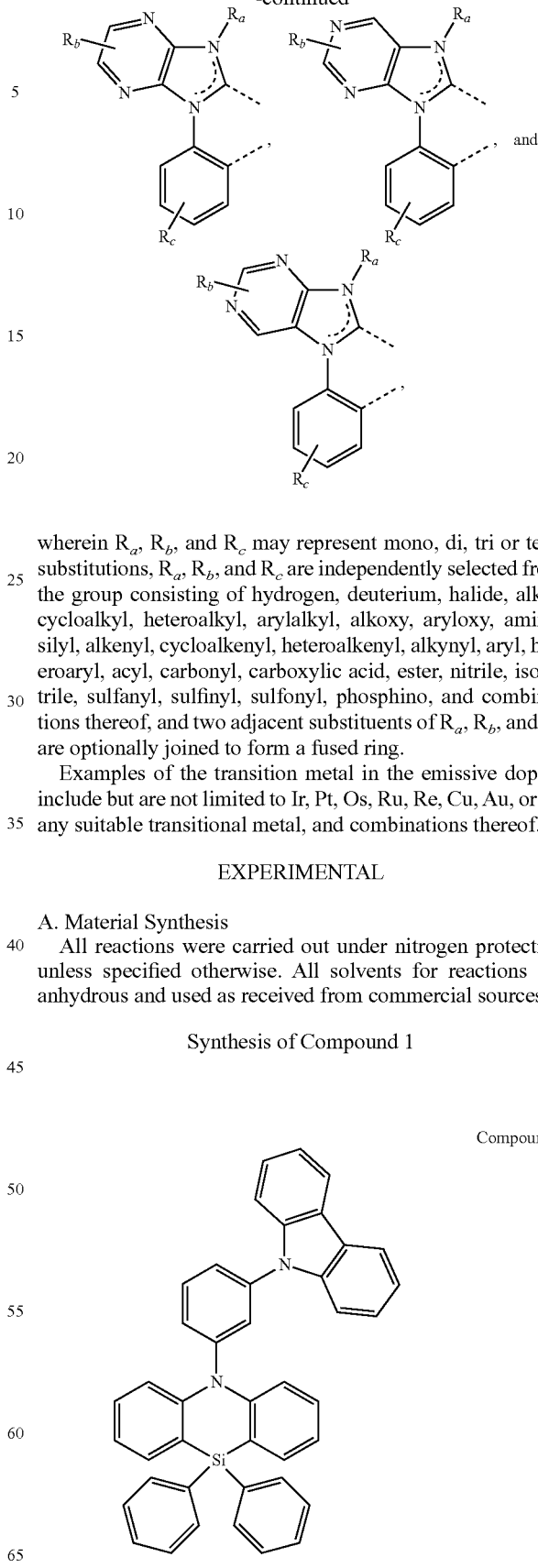

wherein $R_a$, $R_b$, and $R_c$ may represent mono, di, tri or tetra substitutions, $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and two adjacent substituents of $R_a$, $R_b$, and $R_c$ are optionally joined to form a fused ring.

Examples of the transition metal in the emissive dopant include but are not limited to Ir, Pt, Os, Ru, Re, Cu, Au, or Pd any suitable transitional metal, and combinations thereof.

EXPERIMENTAL

A. Material Synthesis

All reactions were carried out under nitrogen protection unless specified otherwise. All solvents for reactions are anhydrous and used as received from commercial sources.

Synthesis of Compound 1

Compound 1

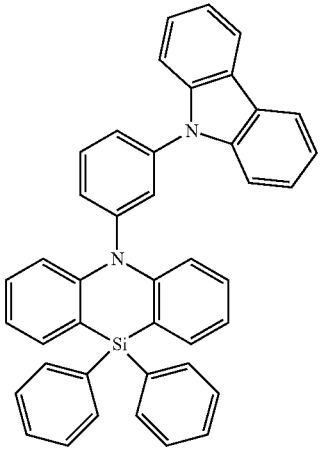

9-(3-iodophenyl)-9H-carbazole was first synthesized according to the following scheme:

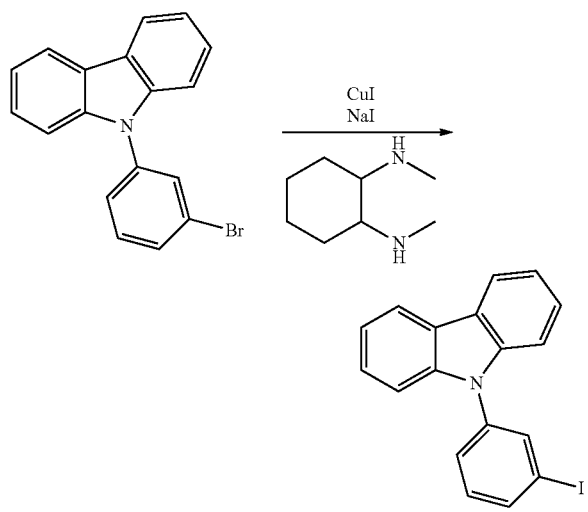

9-(3-bromophenyl)-9H-carbazole (4.5 g, 13.97 mmol), sodium iodide (4.19 g, 27.9 mmol), copper (I) iodide (0.798 g, 4.19 mmol), and dioxane (140 ml) were added into a 500 mL 3-necked flask. N1,N2-dimethylcyclohexane-1,2-diamine (1.101 ml, 6.98 mmol) was added. The reaction mixture was heated and refluxed overnight. After cooling down to room temperature, the mixture was filtered through a pad of Celite®, extracted with ethyl acetate and washed subsequently with brine and water. The crude material was purified via column chromatography using hexane and dichloromethane (90/10). Trituration from methanol afforded the pure compound as a white powder (4.95 g, 96% yield).

N-(3-(9H-carbazol-9-yl)phenyl)-2-bromo-N-(2-bromophenyl)aniline was then synthesized as follows:

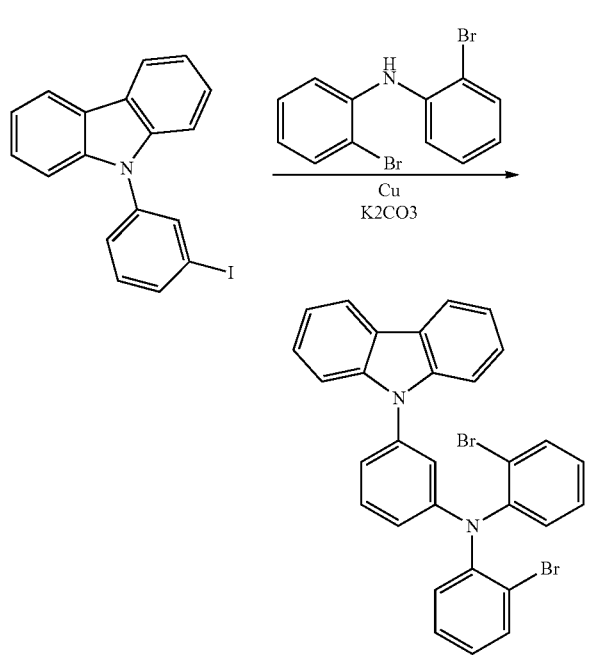

Bis(2-bromophenyl)amine (12.45 g, 38.1 mmol), 9-(3-iodophenyl)-9H-carbazole (14.06 g, 38.1 mmol), copper (1.210 g, 19.04 mmol), and K₂CO₃ (10.52 g, 76 mmol) were added into a 50 mL flask. The neat mixture was heated at 200° C. for 24 hours. After the reaction mixture was cooled, dichloromethane (200 mL) was added to solubilize the mixture. The mixture was filtered through a pad of Celite® and washed with several portions of dichloromethane. The crude material was purified via column chromatography using hexane and dichloromethane (85/15). N-(3-(9H-carbazol-9-yl)phenyl)-2-bromo-N-(2-bromophenyl)aniline (12.47 g, 21.94 mmol, 57.6% yield) was collected as an off-white powder.

Synthesis of 5-(3-(9H-carbazol-9-yl)phenyl)-10,10-diphenyl-5,10 dihydrodibenzo[b,e][1,4]azasiline (Compound 1)

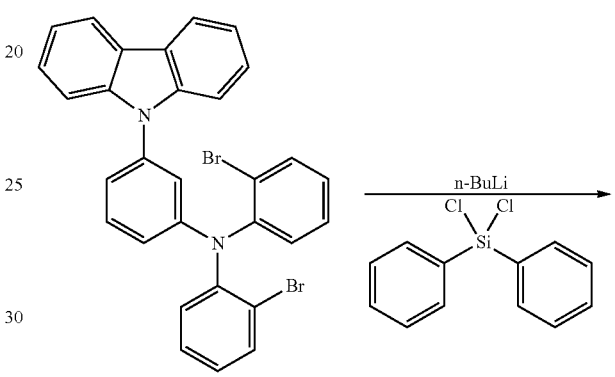

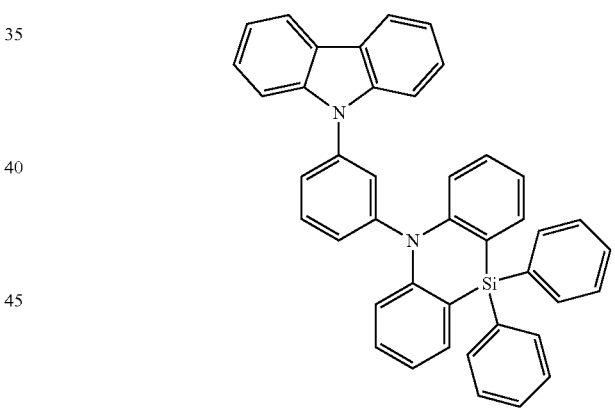

N-(3-(9H-carbazol-9-yl)phenyl)-2-bromo-N-(2-bromophenyl)aniline (4.05 g, 7.13 mmol) was added into a 250-mL round bottom flask and solubilized in dry THF (100 ml). The mixture was cooled down to −78° C. Butyllithium (5.70 ml, 14.25 mmol) was added dropwise. The mixture was stirred at −78° C. for 2 hours. Dichlorodiphenylsilane (1.467 ml, 7.13 mmol) was then added dropwise. The mixture was warmed to room temperature and stirred overnight. The reaction mixture was quenched with water, extracted three times with diethyl ether and washed three times with water. The crude material was purified by column chromatography using hexane and dichloromethane (85/15) as the eluent. After most of the impurities came out, the eluent was gradually changed to 25% dichloromethane in hexane. The white powder was then triturated in acetone and then recrystallized three times from dichloromethane and hexane. 1.5 g of 5-(3-(9H-carbazol-9- yl)phenyl)-10,10-diphenyl-5,10-dihydrodibenzo[b,e][1,4]azasiline was sublimed to afford 1.4 g yield of 33%.

Synthesis of Compound 2

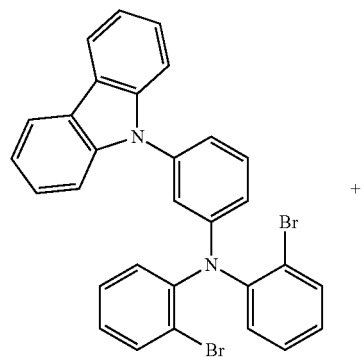

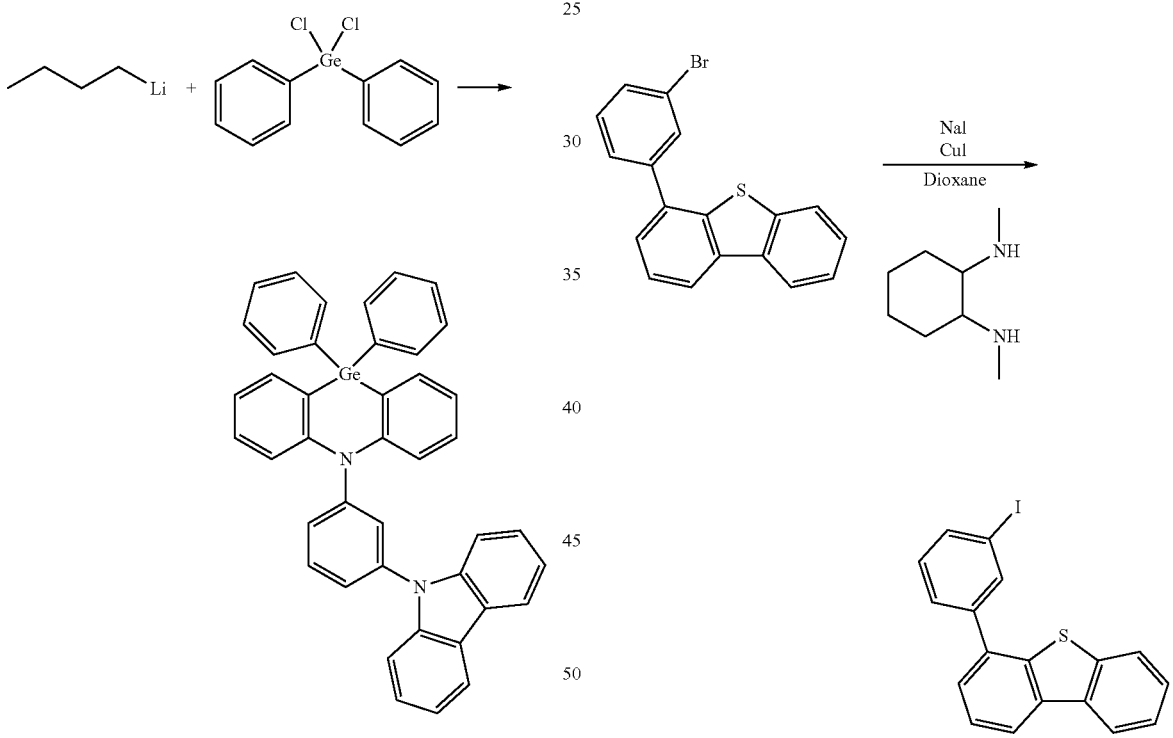

N-(3-(9H-carbazol-9-yl)phenyl)-2-bromo-N-(2-bromophenyl)aniline (6.00 g, 10.56 mmol) was added into a 500 mL RBF and solubilized in dry THF (151 ml). The mixture was cooled down to −78° C. using dry ice and acetone. Butyllithium (8.45 ml, 21.12 mmol) was added dropwise, and the reaction was allowed at this temperature for 2 hours. Dichlorodiphenylgermane (2.222 ml, 10.56 mmol) was then added dropwise and the reaction mixture was allowed to slowly warm to room temperature and was stirred overnight. The mixture was quenched with water, extracted three times with ether, and washed with brine and water. The crude material was purified by column chromatography using hexane and DCM (70/30). After trituration of the product in methanol and acetone successively, the purity was 99.4% (HPLC). The white powder was recrystallized three times from a mixture of DCM and hexane to afford 3.0 g of white crystals with high purity (99.9%). The compound was sublimed and 2.54 g was recovered.

Synthesis of Compound 8

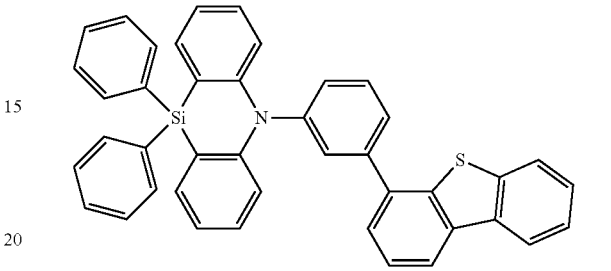

Compound 8

4-(3-iodophenyl)dibenzo[b,d]thiophene was synthesized according to the following scheme:

4-(3-bromophenyl)dibenzo[b,d]thiophene (9.00 g, 26.5 mmol), sodium iodide (7.95 g, 53.1 mmol), copper(I) iodide (1.516 g, 7.96 mmol), and dioxane (265 ml) were added into a 500 mL 3-necked flask. N1,N2-dimethylcyclohexane-1,2-diamine (2.092 ml, 13.26 mmol) was added. The mixture was degassed by bubbling nitrogen for 30 minutes and the reaction mixture was heated and refluxed overnight. After completion of the reaction, the heating was stopped and the mixture was filtered through a pad of Celite® and washed several times with DCM. The crude material was purified via column chromatography using hexane/DCM (80/20). The target 4-(3-iodophenyl)dibenzo[b,d]thiophene (9.33 g, 24.16 mmol, 91% yield) was afforded as a white solid.

2-bromo-N-(2-bromophenyl)-N-(3-(dibenzo[b,d]thiophen-4-yl)phenyl)aniline was synthesized as follows:

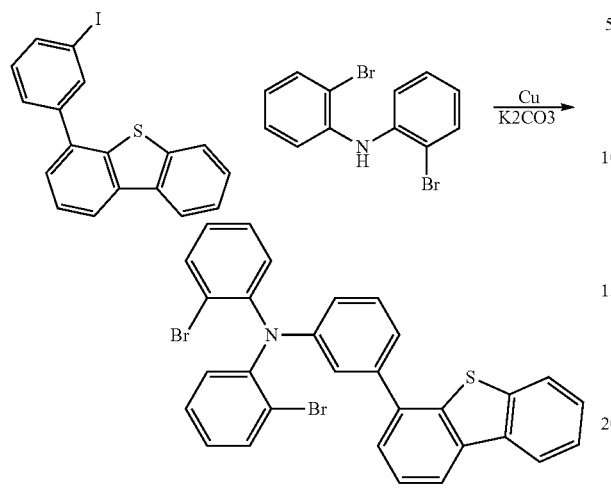

Bis(2-bromophenyl)amine (7.15 g, 21.86 mmol), 4-(3-iodophenyl)dibenzo[b,d]thiophene (9.29 g, 24.05 mmol), copper (0.695 g, 10.93 mmol), and K$_2$CO$_3$ (6.04 g, 43.7 mmol) were added into a 50 mL flask. The neat solids were heated at 200° C. for 36 hours. The mixture was then cooled. DCM (250 mL) was added to solubilize the organic products. The solution was filtered through a pad of Celite® and washed several times with DCM. The crude material was purified via column chromatography using hexane/DCM (85/15). The product collected from the column was triturated with methanol and filtered to afford 2-bromo-N-(2-bromophenyl)-N-(3-(dibenzo[b,d]thiophen-4-yl)phenyl)aniline (6.0 g, 10.25 mmol, 46.9% yield) as a yellowish powder.

Compound 8 was then synthesized as follows:

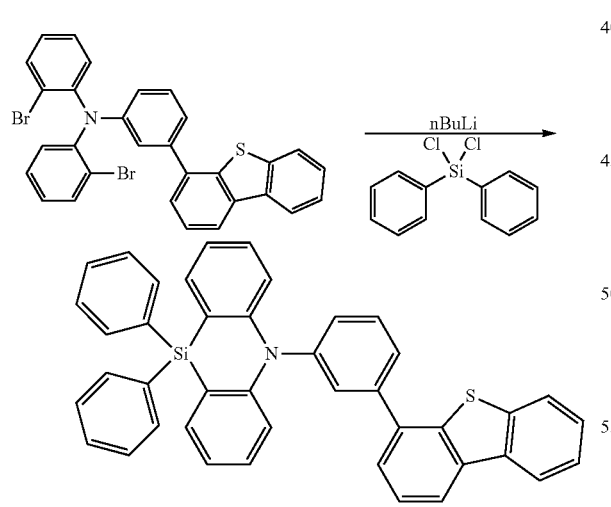

2-bromo-N-(2-bromophenyl)-N-(3-(dibenzo[b,d]thiophen-4-yl)phenyl)aniline (6.00 g, 10.25 mmol) was added into a 500 mL round bottom flask and solubilized in dry THF (171 ml). The solution was cooled down to −78° C. using dry ice and acetone. Butyllithium (8.20 ml, 20.50 mmol) was then added dropwise. The mixture was allowed to react −78° C. for 2 hours. Dichlorodiphenylsilane (2.321 ml, 11.28 mmol) was then slowly added to the mixture, which was then allowed to warm up to room temperature and stirred overnight. The mixture was quenched with water, extracted three times with Ether, and washed with brine and water. The crude material was purified via column chromatography using hexane/DCM (75/25). The purity after column was 97.8% by HPLC. Two recrystallization from hexane and DCM afforded the target 5-(3-(dibenzo[b,d]thiophen-4-yl)phenyl)-10,10-diphenyl-5,10-dihydrodibenzo[b,e][1,4]azasiline (compound 8, 3.4 g, 5.59 mmol, 54.6% yield) with a good purity on HPLC (99.9%). Compound 8 was sublimed and 3.4 g was collected.

Synthesis of Compound 10

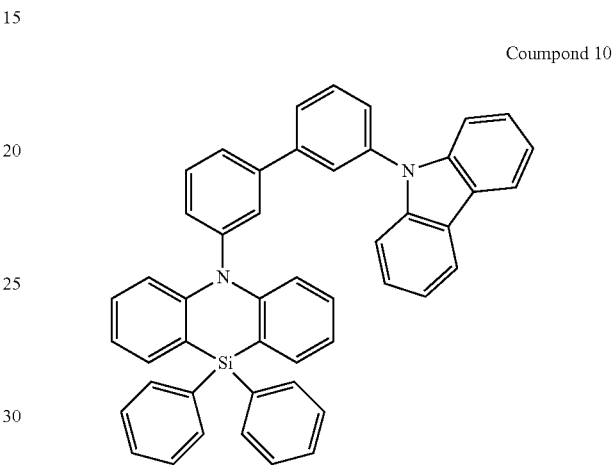

Coumpond 10

9-(3'-bromo-[1,1'-biphenyl]-3-yl)-9H-carbazole was synthesized according to the following scheme:

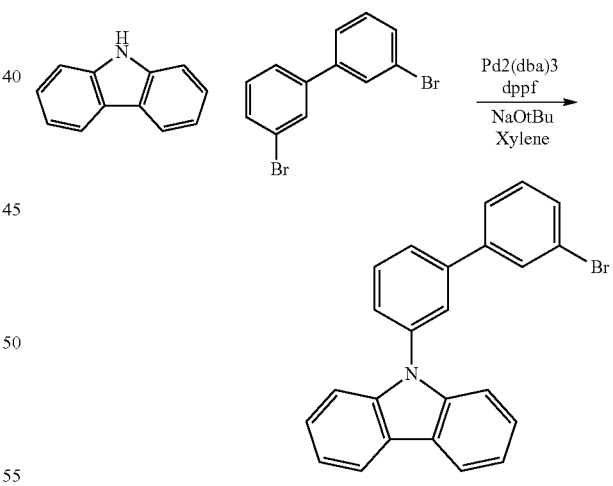

9H-carbazole (10 g, 59.8 mmol) and 3,3'-dibromo-1,1'-biphenyl (41.1 g, 132 mmol) were dissolved in xylene (100 ml). Sodium 2-methylpropan-2-olate (8.62 g, 90 mmol), Tris (dibenzylideneacetone)dipalladium(0) (Pd$_2$dba$_3$) (0.548 g, 0.598 mmol) and 1,1'-bis(diphenylphosphanyl) ferrocene (dppf) (0.663 g, 1.196 mmol) were then added into the mixture. The reaction mixture was degassed with nitrogen for 30 minutes, and heated to reflux for 48 h. The crude mixture was filtered through a pad of Celite® and washed with DCM. The solvents were evaporated under vacuum and the material was purified via column chromatography using hexane and DCM (95/5). After the excess of dibromobiphenyl came out, the polarity was increased gradually to 30% DCM in hexane. The compound 9-(3'-bromo-[1,1'-biphenyl]-3-yl)-9H-carbazole (13.02 g, 32.7 mmol, 54.7% yield) was afforded as white solids.

9-(3'-iodo-[1,1'-biphenyl]-3-yl)-9H-carbazole was synthesized as follows:

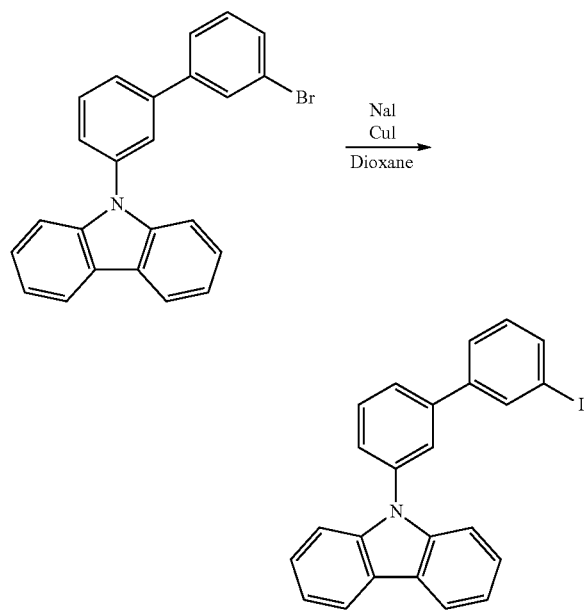

9-(3'-bromo-[1,1'-biphenyl]-3-yl)-9H-carbazole (9.50 g, 23.85 mmol), sodium iodide (7.15 g, 47.7 mmol), copper(I) iodide (1.363 g, 7.16 mmol), and dioxane (239 ml) were added into a 500 mL 3-necked flask. N1,N2-dimethylcyclohexane-1,2-diamine (1.881 ml, 11.93 mmol) was added. The reaction mixture was heated and refluxed overnight. After completion of the reaction, the reaction mixture was cooled to room temperature. The reaction mixture was filtered through a pad of Celite® and washed several times with DCM. The solvent are evaporated in vacuum. The crude material was purified by column chromatography using hexane and DCM (75/25) and gradually increasing DCM to a ratio of hexane/DCM 50/50. The product was further purified by trituration from methanol. 9-(3'-iodo-[1,1'-biphenyl]-3-yl)-9H-carbazole (10.2 g, 22.91 mmol, 96% yield) was obtained as a white solid.

N-(2-bromophenyl)-N-(3-bromophenyl)-3'-(9H-carbazol-9-yl)-[1,1'-biphenyl]-3-amine as then synthesized as follows:

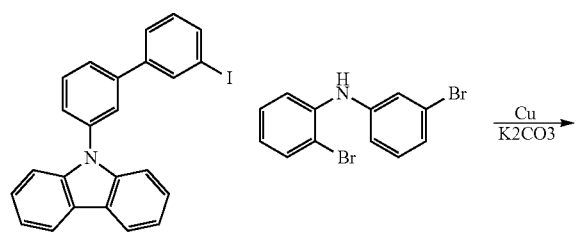

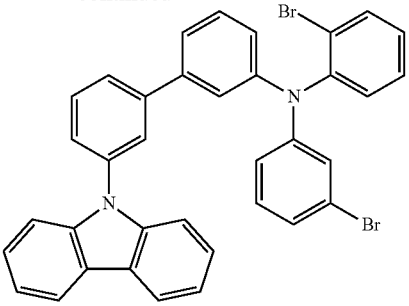

Bis(2-bromophenyl)amine (7.05 g, 21.56 mmol), 9-(3'-iodo-[1,1'-biphenyl]-3-yl)-9H-carbazole (10.08 g, 22.64 mmol), copper (0.685 g, 10.78 mmol), and $K_2CO_3$ (5.96 g, 43.1 mmol) were added into a 50 mL flask. The neat mixture was heated at 200° C. for 24 hours. It was then cooled and DCM (200 mL) was added to solubilize the mixture. The solution was filtered through a pad of Celite® and washed several times with DCM. The crude material was purified via column chromatography starting with hexane and DCM (85/15) and gradually increased DCM to a ratio of hexane/DCM 70/30. Trituration from acetone afforded the target as a mixture of dibromo, bromoiodo and diodo (8.00 g, 58% yield).

Compound 10 was then synthesized as follows:

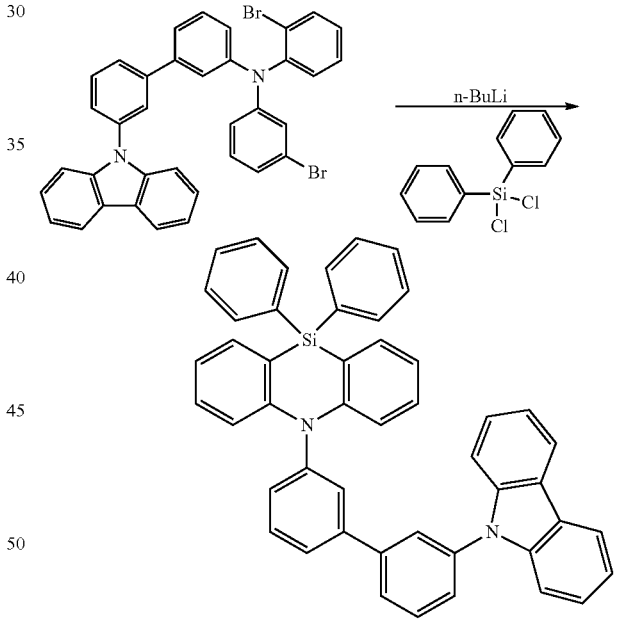

N-(2-bromophenyl)-N-(3-bromophenyl)-3'-(9H-carbazol-9-yl)-[1,1'-biphenyl]-3-amine was added into a 250 mL round bottom flask, and solubilized in dry THF (155 ml). The solution was cooled down to −78° C. using dry ice and Acetone. Butyllithium (7.45 ml, 18.62 mmol) was added dropwise and the reaction mixture was stirred −78° C. for 2 hours. Dichlorodiphenylsilane (2.108 ml, 10.24 mmol) was then added dropwise. The reaction mixture was allowed to slowly warm to room temperature and was stirred overnight. The reaction was quenched with water, extracted three times with ether, washed with brine and water. The crude material was purified with column chromatography using hexane/DCM (75/25). The product was collected as a white powder with a purity of 99.3% by HPLC. The product was recrystallized twice from DCM and hexane. The target 5-(3'-(9H-carbazol-9-yl)-[1,1'-biphenyl]-3-yl)-10,10-diphenyl-5,10-dihydrodibenzo[b,e][1,4]azasiline (Compound 10) was afforded as a white powder (1.8 g, 29% yield). Compound 10 was then sublimed and 1.2 g was collected.

Synthesis of Comparative Example 1

Comparative Compound 1

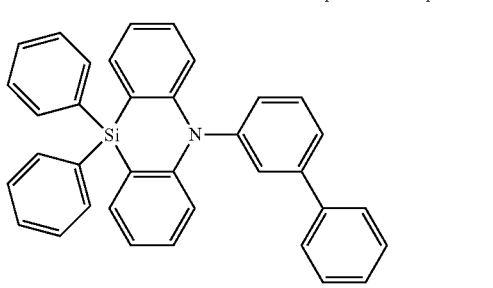

3-iodo-1,1'-biphenyl was first synthesized according to the following scheme:

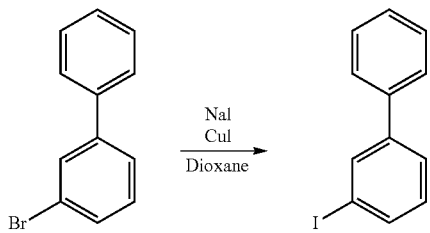 [SMILES: Brc1cccc(-c2ccccc2)c1 ; Ic1cccc(-c2ccccc2)c1]

3-bromo-1,1'-biphenyl (5.00 g, 21.5 mmol), sodium iodide (6.43 g, 42.9 mmol), copper(I) iodide (1.226 g, 6.43 mmol), and dioxane (214 ml) were added into a 500 mL 3-necked flask. N1,N2-dimethylcyclohexane-1,2-diamine (1.691 ml, 10.72 mmol) was then added. The solution was heated and refluxed overnight. Upon completion of the reaction, the reaction mixture was cooled to room temperature, filtered through a pad of celite and washed several times with dichloromethane. The solvents are evaporated under vacuum and the crude material was purified via column chromatography using hexane/DCM (90/10). The target 3-iodo-1,1'-biphenyl (5.5 g, 19.64 mmol, 92% yield) was afforded as a colorless oil.

N,N-bis(2-bromophenyl)-[1,1'-biphenyl]-3-amine was then synthesized as follows:

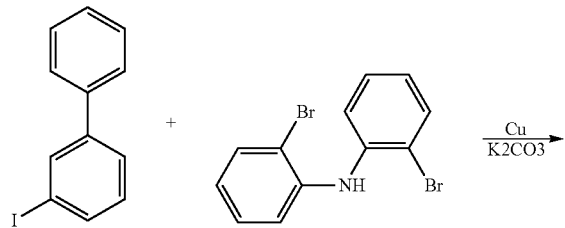

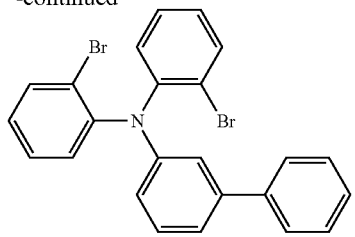

Bis(2-bromophenyl)amine (6.0 g, 18.35 mmol), 3-iodo-1,1'-biphenyl (5.65 g, 20.18 mmol), copper (0.583 g, 9.17 mmol), and $K_2CO_3$ (5.07 g, 36.7 mmol) were added into a 50 mL flask. The mixture was heated at 200° C. for 24 hours. After the reaction mixture was cooled, DCM (200 mL) was added. The mixture was filtered through a pad of Celite® and washed several times with DCM. The crude material was purified via column chromatography using hexane/DCM (85/15). The target was collected (3.4 g, 38% yield) as a yellowish powder, which was a mixture of dibromo, bromoiodo and diodo substituted product.

Comparative Compound 1 was then synthesized as follows:

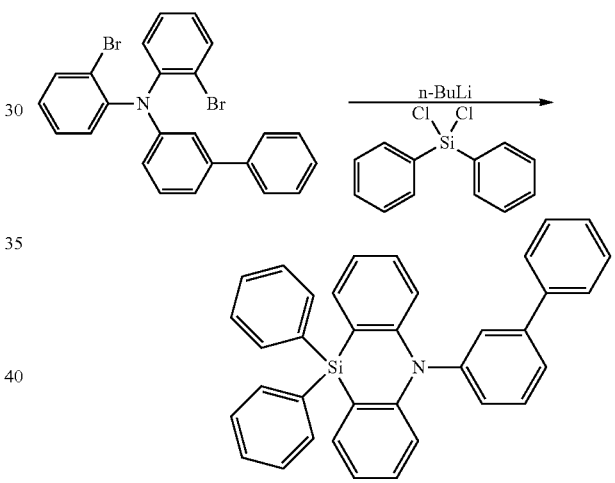

N,N-bis(2-bromophenyl)-[1,1'-biphenyl]-3-amine (3.65 g, 7.62 mmol) was added into a 250-mL round bottom flask and solubilized in dry THF (109 ml). The solution was cooled down to −78° C. using dry ice and Acetone. Butyllithium (6.09 ml, 15.23 mmol) was then added dropwise and stirred at this temperature for 2 hours. Dichlorodiphenylsilane (1.725 ml, 8.38 mmol) was added dropwise to the mixture, which was allowed to warm up to room temperature and was stirred overnight. The reaction mixture was quenched with water, extracted three times with ether, and washed with brine and water. The crude material was purified via column chromatography starting with hexane/DCM (90/10). Sublimation resulted in 1.0 g of Comparative Compound 1.

B. Device Examples

All devices were fabricated by high vacuum (~$10^{-7}$ Torr) thermal evaporation. The anode electrode was 80 nm of indium tin oxide (ITO). The cathode consisted of 1 nm of LiF followed by 100 nm of aluminum. All devices were encapsulated with a glass lid sealed with an epoxy resin in a nitrogen glove box 1 ppm of $H_2O$ and $O_2$) immediately after fabrication, and a moisture getter was incorporated inside the package.

All device examples had organic stacks consisting of, sequentially, from the ITO surface, 10 nm thick of Compound LG101 (from LG Chemical) as the hole injection layer (HIL), 30 nm of 4,4'-bis[N-(1-naphthyl)-N-phenylamino]biphenyl (α-NPD) as the hole transporting layer (HTL), and 300 Å of inventive hosts or comparative hosts doped with 15 wt % or 20% of Compound D as the emissive layer (EML). On the top of the EML, 5 nm of Compound BL was deposited as a hole blocking (BL) and then followed by 40 nm of tris(8-hydroxyquinolinato)aluminum (Alq$_3$) as the ETL.

The device structures of the device example and comparative examples are shown in Table 2. The device performance data are summarized in Table 3. As used herein, Dopant D, NPD, Alq$_3$, and Compound BL have the following structures:

Dopant D

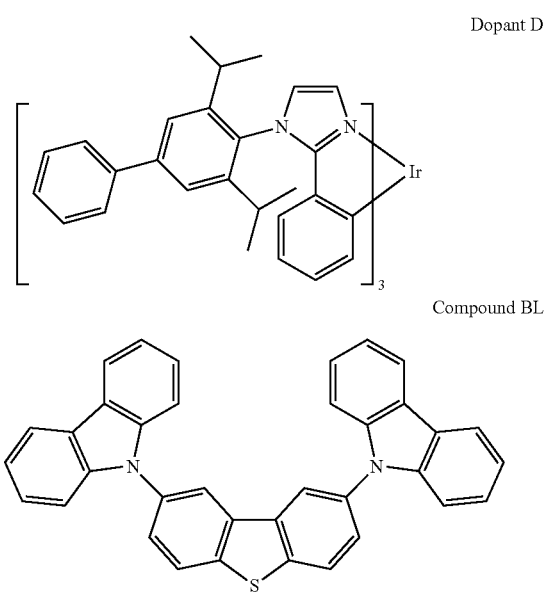

Compound BL

NPD

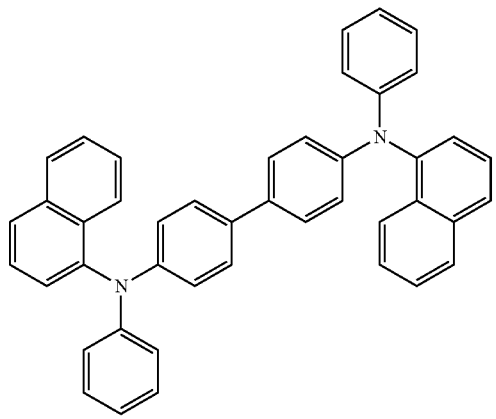

Alq$_3$

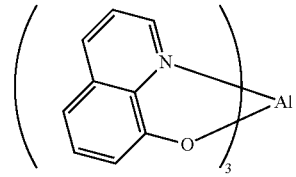

TABLE 2

Device structures of inventive compounds and comparative compounds

| Example | HIL | HTL | EML (300 Å, doping %) | | BL | ETL |
|---|---|---|---|---|---|---|
| Example 1 | LG101 100 Å | NPD 300 Å | Compound 8 | Dopant D 15% | Compound BL 50 Å | Alq$_3$ 400 Å |
| Example 2 | LG101 100 Å | NPD 300 Å | Compound 10 | Dopant D 15% | Compound BL 50 Å | Alq$_3$ 400 Å |
| Comparative Example 1 | LG101 100 Å | NPD 300 Å | Comparative Compound 1 | Dopant D 15% | Compound BL 50 Å | Alq$_3$ 400 Å |

TABLE 3

Device results

| | 1931 CIE | | λ max | At 1000 nits | | | At 20 mA/cm$^2$ |
|---|---|---|---|---|---|---|---|
| Example | x | y | [nm] | LE [cd/A] | EQE [%] | PE [lm/W] | Relative LT$_{80\%}$ |
| Example 1 | 0.173 | 0.390 | 474 | 48.8 | 21.6 | 23.2 | 187 |
| Example 2 | 0.170 | 0.384 | 474 | 53.2 | 23.9 | 29.8 | 61 |
| Comparative Example 1 | 0.171 | 0.375 | 474 | 44.9 | 20.5 | 23.1 | 1 |

Table 3 summarizes the performance of the devices. The luminous efficiency (LE), external quantum efficiency (EQE) and power efficiency (PE) were measured at 1000 nits. The lifetime ($LT_{80\%}$) was defined as the time required for the device to decay to 80% of its initial luminance under a constant current density of 20 mA/cm². Compared to Comparative Example 1 having Comparative Compound 1, device Examples 1 and 2 having Compounds 8 and 10, respectively, have reasonable EQE. The lifetime of the device examples was significantly improved, when the exemplary compound comprises a capping end of dibenzothiophene (in compound 8) or carbazole (in Compound 10). Compound 8 showed a good EQE of about 24%, and much higher lifetime compared to comparative compound 1. The EQE of device Example 1 containing Compound 8 was close to the device Example 2 containing Compound 10 (22% vs. 24%). These results have confirmed that the new compounds based on dibenzoazasiline can achieve good efficiency. It might be due to balanced charge transport. For example, Compounds 8 and 10 contain a good hole transporting part with carbazole or dibenzothiophene and presumably a good electron transporting piece with the dibenzoazasiline. Comparative Compound 1 does not have the feature of the inventive compounds. The compound having the formula I provides good balance between hole and electron transporting, which spreads the charge recombination zone and helps preserve a high efficiency at high brightness by suppressing or reducing exciton quenching.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having a formula I:

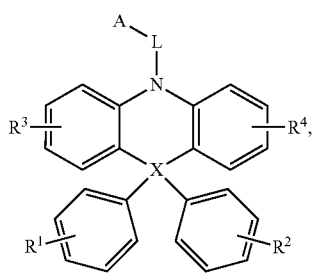

(I)

wherein
X is Si or Ge;
$R^1$ and $R^2$ represent mono, di, tri, tetra, or penta substitutions or no substitution;
$R^3$, $R^4$ represent mono, di, tri, or tetra substitutions or no substitution;
$R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

$R^1$ and $R^2$ are optionally joined to form a ring, which may be further substituted;

L is a single bond or comprises an aryl or heteroaryl group having from 5-20 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof; and A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof, which are optionally further substituted with one or more groups selected from hydrogen, deuterium, alkyl, cycloalkyl, arylalkyl, alkoxy, aryloxy, amino, silyl, aryl, heteroaryl, and combinations thereof;

wherein the substitution of one or more groups in A is optionally fused to the indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group.

2. The compound of claim 1, wherein L is selected from the group consisting of:

single bond,

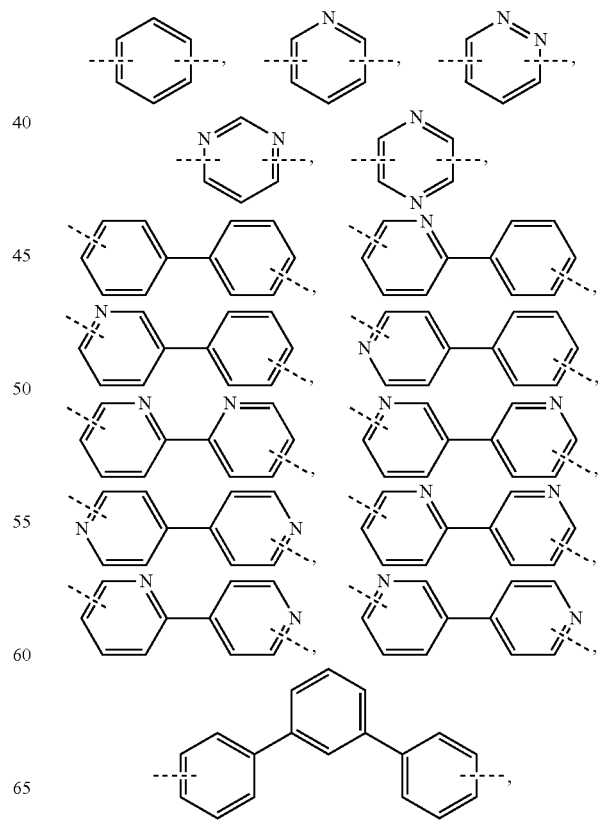

-continued

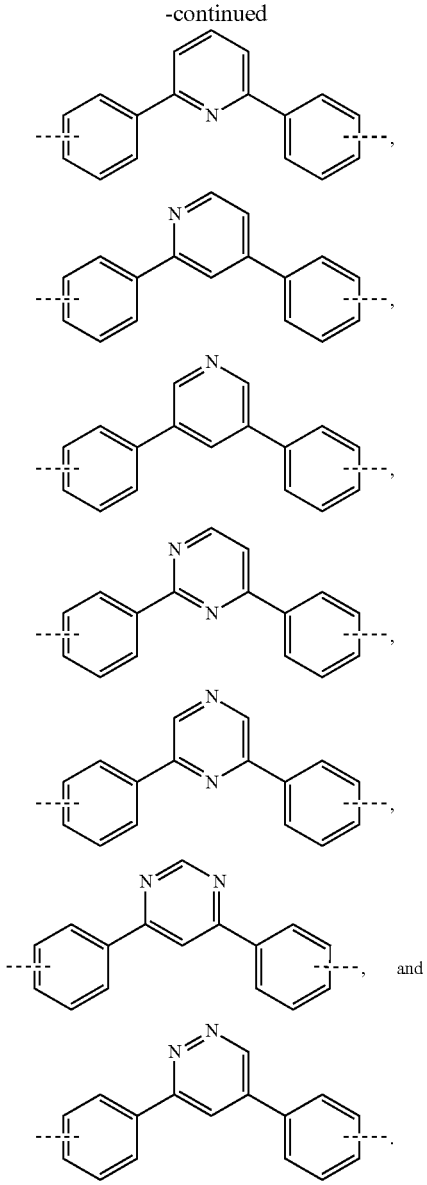

3. The compound of claim 1, wherein A is

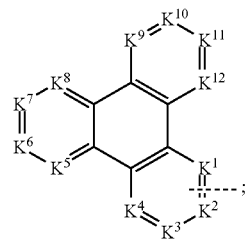

wherein
K$^1$ to K$^{12}$ are independently selected from N and C—R'; and
R' is selected from the group consisting of hydrogen, deuterium, alkyl, cycloalkyl, arylalkyl, alkoxy, aryloxy, amino, silyl, aryl, heteroaryl, and combinations thereof.

4. The compound of claim 1, wherein A is selected from the group consisting of:

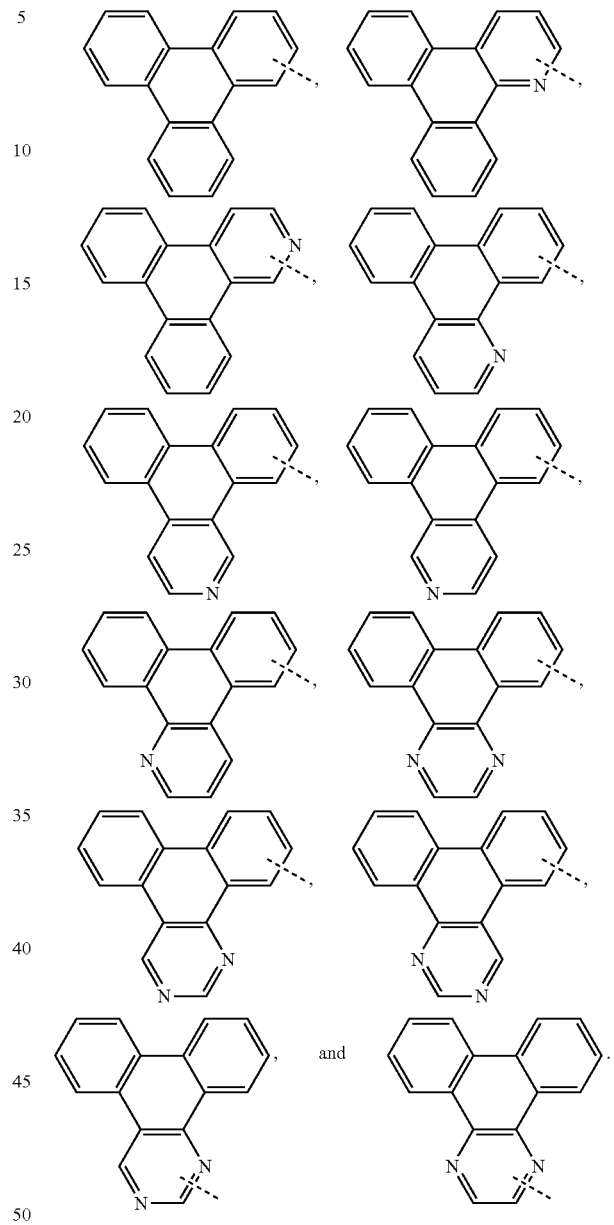

5. The compound of claim 1, wherein A is selected from the group consisting of:

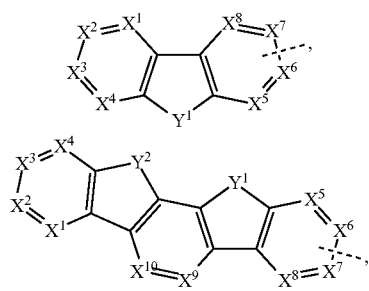

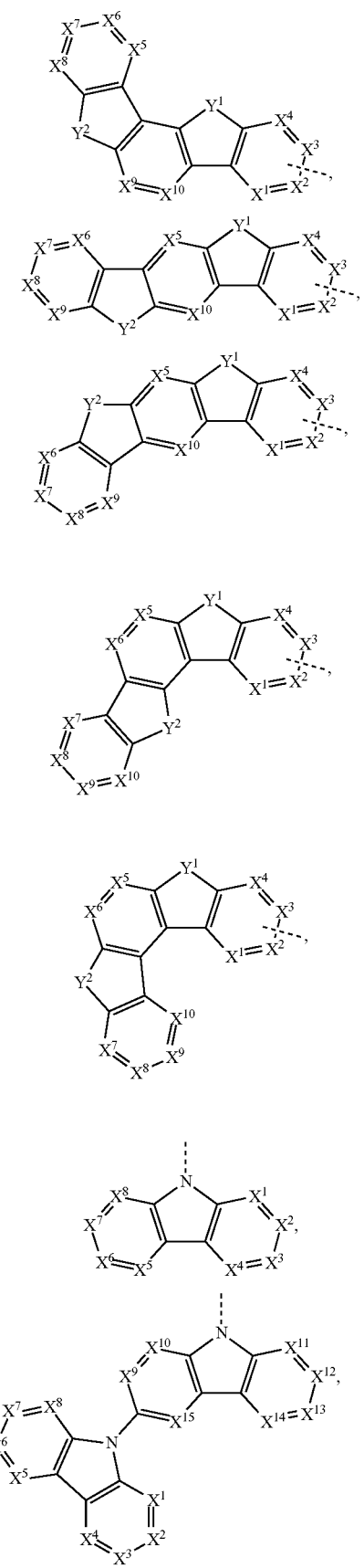

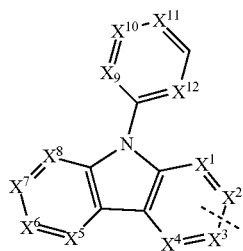

wherein

X¹-X¹⁵ are independently selected from the group consisting of N and C—R", wherein R" is selected from a group consisting of hydrogen, deuterium, alkyl, cycloalkyl, arylalkyl, alkoxy, aryloxy, amino, silyl, aryl, heteroaryl, and combinations thereof; and Y¹ and Y² are independently selected from the group consisting of O, S, and Se.

6. The compound of claim 1, wherein A is selected from the group consisting of:

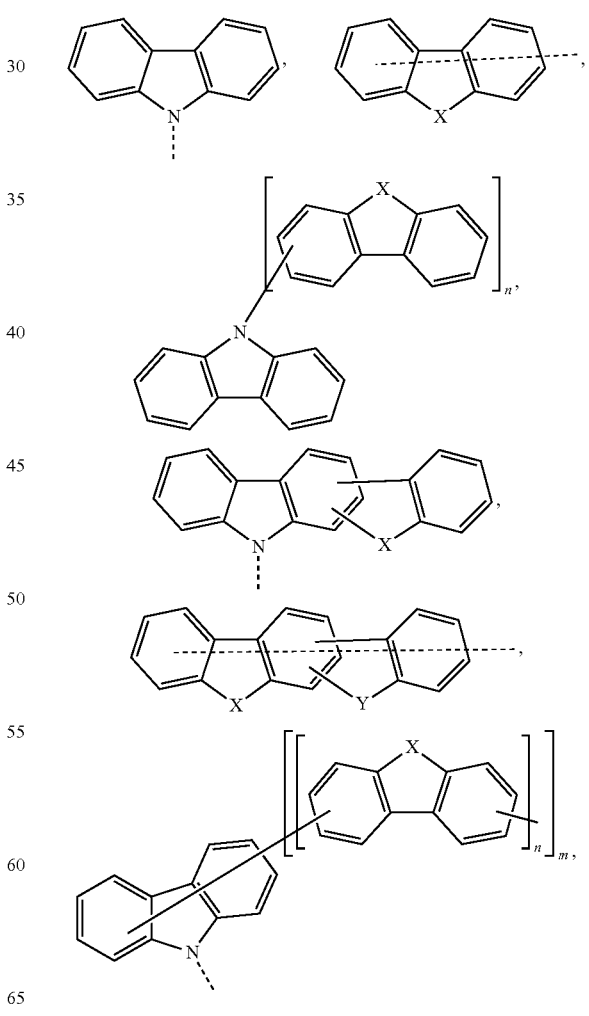

-continued
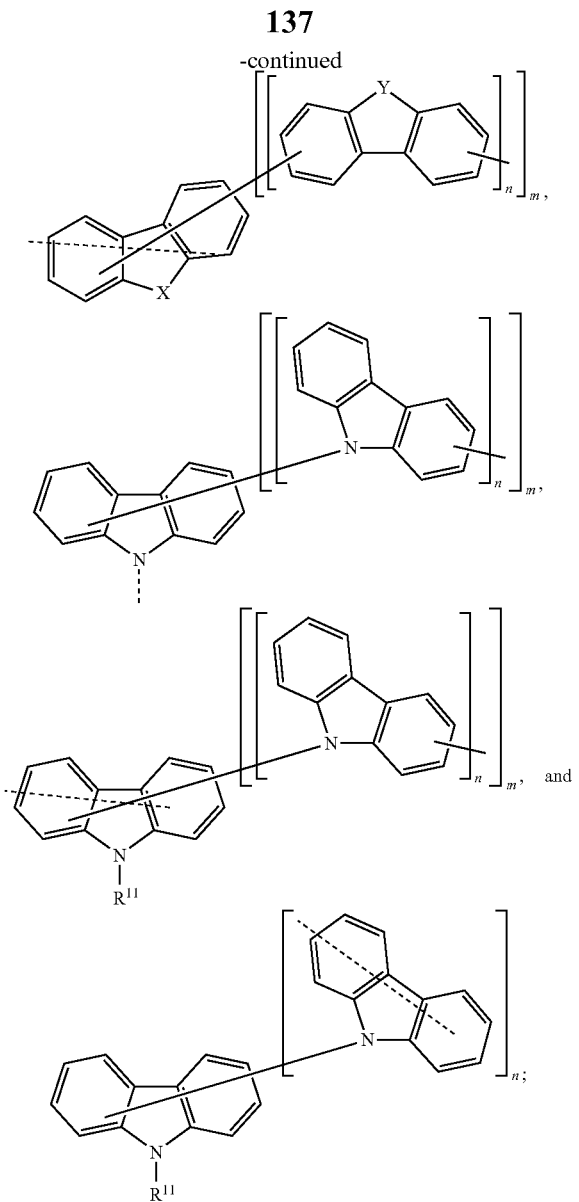
and
wherein
n is an integer from 1 to 20;
m is an integer from 1 to 20;
X and Y are independently selected from the group consisting of O, S, and NR[14]; and
R[11], R[12], R[13] and R[14] are selected from the group consisting of aryl and heteroaryl.
7. The compound of claim 1, wherein A is selected from the group consisting of:
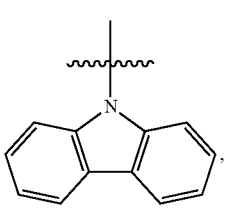
D[101]
-continued
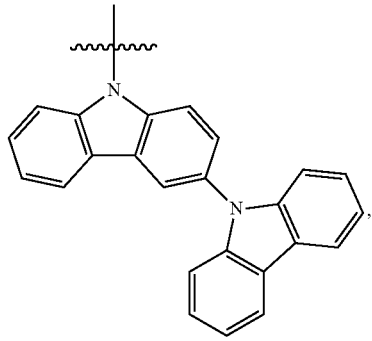
D[102]
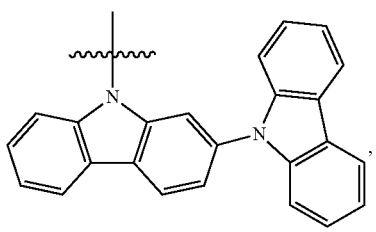
D[103]
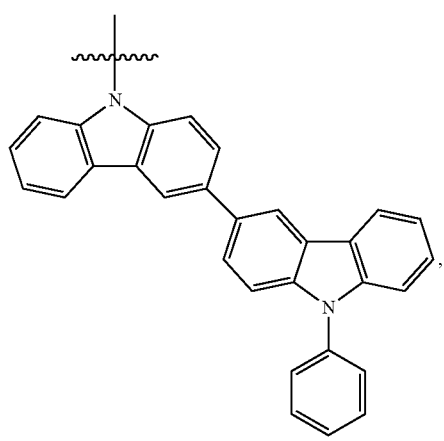
D[104]
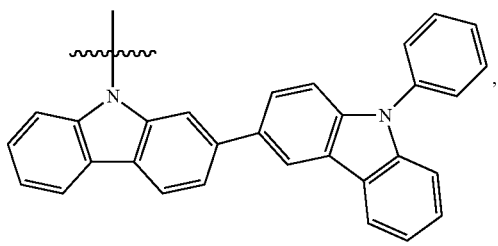
D[105]
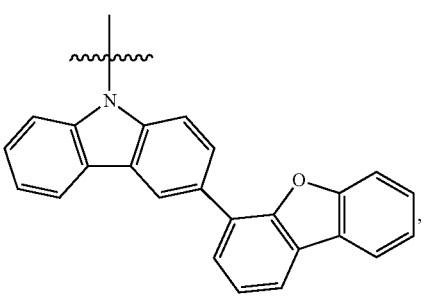
D[106]

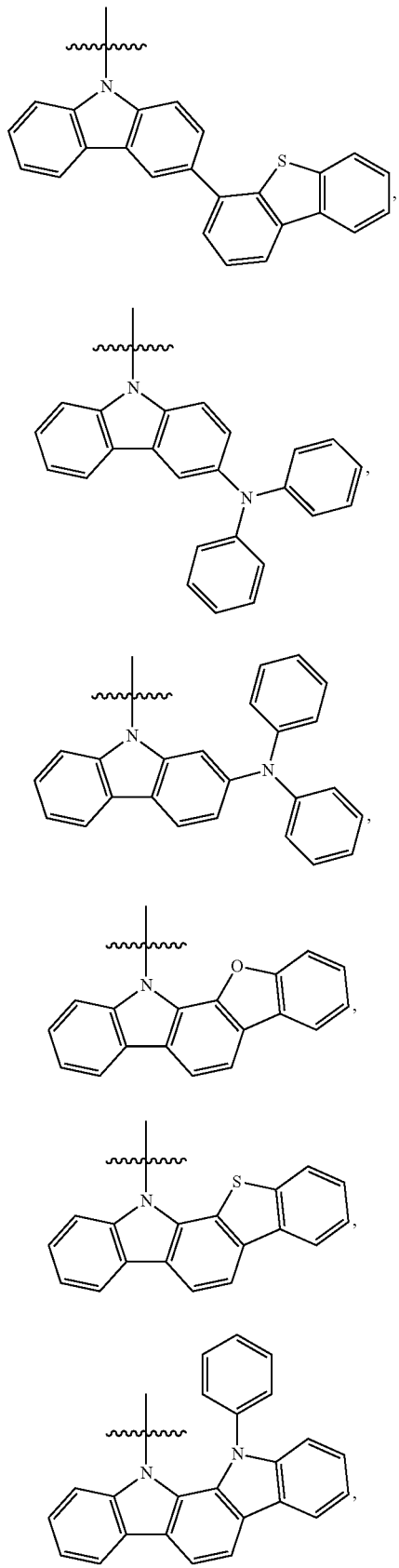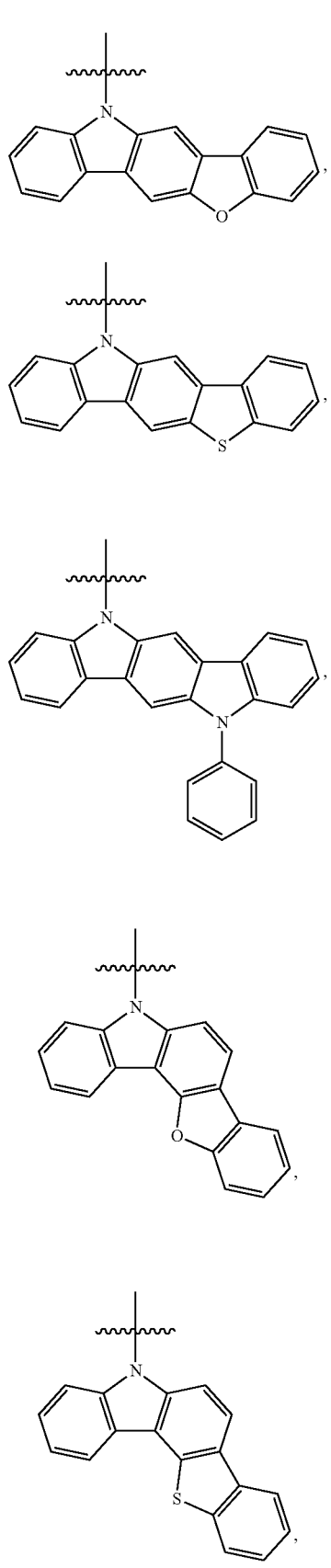

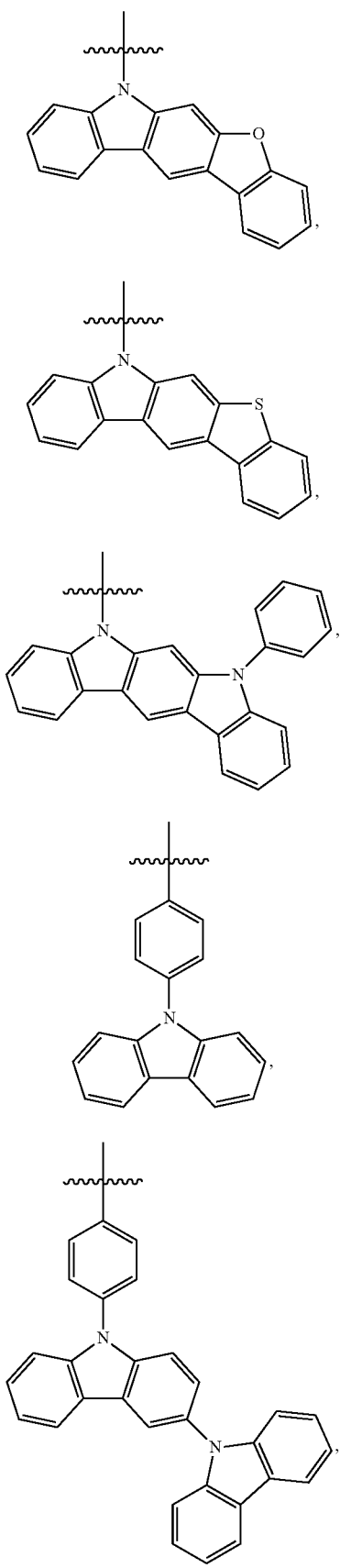
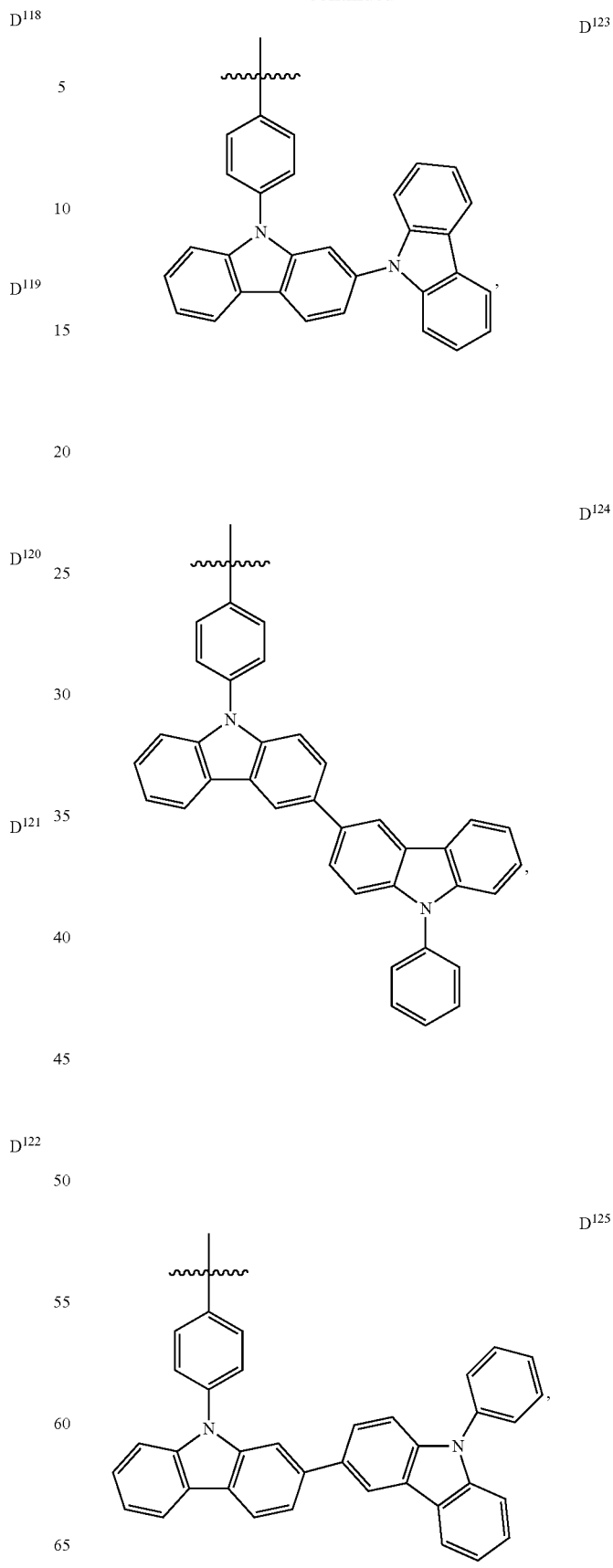

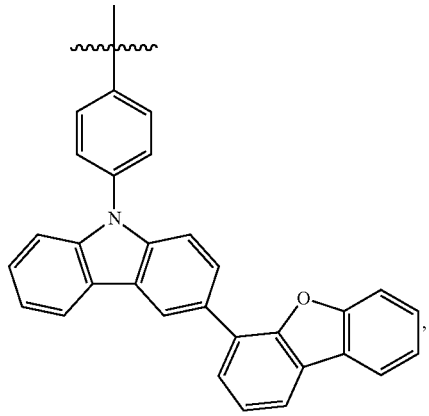
D126
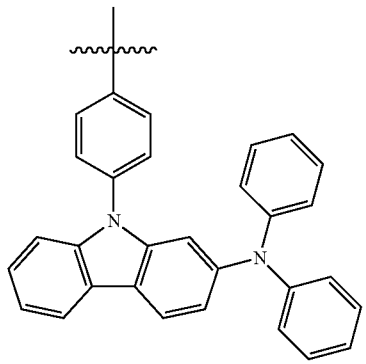
D129
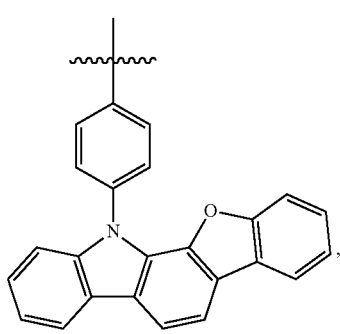
D130
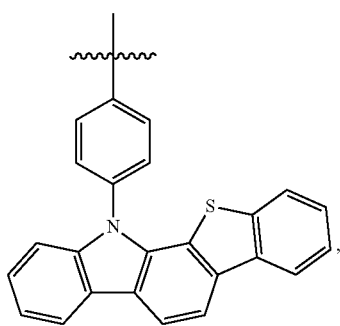
D131
D127
D128
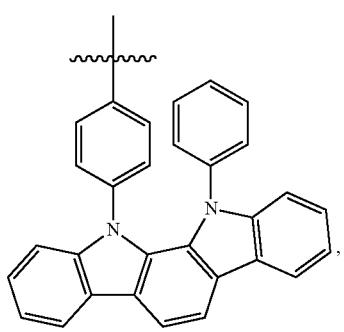
D132

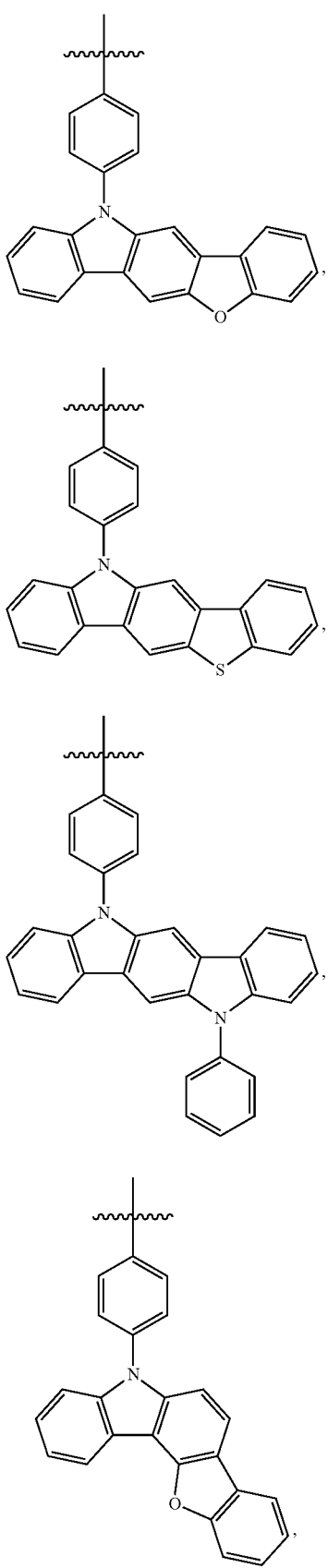
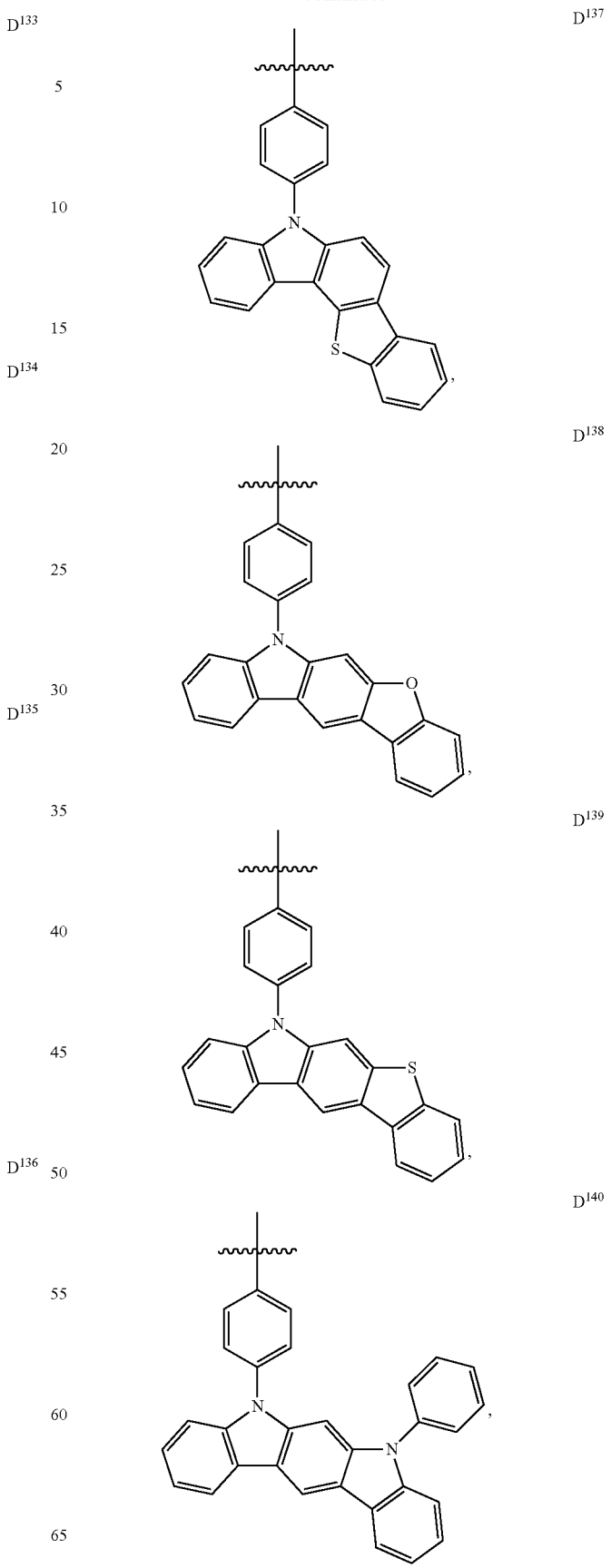

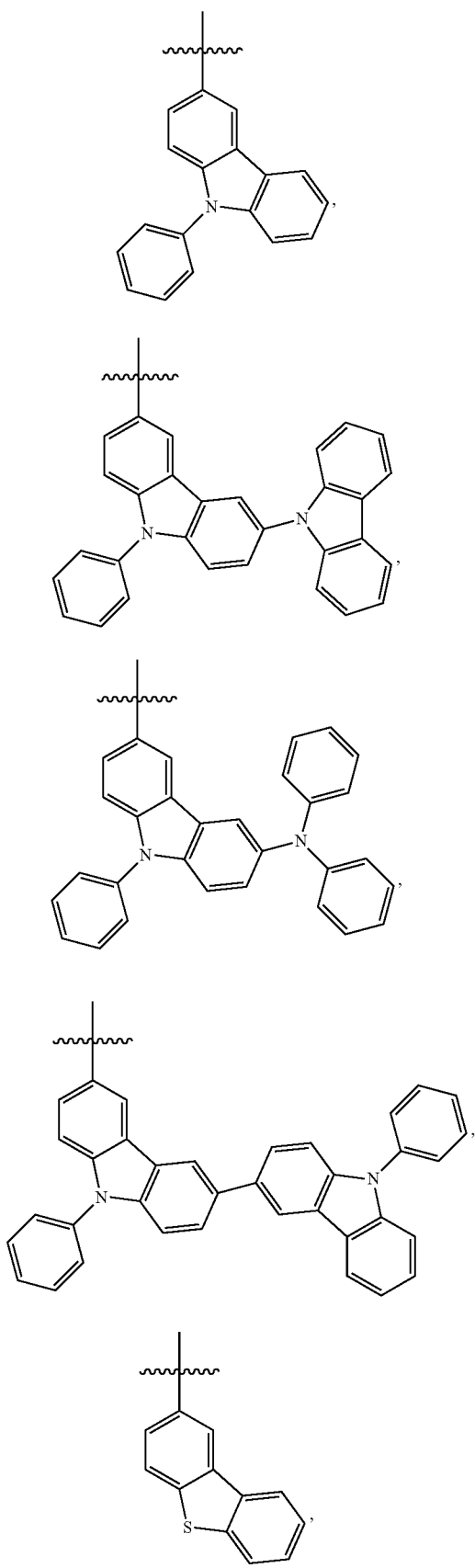
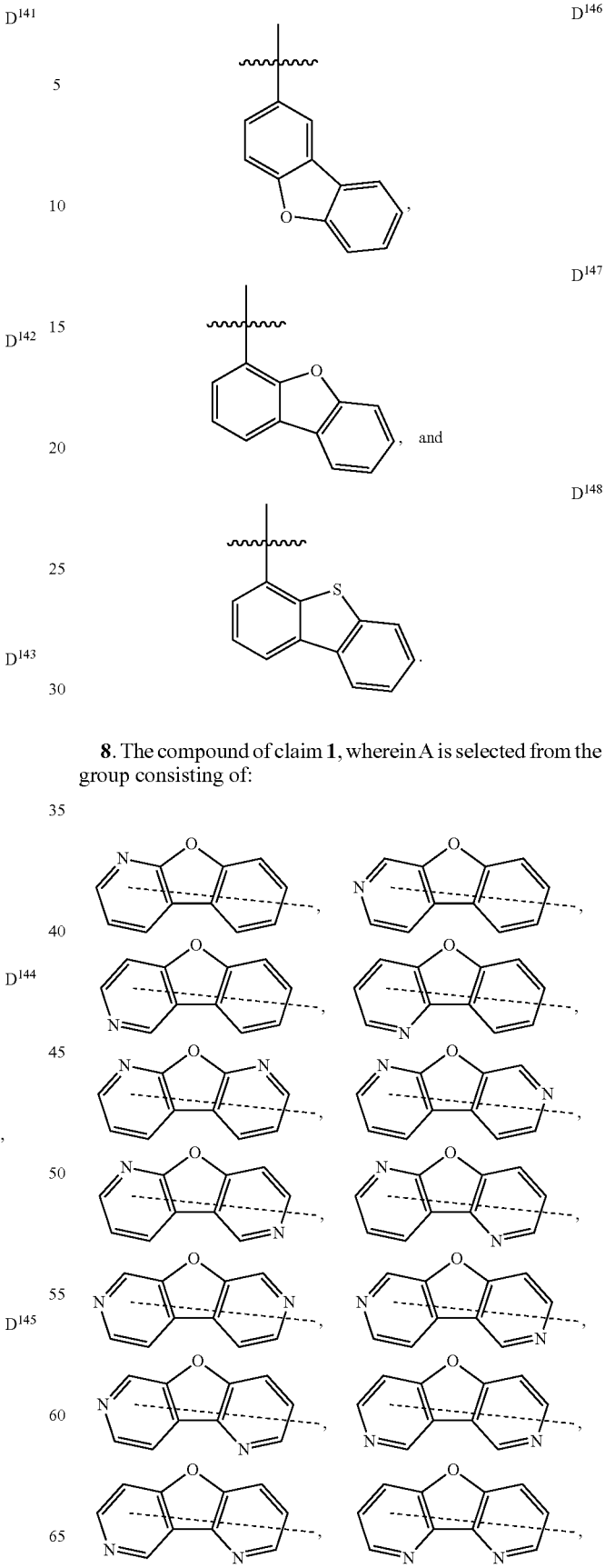
8. The compound of claim 1, wherein A is selected from the group consisting of:
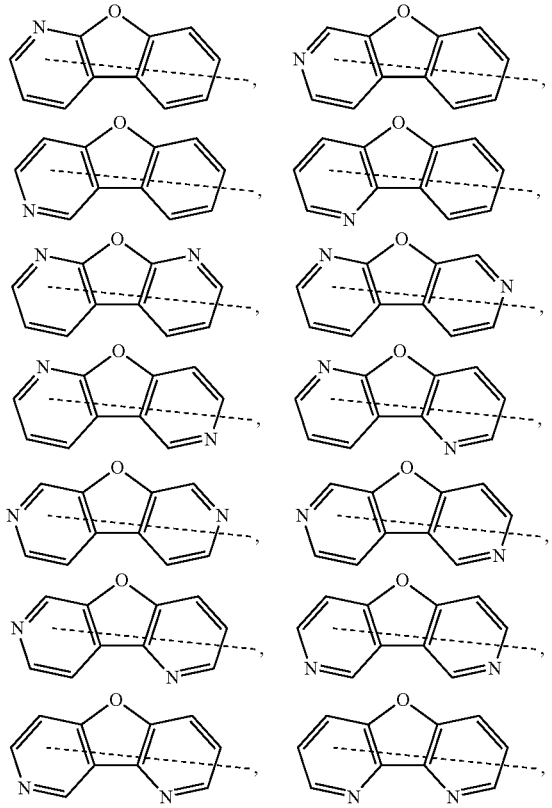

-continued

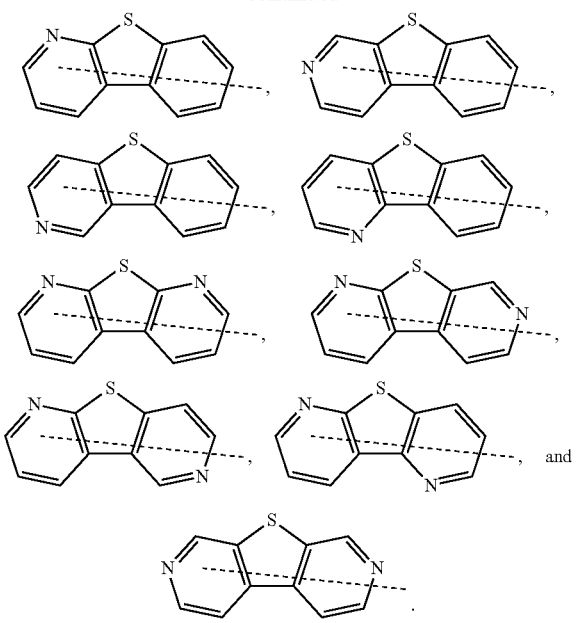

9. The compound of claim 1, wherein the compound has general a formula II:

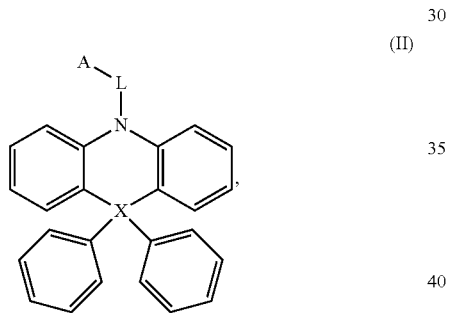

wherein
X is Si or Ge;
L comprises a group selected from a group consisting of

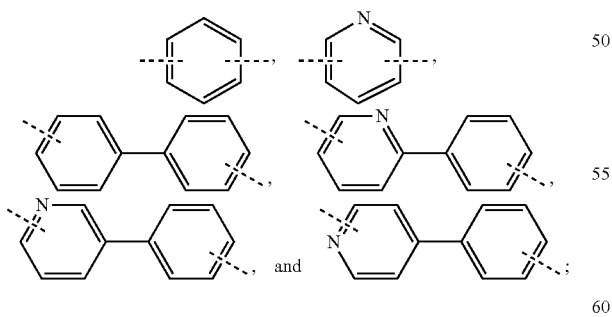

and
A contains a group selected from the group consisting of indole, carbazole, dibenzofuran, dibenzothiophene, triphenylene, azacarbazole, azadibenzofuran, azadibenzothiophene, azadibenzoselenophene and azatriphenylene group.

10. The compound of claim 9, wherein L comprises a group of

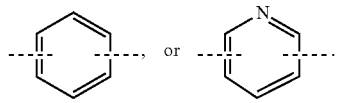

11. The compound of claim 9, wherein the compound is

Compound 8

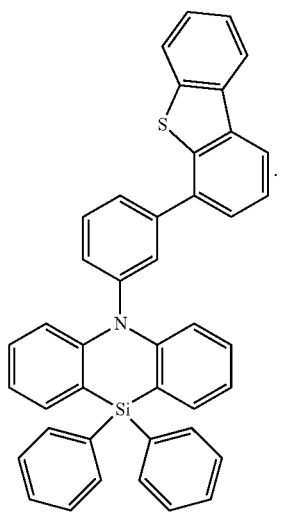

12. The compound of claim 9, wherein the compound is:

Compound 10

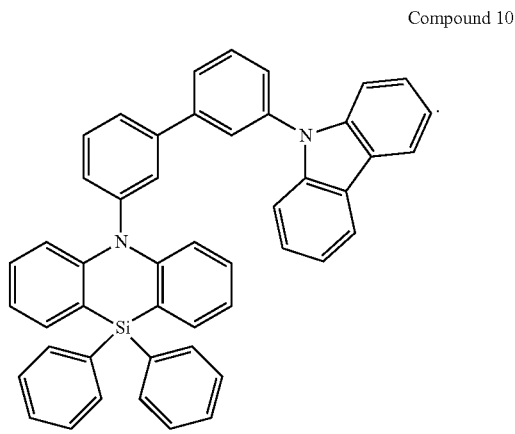 [SMILES: c1ccc([Si]2(c3ccccc3)c3ccccc3N(c3cccc(-c4cccc(-n5c6ccccc6c6ccccc65)c4)c3)c3ccccc32)cc1]

13. The compound of claim 1, wherein the compound is selected from the group consisting of:
Compound 1
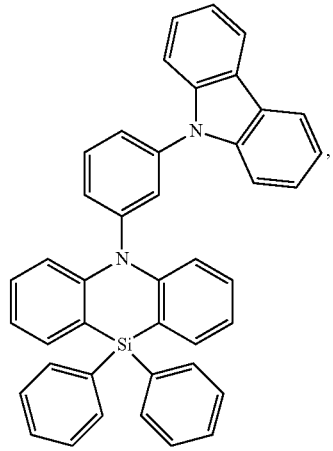
Compound 2
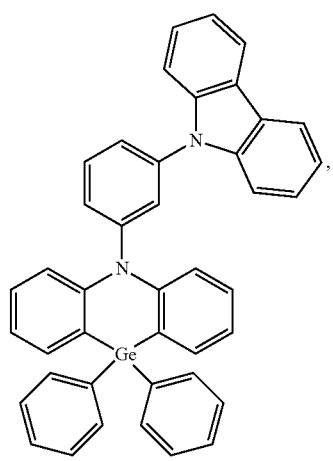
Compound 3
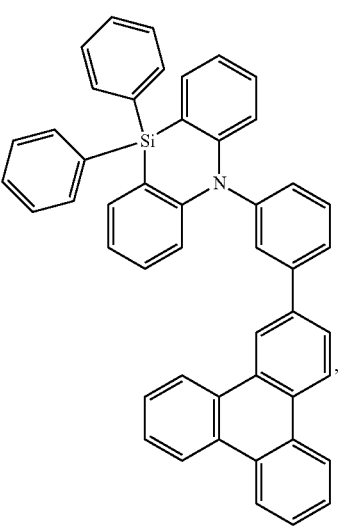
Compound 4
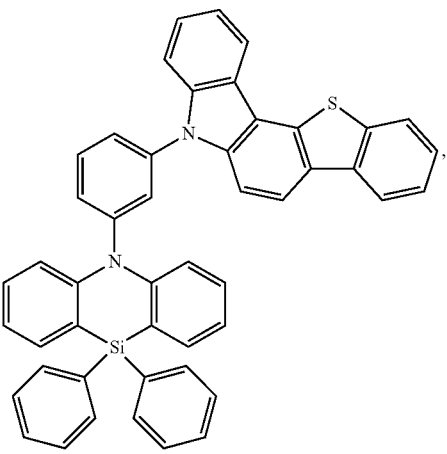
Compound 5
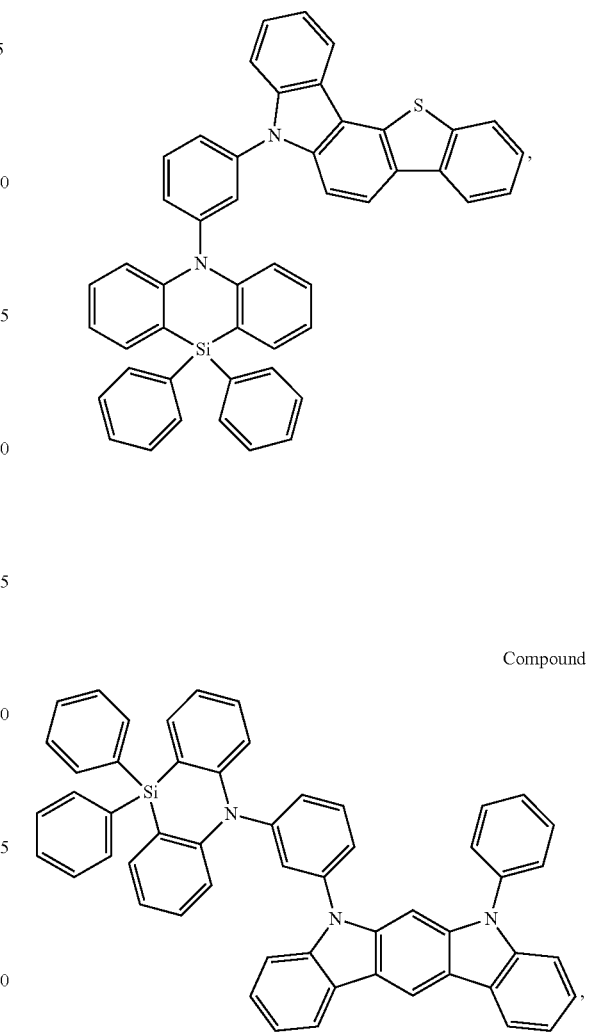
Compound 6
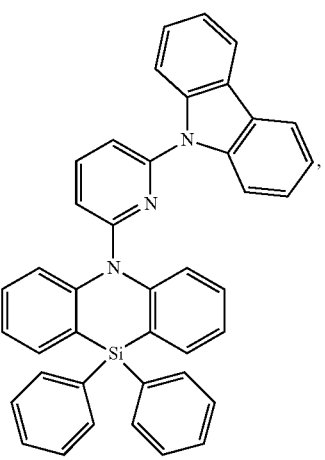

Compound 7
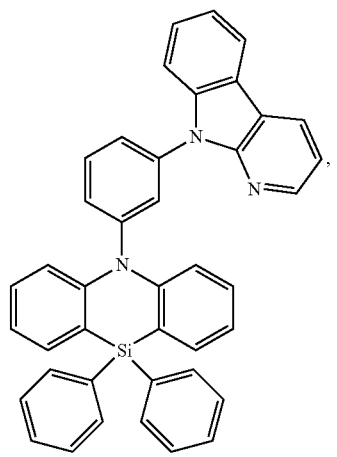
Compound 8
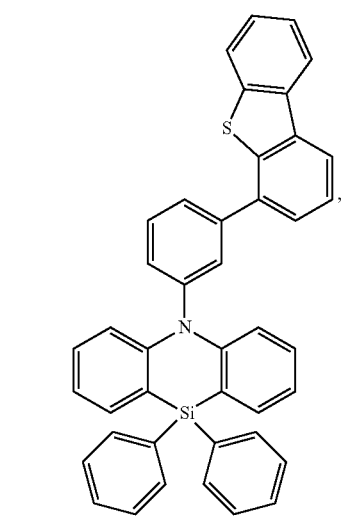
Compound 9
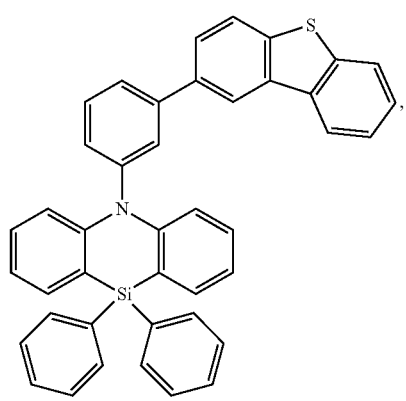
Compound 10
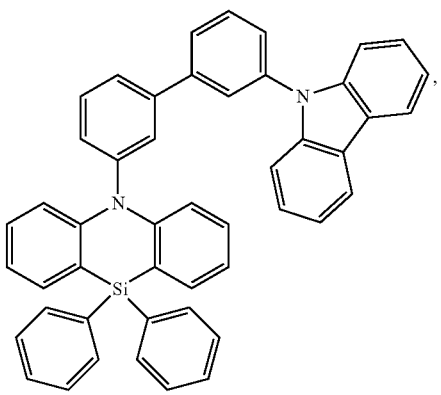
Compound 11
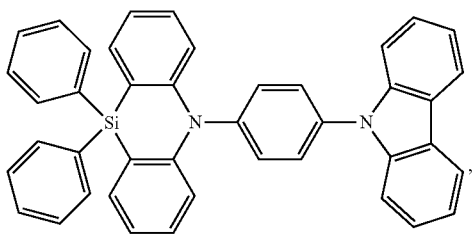
Compound 12
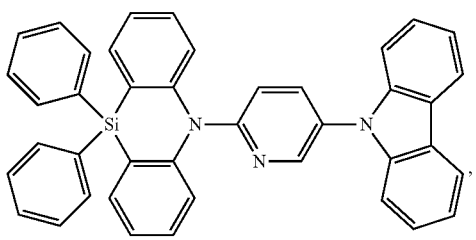
Compound 13
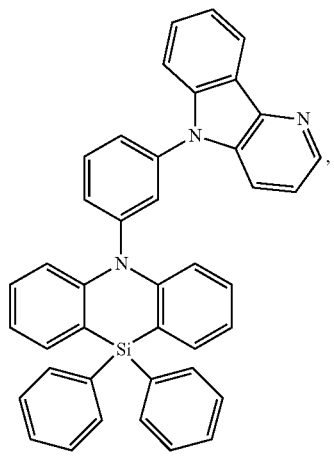

Compound 14
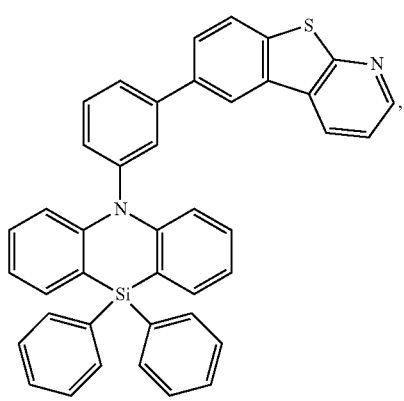
Compound 15
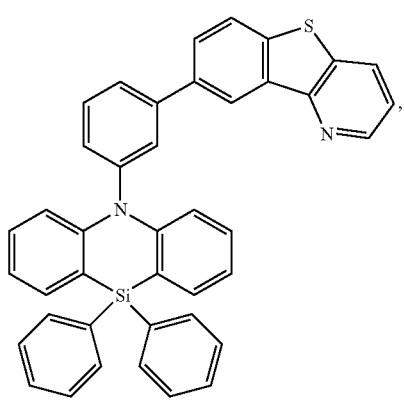
Compound 16
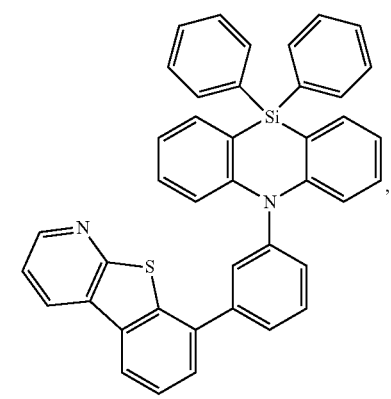
Compound 17
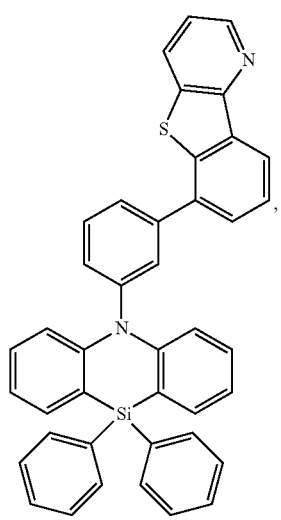
Compound 18
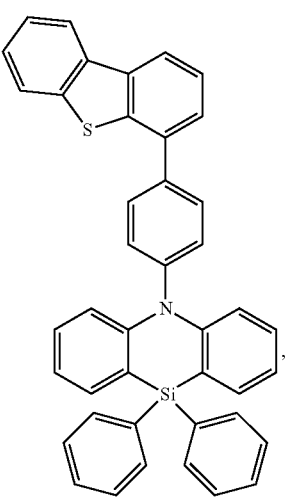
Compound 19
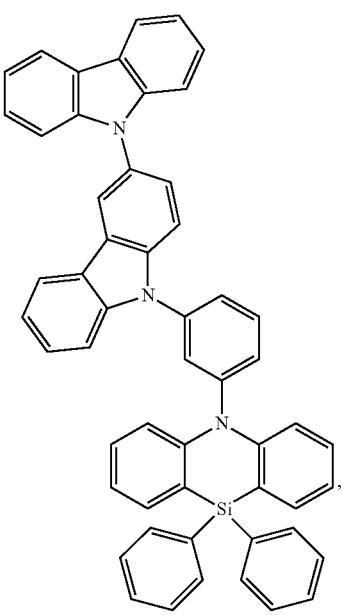

-continued
Compound 20
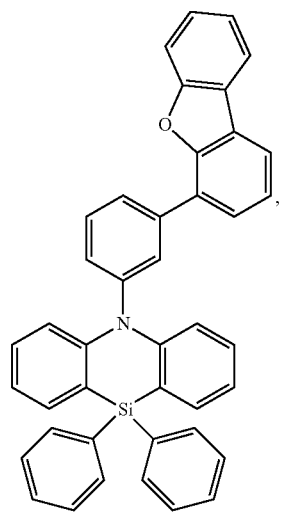
Compound 21
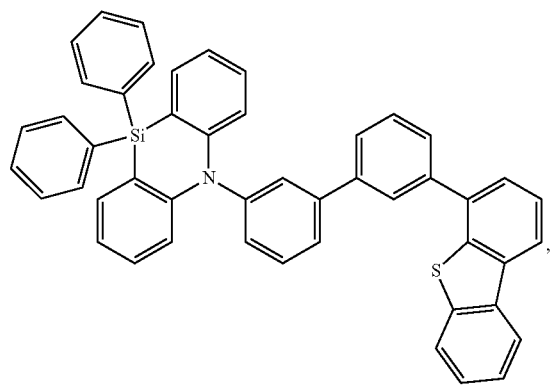
Compound 22
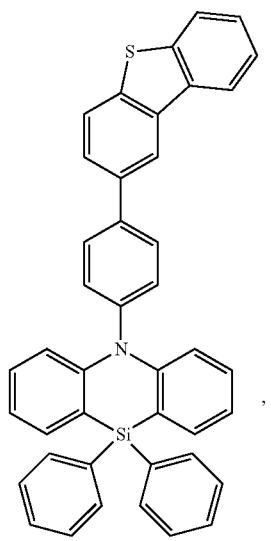
-continued
Compound 23
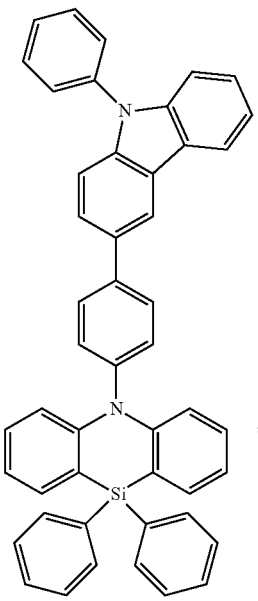
Compound 24
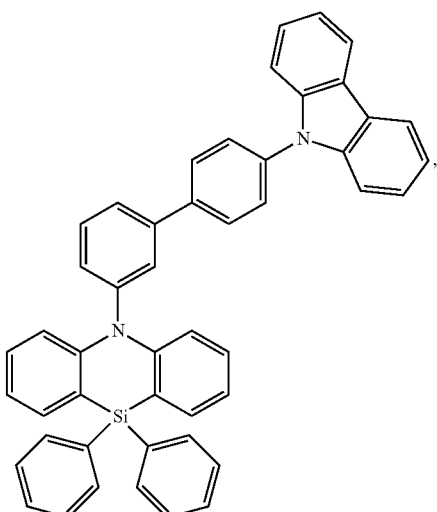
Compound 25
Compound 26
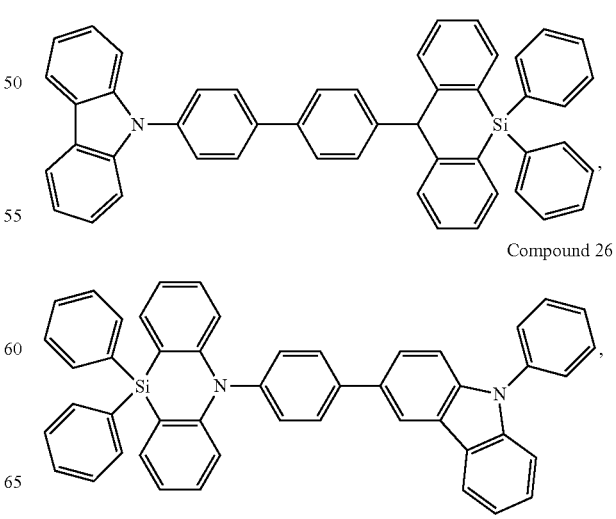

Compound 27
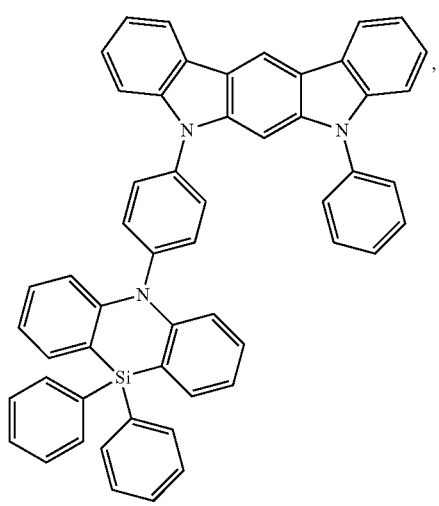
Compound 30
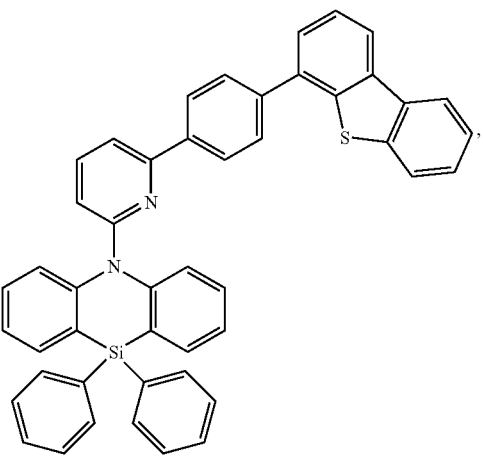
Compound 28
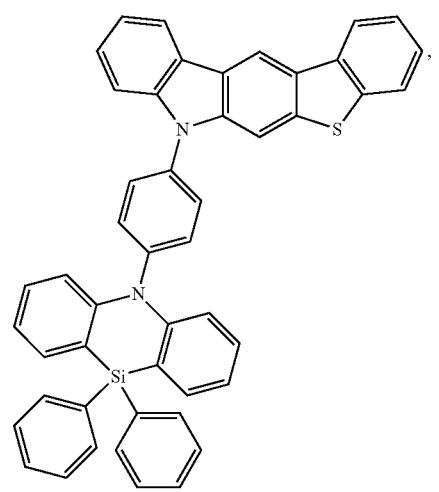
Compound 31
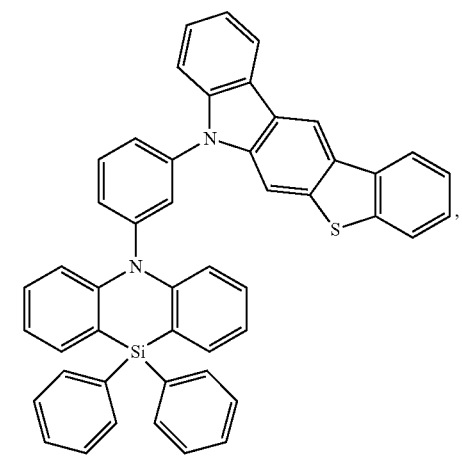
Compound 29
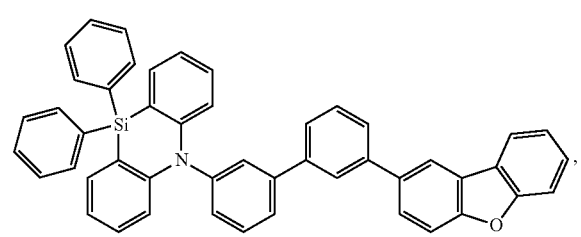
Compound 32
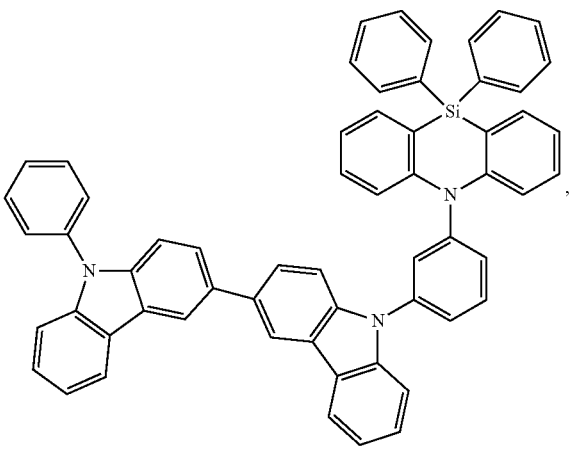

Compound 33

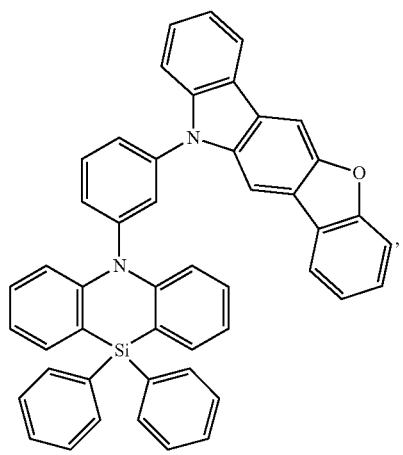

Compound 34

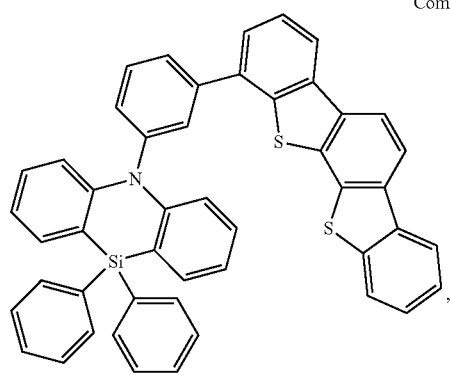

Compound 35

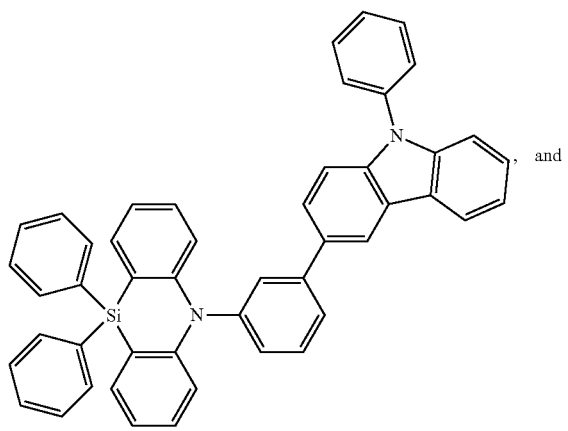

Compound 36

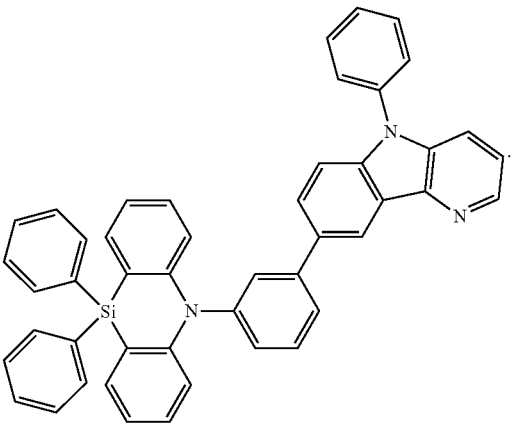

14. A first device comprising an organic light-emitting device, further comprising:
an anode;
a cathode; and
an organic layer, disposed between the anode and the cathode, comprising a compound having a formula I:

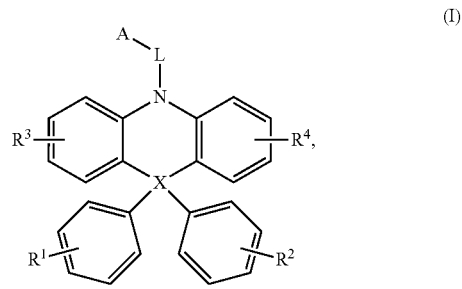

(I)

wherein
X is Si or Ge;
$R^1$ and $R^2$ represent mono, di, tri, tetra, or penta substitutions or no substitution;
$R^3$, $R^4$ represent mono, di, tri, or tetra substitutions or no substitution;
$R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
$R^1$ and $R^2$ are optionally joined to form a ring, which may be further substituted;
L is a single bond or comprises an aryl or heteroaryl group having from 5-20 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof; and
A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof, which are optionally further substituted with one or more groups selected from hydrogen, deuterium, alkyl, cycloalkyl, arylalkyl, alkoxy, aryloxy, amino, silyl, aryl, heteroaryl, and combinations thereof;

wherein the substitution of one or more groups in A is optionally fused to the indole, carbazole, bensofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group.

15. The first device of claim 14, wherein the compound of the formula I is selected from the group consisting of:

Compound 1

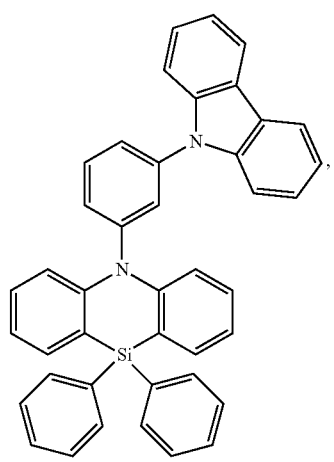

Compound 2

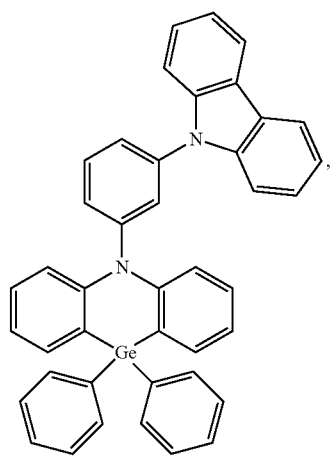

Compound 3

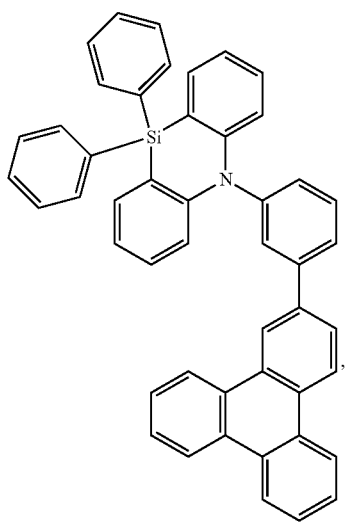

Compound 4

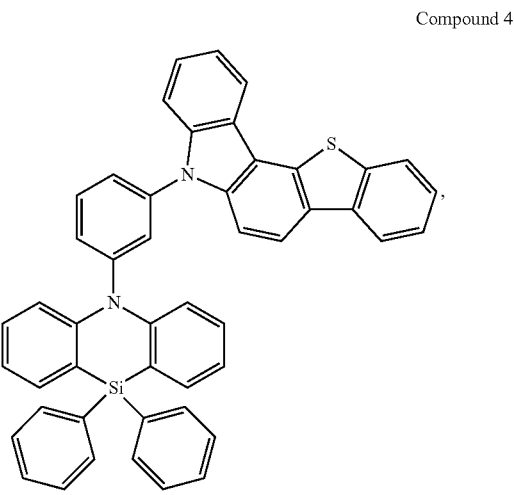

Compound 5

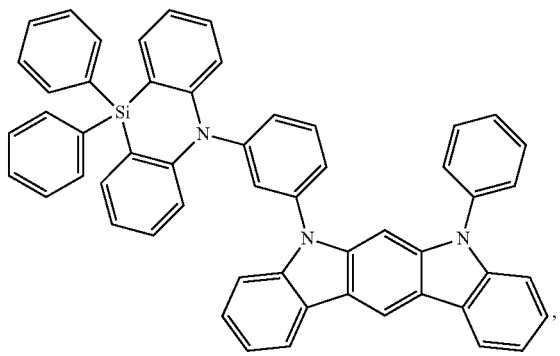

-continued
Compound 6
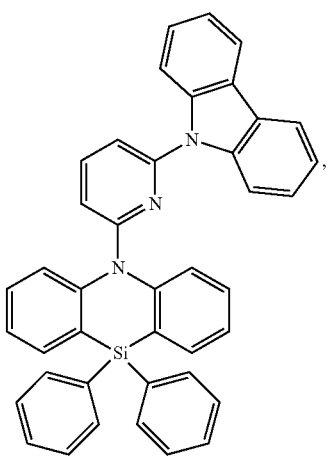
Compound 7
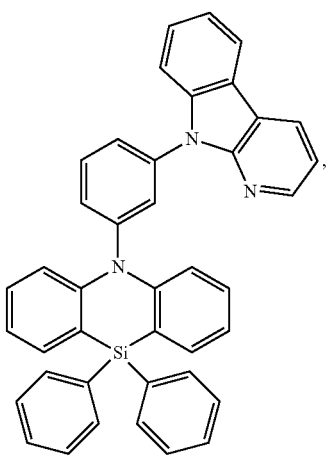
Compound 8
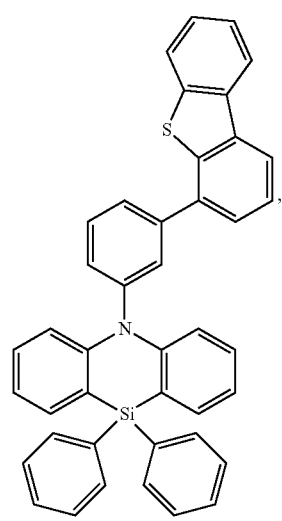
Compound 9
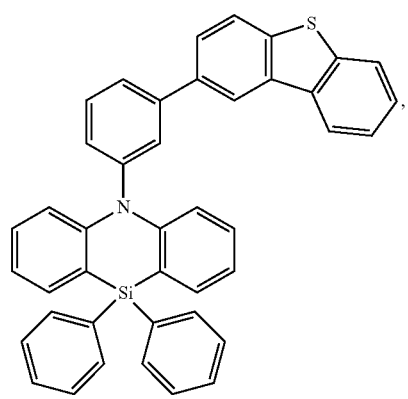
Compound 10
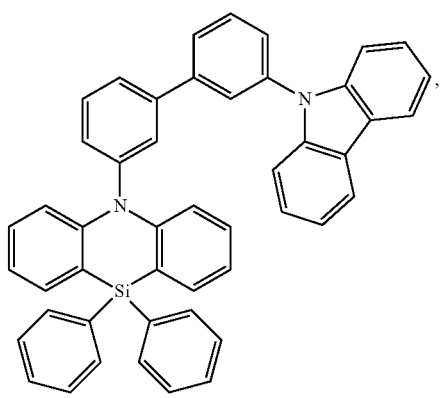
Compound 11
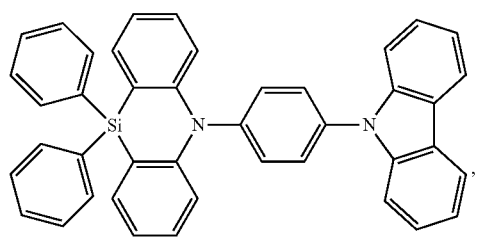
Compound 12
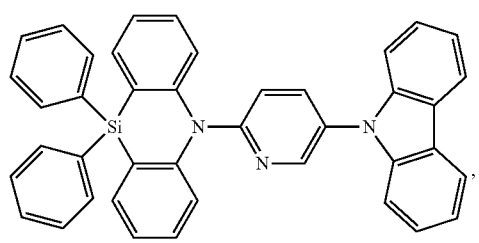

-continued
Compound 13
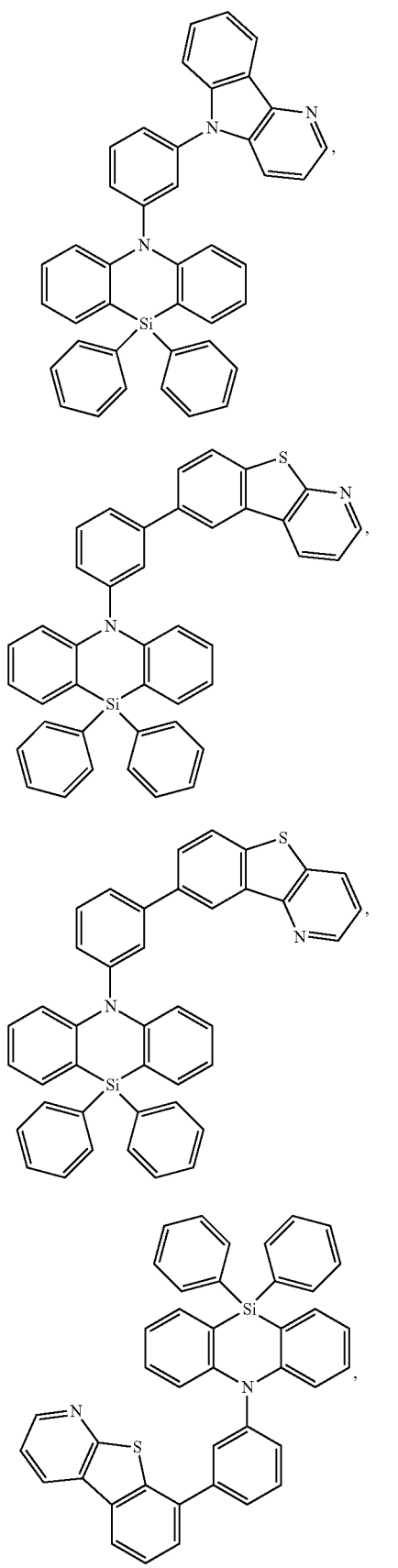
Compound 14
Compound 15
Compound 16
-continued
Compound 17
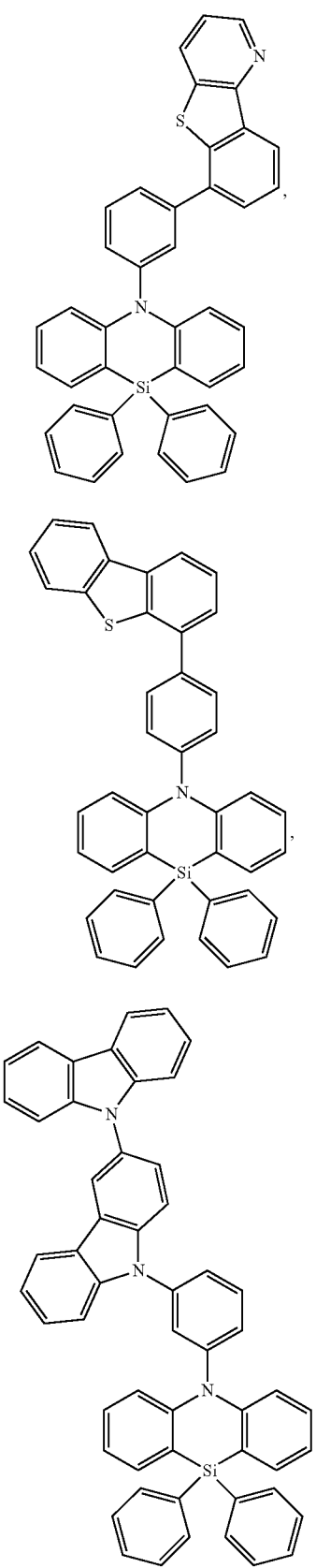
Compound 18
Compound 19

Compound 20
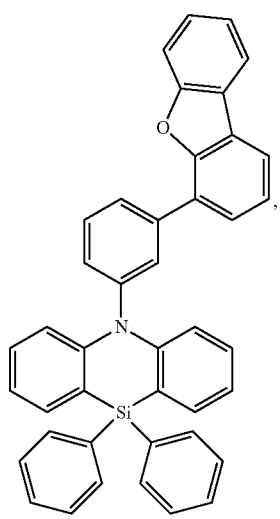
Compound 23
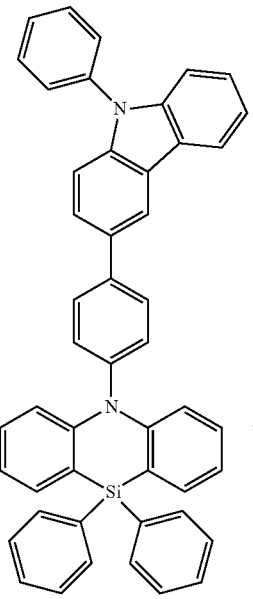
Compound 21
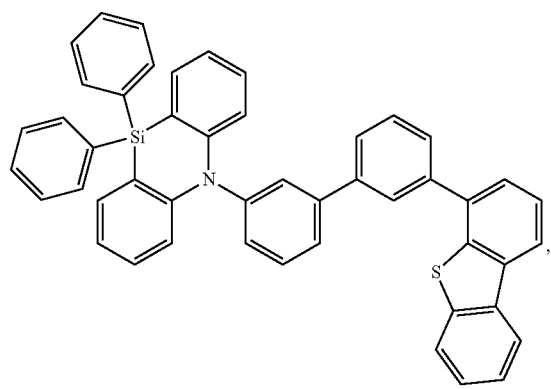
Compound 24
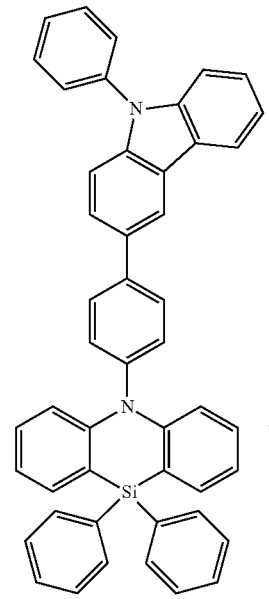
Compound 22
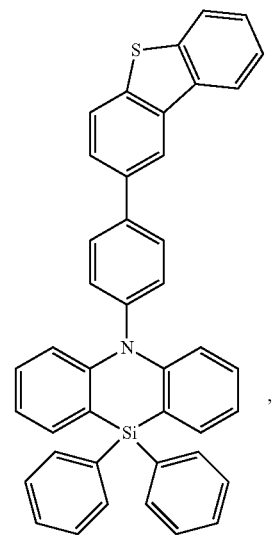
Compound 25
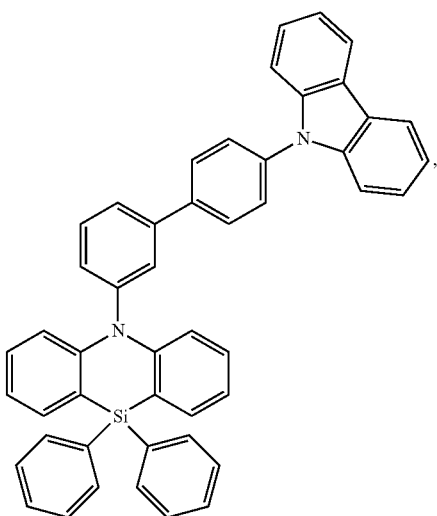
Compound 26
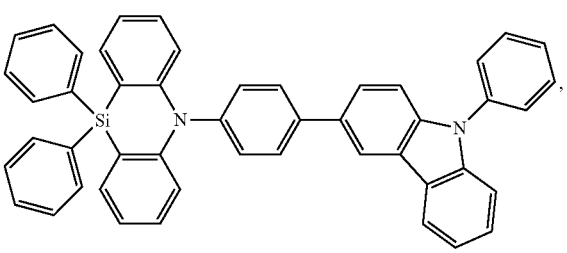

Compound 27
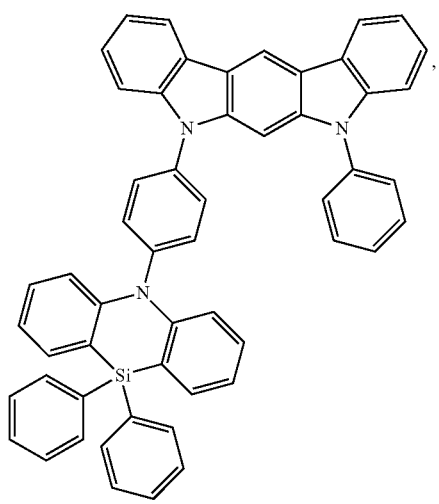
Compound 28
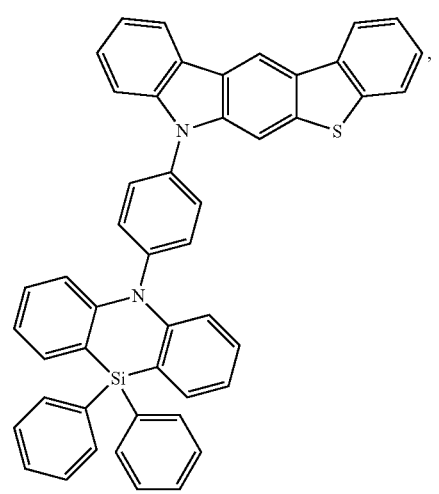
Compound 29
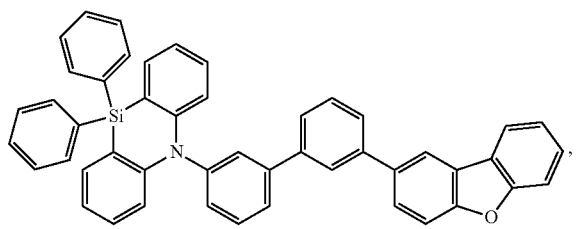
Compound 30
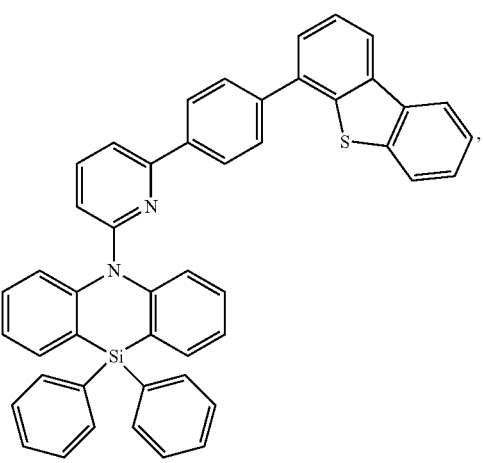
Compound 31
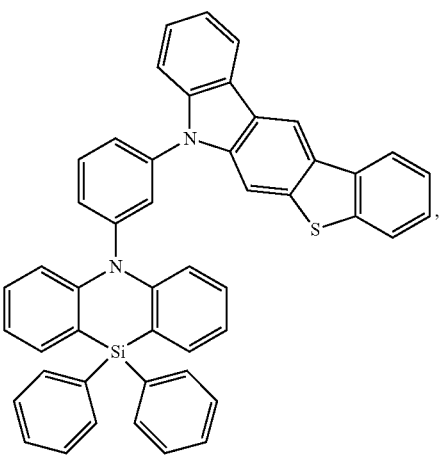
Compound 32
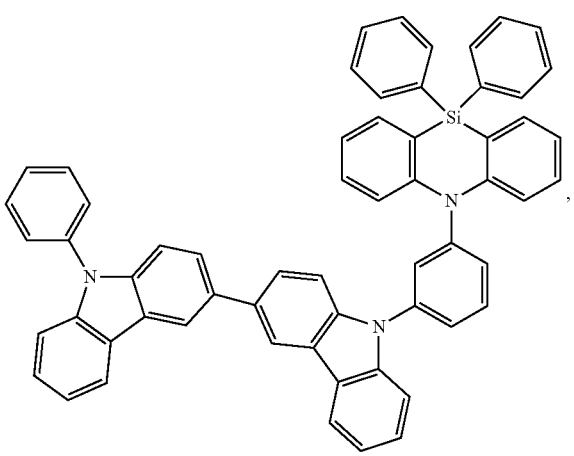

Compound 33

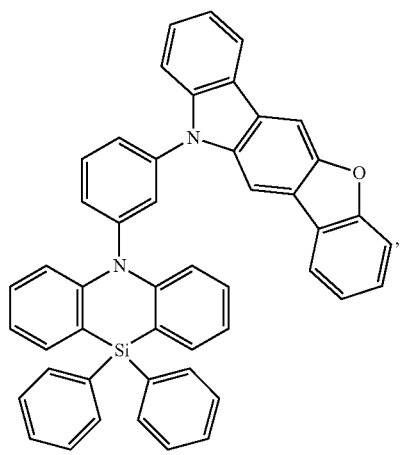

Compound 34

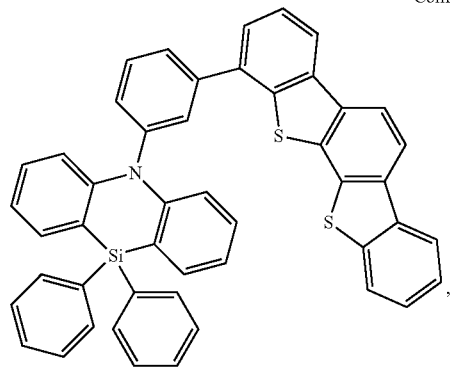

Compound 35

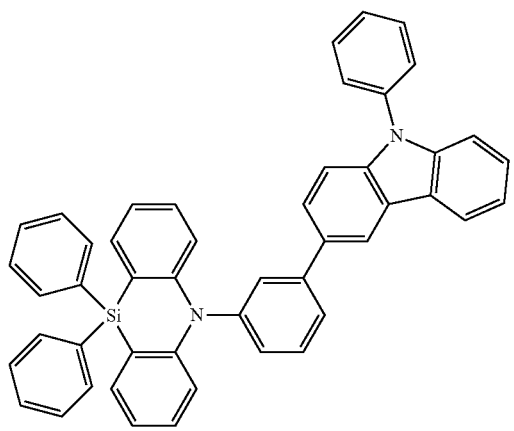

Compound 36

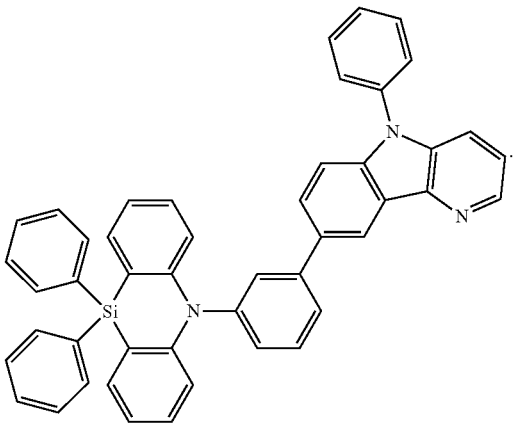

16. The first device of claim 14, wherein the organic layer is an emissive layer and the compound of the formula I is a host.

17. The first device of claim 14, wherein the organic layer further comprises an emissive dopant.

18. The first device of claim 17, wherein the emissive dopant is a transition metal complex having at least one ligand selected from the group consisting of:

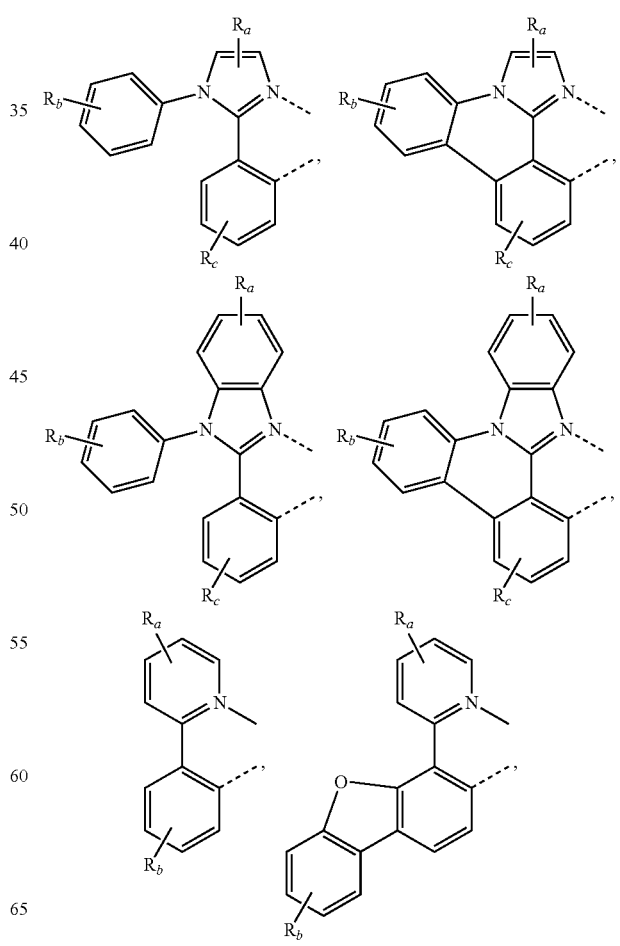

-continued

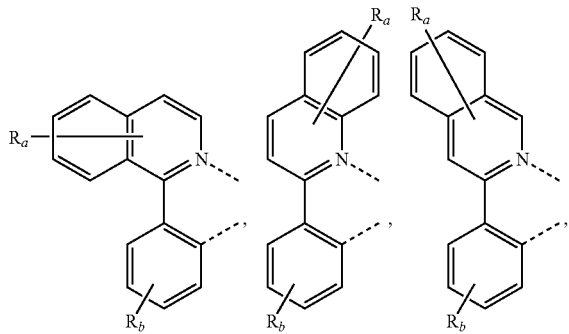

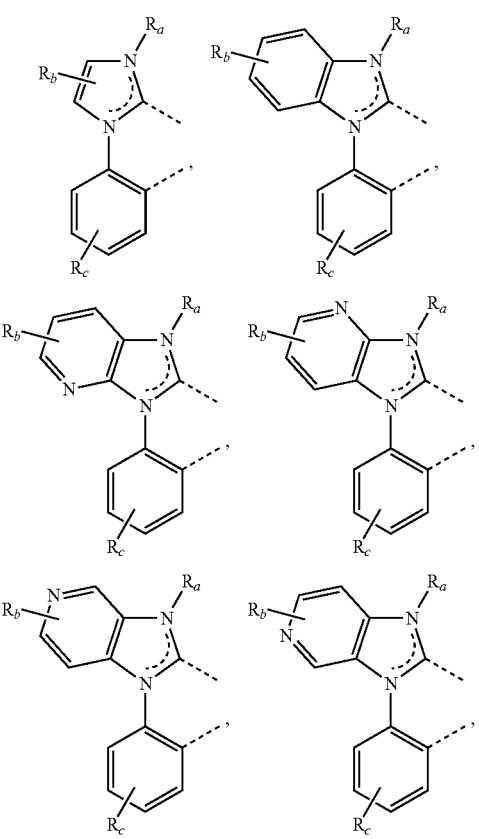

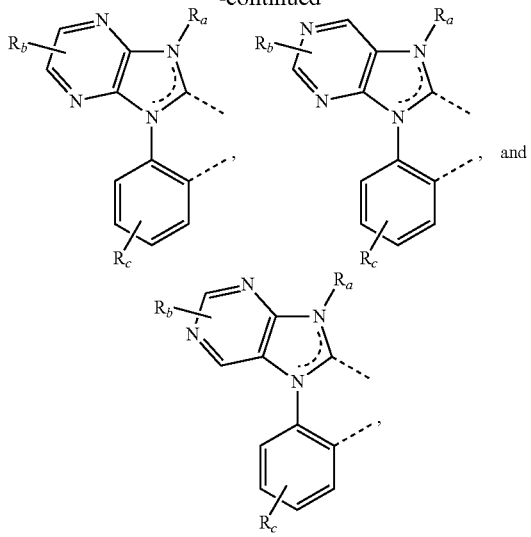

wherein
$R_a$, $R_b$, and $R_c$ may represent mono, di, tri or tetra substitutions;
$R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
two adjacent substituents of $R_a$, $R_b$, and $R_c$ are optionally joined to form a fused ring.

19. The first device of claim 14, wherein the organic layer is a blocking layer and the compound having the formula I is a blocking material in the organic layer.

20. The first device of claim 14, wherein the organic layer is an electron transporting and the compound having the formula I is an electron transporting material in the organic layer.

21. The first device of claim 14, wherein the first device is a consumer product.

22. The first device of claim 14, wherein the first device is an organic light-emitting device.

23. The first device of claim 14, wherein the first device comprises a lighting panel.

24. A composition comprising the compound of claim 1.

* * * * *

UNITED STATES PATENT AND TRADEMARK OFFICE
CERTIFICATE OF CORRECTION

PATENT NO. : 8,927,749 B2  Page 1 of 2
APPLICATION NO. : 13/788775
DATED : January 6, 2015
INVENTOR(S) : Pierre-Luc T. Boudreault et al.

It is certified that error appears in the above-identified patent and that said Letters Patent is hereby corrected as shown below:

In the Specification:

Column 34, Line 7, delete

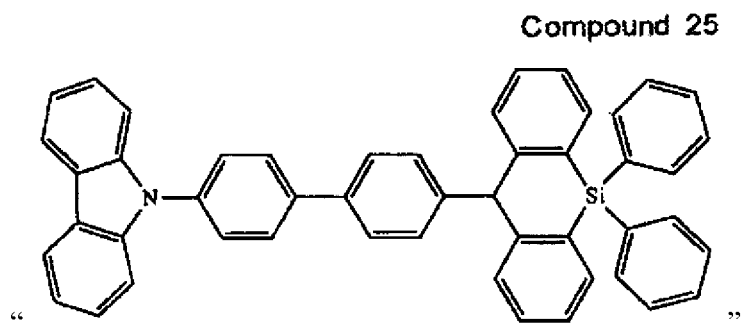

" "

And insert

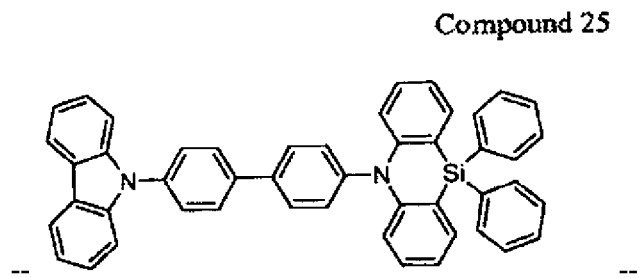

-- --

Signed and Sealed this
Fourteenth Day of April, 2015

Michelle K. Lee
*Director of the United States Patent and Trademark Office*

CERTIFICATE OF CORRECTION (continued)
U.S. Pat. No. 8,927,749 B2

In the Claims:

In Claim 13, Column 158, Line 52, delete

"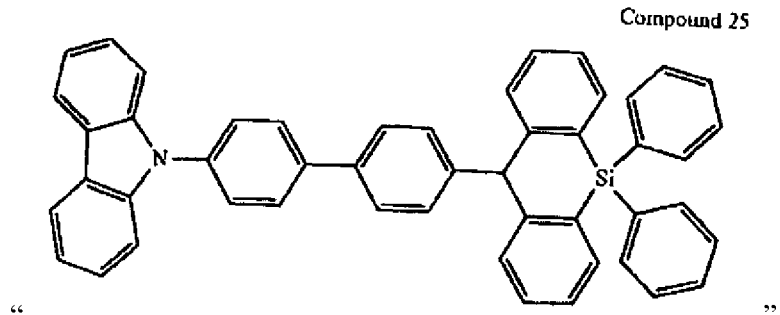"

And insert

--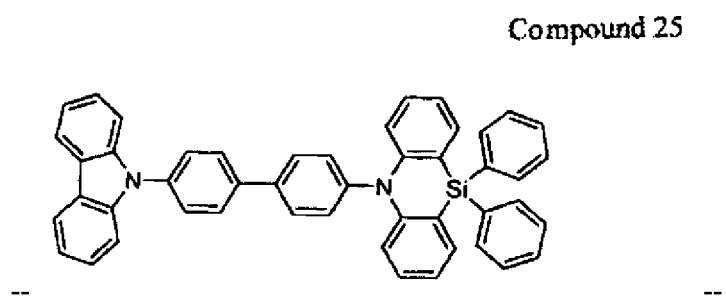--

In Claim 15, Column 170, Line 52, delete

"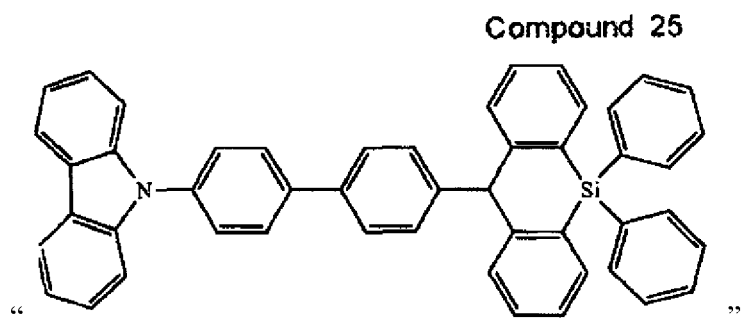"

And insert

--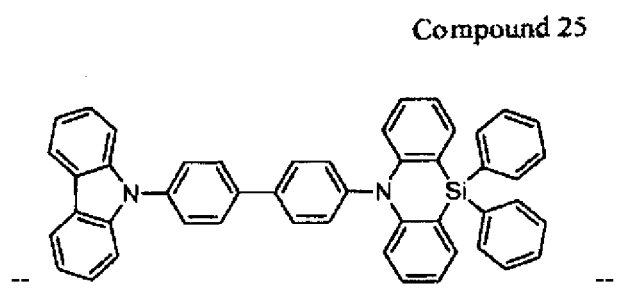--